(12) United States Patent
Sapio et al.

(10) Patent No.: US 11,986,401 B2
(45) Date of Patent: May 21, 2024

(54) SHOULDER IMPLANT IMPACTOR WITH STABILIZATION FEATURES

(71) Applicant: Howmedica Osteonics Corp., Mahwah, NJ (US)

(72) Inventors: Daniel E. Sapio, Mohegan Lake, NY (US); Andrew J. Nelson, New City, NY (US); Gennaro A. Barile, Secaucus, NJ (US); Sunny Shorabh, Ghaziabad (IN)

(73) Assignee: Howmedica Osteonics Corp., Mahwah, NJ (US)

( * ) Notice: Subject to any disclaimer, the term of this patent is extended or adjusted under 35 U.S.C. 154(b) by 785 days.

(21) Appl. No.: 16/914,740

(22) Filed: Jun. 29, 2020

(65) Prior Publication Data

US 2021/0045895 A1 Feb. 18, 2021

Related U.S. Application Data

(60) Provisional application No. 62/885,864, filed on Aug. 13, 2019.

(51) Int. Cl.
*A61F 2/46* (2006.01)
*A61F 2/30* (2006.01)
*A61F 2/40* (2006.01)

(52) U.S. Cl.
CPC ........ *A61F 2/4612* (2013.01); *A61F 2/30771* (2013.01); *A61F 2/4014* (2013.01); *A61F 2002/30331* (2013.01); *A61F 2002/30841* (2013.01); *A61F 2002/4022* (2013.01); *A61F 2002/4627* (2013.01); *A61F 2002/4629* (2013.01); *A61F 2002/4681* (2013.01)

(58) Field of Classification Search
CPC .................. A61F 2/4612; A61F 2/4014; A61F 2002/30331; A61F 2002/30841; A61F 2/30771; A61F 2002/4022; A61F 2002/4629; A61F 2002/4681
See application file for complete search history.

(56) References Cited

U.S. PATENT DOCUMENTS

| 5,489,310 A | * | 2/1996 | Mikhail | ................ A61F 2/4081 623/19.11 |
|---|---|---|---|---|
| 10,028,838 B2 | | 7/2018 | Hodorek et al. | |
| 2012/0259312 A1 | * | 10/2012 | Iannotti | ................. A61B 17/88 604/173 |

(Continued)

*Primary Examiner* — Zade Coley
*Assistant Examiner* — Diana Jones
(74) *Attorney, Agent, or Firm* — Lerner David LLP

(57) ABSTRACT

An impactor system is for impacting a base of a shoulder implant into a humerus. The system may include a housing having distal stabilizer configured to contact a proximal resected surface of the humerus. The distal stabilizer may define an open space. An impaction member may be slidably received within the housing. The impaction member may have a proximal surface and a distal connection mechanism adapted to connect to the base of the shoulder implant. The impaction member may be movable from a first proximal position in which the base of the shoulder implant, when connected to the impaction member, is positioned within the open space defined by the distal stabilizer, to a second distal position in which the base of the shoulder implant, when connected to the impaction member, is positioned at least partially distal to the open space defined by the distal stabilizer.

20 Claims, 34 Drawing Sheets

(56) References Cited

U.S. PATENT DOCUMENTS

| | | | |
|---|---|---|---|
| 2013/0261630 A1* | 10/2013 | Courtney, Jr. | A61B 17/8872 606/84 |
| 2013/0331849 A1* | 12/2013 | Splieth | A61F 2/4612 606/99 |
| 2014/0005641 A1* | 1/2014 | Slade | A61B 17/00 606/1 |
| 2016/0228262 A1* | 8/2016 | Bailey | A61F 2/34 |
| 2018/0271668 A1 | 9/2018 | Kemp et al. | |

* cited by examiner

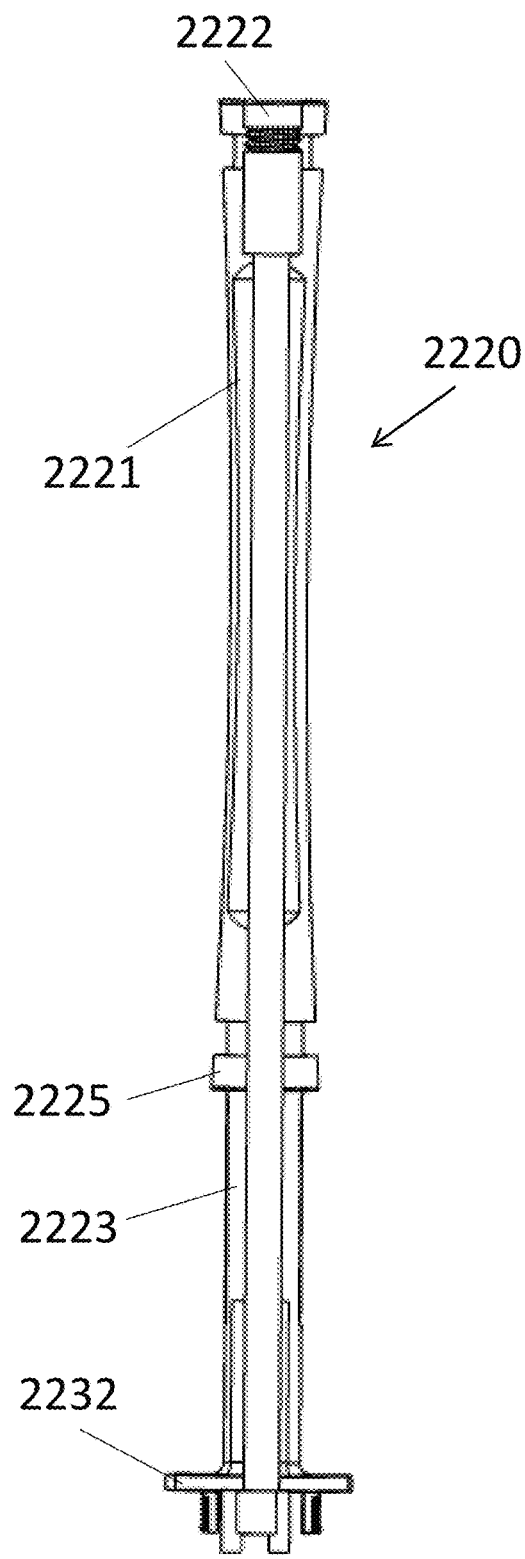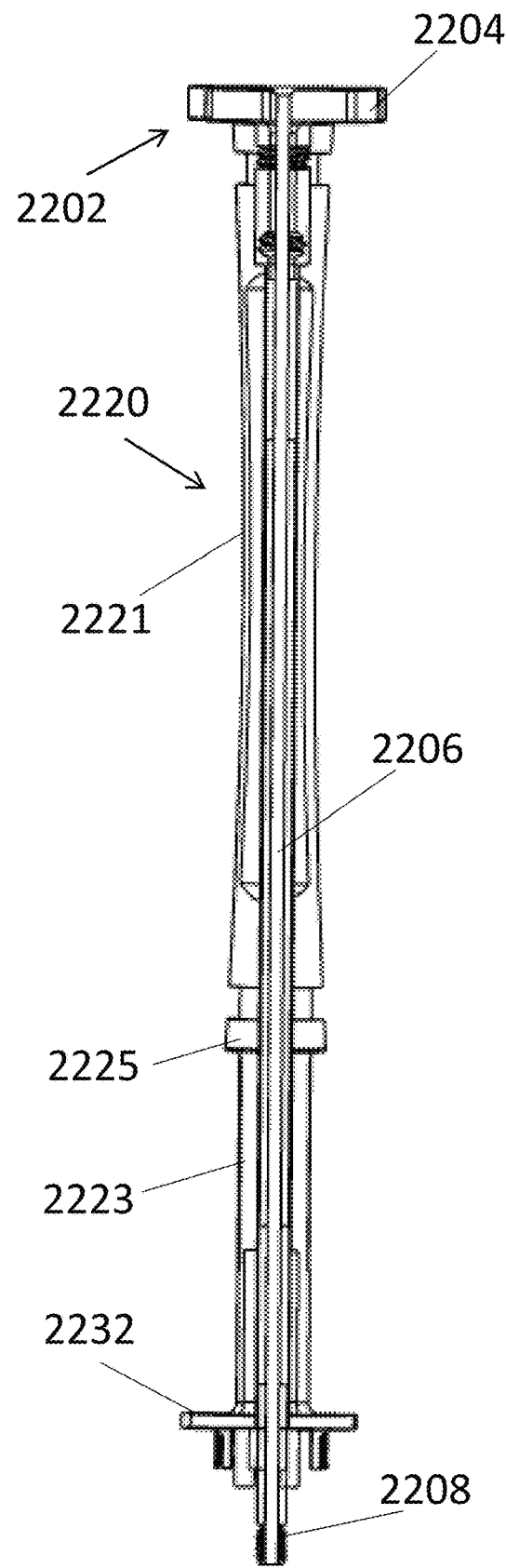
FIG. 32  FIG. 33

SHOULDER IMPLANT IMPACTOR WITH STABILIZATION FEATURES

CROSS-REFERENCE TO RELATED APPLICATIONS

This applications claims priority of the filing date of U.S. Provisional Patent Application No. 62/885,864, filed Aug. 13, 2019, the disclosure of which is hereby incorporated by reference herein.

BACKGROUND OF THE DISCLOSURE

Over time and through repeated use, bones and joints can become damaged or worn. For example, repetitive strain on bones and joints (e.g., through athletic activity), traumatic events, and certain diseases (e.g., arthritis) can cause cartilage in joint areas, for example, which normally provides a cushioning effect, to wear down. When the cartilage wears down, fluid can accumulate in the joint areas, resulting in pain, stiffness, and decreased mobility. The same can happen in cases where tendons in a joint become lax or soft tissues in or adjacent the joint become damaged or worn.

Arthroplasty procedures can be used to repair such damaged joints. During a typical arthroplasty procedure, an arthritic or otherwise dysfunctional joint can be remodeled or realigned. A prosthesis or prostheses can be implanted to repair the damaged region(s). Arthroplasty procedures may take place in any of a number of different regions of the body, such as the knees, hips, shoulders, or elbows, for example. One type of arthroplasty procedure is a shoulder arthroplasty, in which a damaged shoulder joint may be replaced with prosthetic implants. The shoulder joint may have been damaged by, for example, arthritis (e.g., severe osteoarthritis or degenerative arthritis), trauma, or a rare destructive joint disease.

Prostheses that are implanted into a damaged region may provide support and structure to the damaged region, and may help to restore the damaged region, thereby enhancing its functionality. Prior to implantation of a prosthesis in a damaged region, the damaged region may be prepared to receive the prosthesis. In the case of a shoulder arthroplasty procedure, one or more of the bones in the shoulder area, such as the humerus and/or glenoid, may be treated (e.g., cut, drilled, reamed, and/or resurfaced) to provide one or more surfaces that can align with the implant and thereby accommodate the implant.

It is often preferable to maintain as much of a patient's natural bone stock as possible during such a procedure. Prostheses generally have a certain life expectancy and in certain cases need to be replaced at some point. If one or more prostheses need to be removed and/or replaced in a revision procedure, a large bone void could be left after their removal. In certain cases, this bone void is not ideal for receipt of revision components. Preserving natural bone stock may be desirable for the ability to even perform a revision procedure.

In total or partial arthroplasty surgery, stemmed prostheses are often used which generally include a long stem that passes through a center of a long bone, the stem helping to anchor the remaining components of the prosthesis. However, stemmed prostheses may result in a large amount of healthy bone being removed in order to accommodate the stem. In some cases, stemless prostheses may be used, which may result in less healthy bone stock being removed. However, in some cases stemless prostheses may not anchor the particular prosthesis as well as a stemmed prosthesis would.

In additional, some stemless shoulder prostheses may require the removal of significant proximal humeral bone, which may compromise the proximal humerus bone and result in more challenging revision surgeries.

BRIEF SUMMARY OF THE DISCLOSURE

According to a first embodiment of the disclosure, an impactor system is for impacting a base of a shoulder implant into a humerus. The system includes a housing having distal stabilizer configured to contact a proximal resected surface of the humerus, the distal stabilizer defining an open space. An impaction member is slidably received within the housing, the impaction member having a proximal surface and a distal connection mechanism adapted to connect to the base of the shoulder implant. The impaction member is movable from a first proximal position in which the base of the shoulder implant, when connected to the impaction member, is positioned within the open space defined by the distal stabilizer, to a second distal position in which the base of the shoulder implant, when connected to the impaction member, is positioned at least partially distal to the open space defined by the distal stabilizer. The distal stabilizer may include a substantially circular rim at a distal end of the distal stabilizer. The distal stabilizer may include a plurality of extensions extending along an axis substantially parallel to a longitudinal axis of the impactor system. Each of the plurality of extensions may be circumferentially spaced apart from one another. Each of the plurality of extensions may include a frictional engagement member adapted to frictionally engage the proximal resected surface of the humerus. The housing may include a longitudinal slot sized and shaped to allow a portion of the impaction member to be laterally inserted through the longitudinal slot into the housing. An impaction tip may be configured to be in contact with both a distal portion of the impaction member and a proximal surface of the base of the shoulder implant. The impaction tip may include two apertures, and the impaction member may include a distal flange and two fingers extending distally form the distal flange, the two fingers configured to be received within respective ones of the two apertures. The distal flange may have a shape substantially similar to a shape of the proximal surface of the base of the shoulder implant. The impaction member may include a handle having a threaded distal tip, the threaded distal tip configured to pass through the impaction tip and into a corresponding threaded portion of the base of the shoulder implant. The impaction tip may include a plurality of extensions extending radially outward from a longitudinal center of the impaction tip, the plurality of extensions shaped and positioned to contact a cortical rim of the proximal resected surface of the humerus.

According to another embodiment of the disclosure, a method of impacting a base of a shoulder implant into a humerus includes connecting the base of the shoulder implant to a distal connection mechanism of an impaction member. A distal stabilizer of a housing may be contacted to a proximal resected surface of the humerus, the distal stabilizer defining an open space. A proximal end of the impaction member may be impacted while the impaction member is slidably received within the housing to move the impaction member from a first proximal position in which the base of the shoulder implant is positioned within the open space defined by the distal stabilizer, to a second distal position in which the base of the shoulder implant is positioned at least partially within the humerus. The distal stabilizer may include a substantially circular rim at a distal end of the distal stabilizer, and contacting the distal stabilizer to the proximal resected surface of the humerus may include contacting the substantially circular rim to the proximal resected surface. The distal stabilizer may include a plurality of extensions extending along an axis substantially parallel to a longitudinal axis of the impactor system, and contacting the distal stabilizer to the proximal resected surface of the humerus may include contacting the plurality of extensions to the proximal resected surface. Each of the plurality of extensions may include a frictional engagement member, and contacting the plurality of extensions to the proximal resected surface may include frictionally engaging the frictional engagement members to the proximal resected surface of the humerus. The method may also include contacting an impaction tip with both a distal portion of the impaction member and a proximal surface of the base of the shoulder implant. Two fingers extending distally from a distal flange of the impaction member may be inserted into corresponding ones of two apertures of the impaction tip. A threaded distal tip of a handle of the impaction member may be threaded into a corresponding threaded portion of the base of the shoulder implant, the threaded distal tip passing through the impaction tip. The method may also include positioning a plurality of extensions that extending radially outward from a longitudinal center of the impaction tip in contact with a cortical rim of the proximal resected surface of the humerus prior to impacting the proximal end of the impaction member.

BRIEF DESCRIPTION OF THE DRAWINGS

FIG. 32 is a cross-section of a shaft portion of the impaction member of FIGS. 29 and 30.

FIG. 33 is a cross-section of the handle portion received within the shaft portion.

DETAILED DESCRIPTION

It should be understood that although the term "stemless implant" is used herein, the term does not indicate that a stemless implant fully lacks any anchor, but rather a stemless implant may include an anchor that is significantly smaller and/or shorter than stems of typical known stemmed implants. Further, the stemless implants of the present disclosure generally include a base member intended for coupling to an end of a first bone of a joint, such as a humerus or femur, and an articulating member intended to attach to the base member and to provide articulation with the second bone of the joint (or a corresponding prosthesis attached to the second bone). Further, as used herein, the term "proximal," when used in connection with an implant, refers to a location closer to an individual's heart, and the term "distal," when used in connection with an implant, refers to a location farther away from the individual's heart.

When used in connection with a tool for use in conjunction with an implant, such as an impactor, the terms "proximal" and "distal" refer to positions closer to or farther away from the user of the tool, respectively, when the tool is being used as intended.

Figure 1:
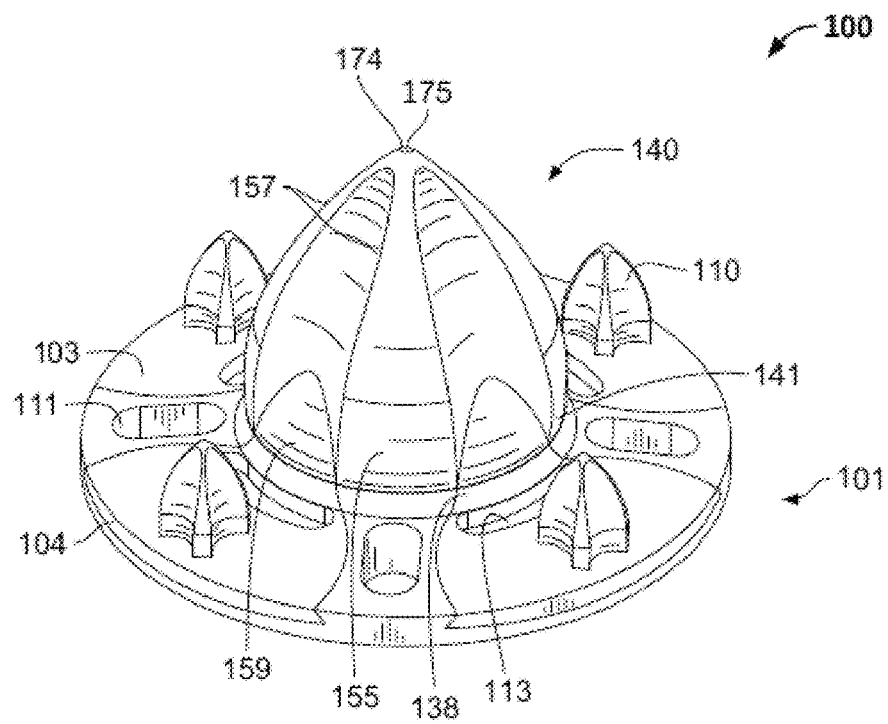
FIG. 1 is a side perspective view of a base of a shoulder implant according to an aspect of the disclosure.
Figure 2:
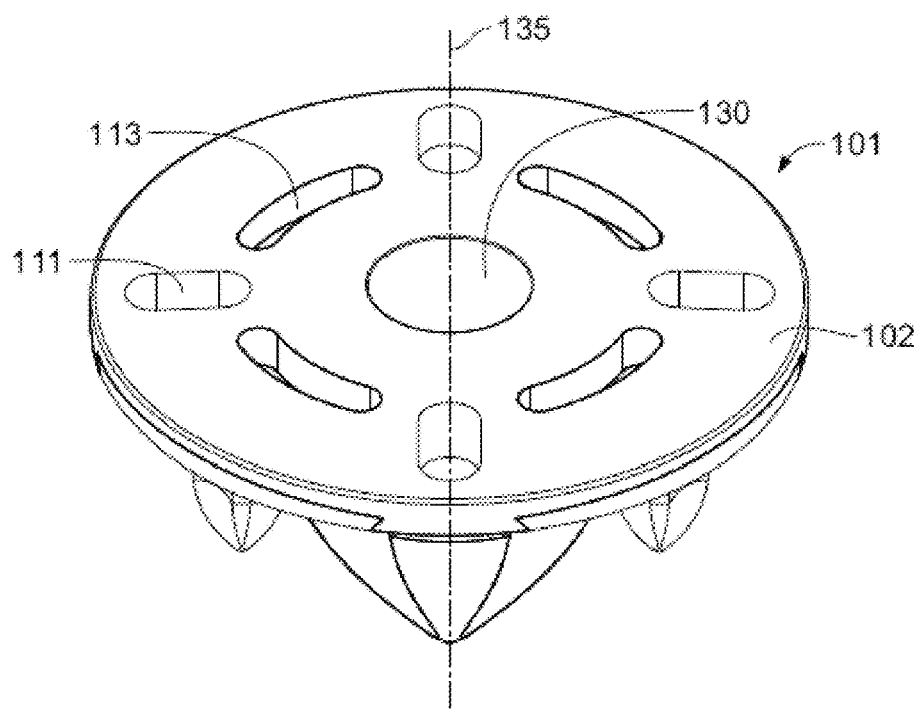
FIG. 2 is a top perspective view of the base of FIG. 1.

FIGS. 1 and 2 show a base 100 of an exemplary stemless shoulder implant. Base 100 generally includes collar 101 coupled with central anchor 140. Collar 101 may be generally cylindrical or annular and includes a proximal end surface 102, a distal bone engaging-surface 103, and a side flange surface 104. Proximal end surface 102 may be flat as shown, but in other embodiments it may be inclined or sloped. Side flange surface 104 may have a uniform height, the height measured from distal to proximal ends of side flange surface 104, or the height may vary along proximal end surface 102. Although shown as generally cylindrical or annular, collar 101 may have other shapes.

Base 100 includes central anchor 140 coupled to collar 101 at a first end 141 and extending distally from the collar along a longitudinal axis 135 to a second end 174. In the illustrated embodiment, anchor 140 is tapered along longitudinal axis 135 so that first end 141 has a relatively large diameter, with the diameter of the anchor generally narrowing toward second end 174 until the anchor terminates in distal tip 175; although, in some situations it may be appropriate for, anchor 140 to be of uniform size throughout and not tapered.

Figure 3:
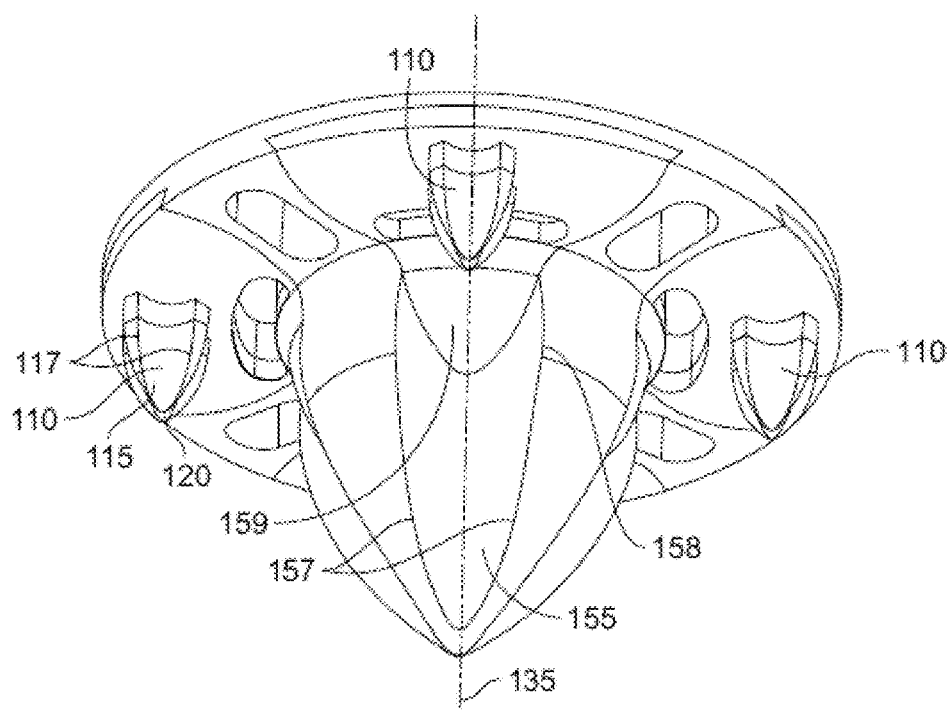
FIG. 3 is another side perspective view of the base of FIG. 1.

When used as part of a shoulder implant system, anchor 140 may be configured to be driven into the metaphyseal cancellous bone of the humerus and to facilitate engagement between base 100 and the bone for fixation. Anchor 140 may include a plurality of flutes 155 which may extend part or all of the longitudinal length of the anchor, for example from bone-engaging surface 103 to distal tip 175. Each flute 155 may be positioned between two edges 157, with the flute being recessed radially inwardly toward longitudinal axis 135 compared to the edges. Edges 157 may extend radially outwardly from longitudinal axis 135 to varying degrees depending on the position along the longitudinal axis. For example, edges 157 may have a minimum amount of radial extension from longitudinal axis 135 at or near distal tip 175. The distance which the edges 157 extend radially outwardly from longitudinal axis 135 may then increase gradually in the proximal direction toward bone-engaging surface 103. The edges 157 may reach their greatest amount of outward radial extension from longitudinal axis 135 at apex 158. From apex 158 to bone-engaging surface 103, the distance which edges 157 extend radially outward from longitudinal axis 135 may decrease until the edges connect to bone-engaging surface 103. Flutes 155 are preferably concave between two adjacent edges 157. Each flute 155 may include an enhanced fixation surface 159 in the region between bone-engaging surface 103 and a portion of the flute circumferentially aligned with apex 158. The enhanced fixation surface 159 may take the form of a porous metal surface, such as porous titanium alloy, including Tritanium® by Howmedica Osteonics Corporation. As shown in FIG. 3, fixation surface 159 may be in the general shape of a trough and may be convex. Fixation surfaces 159 may provide for enhanced in-growth of bone into anchor 140, facilitating better fixation of base 100 following implantation. Fixation surfaces 159 may be rougher than the adjacent surfaces of anchor 140, resulting in greater friction between the fixation surface 159 and the bone. This increased friction may help provide additional fixation by providing additional resistance against pull-out forces.

A fixation ring 138 may surround central anchor 140, the fixation ring extending circumferentially around the central anchor at its connection with bone-engaging surface 103. Fixation ring 138 may generally take the form of a recessed groove. As explained in greater detail below, upon implantation of base 100 into cancellous bone, the bone may flow into fixation ring 138 to help provide additional fixation. As shown in FIG. 2, fixation surfaces 159 may extend into portions of fixation ring 138 to provide stronger fixation to the bone.

When implanting base 100 into a bone, such as the cancellous bone at the proximal end of the humerus, distal tip 175 of anchor 140 is driven into the bone. Because cancellous bone is relatively soft, the bone may effectively flow along anchor 140, and in particular along the flutes 155 of the anchor. After the apex 158 of the edges 157 passes into the bone, some volume of bone may effectively "spring" back into the areas of flute 155 adjacent enhanced fixation surfaces 159 and also into fixation ring 138. The positioning of the fixation ring 138 in the area of the flutes 155 proximal to the apex 158 results in stronger pull-out resistance for base 100, with the resistance increasing further as bone grows into the pores of fixation surface 159 and fixation ring 138.

Figure 4:
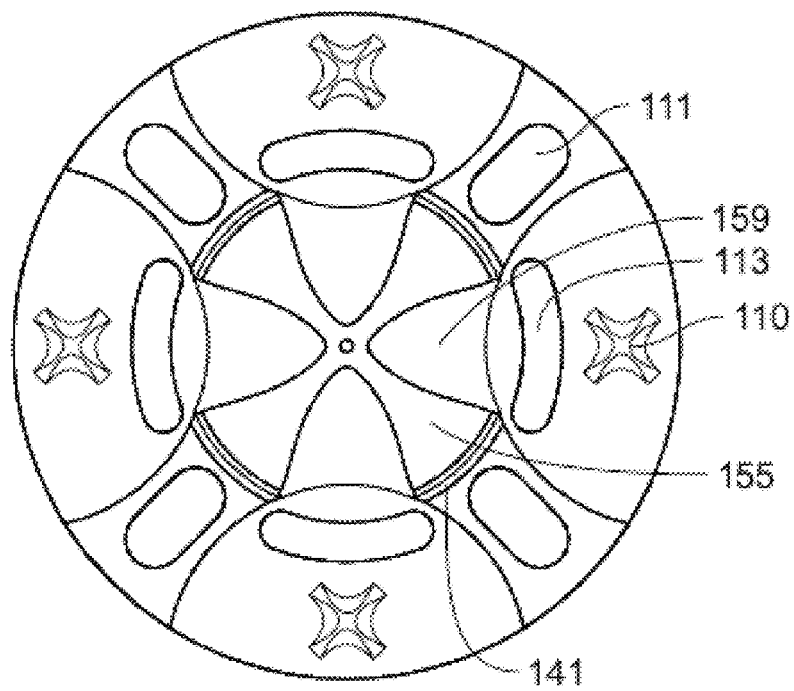
FIG. 4 is a bottom view of the base of FIG. 1.

As shown in FIGS. 3 and 4, collar 101 defines a plurality of holes 111 and 113 extending from proximal end surface 102 to bone-engaging surface 103 and includes a plurality of peripheral anchors or pegs 110 extending distally from bone-engaging surface 103 to distal tips 120. Pegs 110 aid in the fixation of base 100 to the bone, and may particularly assist in initial fixation. While there can be any number of pegs 110 on collar 101, preferably there are four pegs positioned at substantially equal circumferential intervals around the collar. As shown best in FIG. 4, pegs 110 may be located radially outward of holes 113, although other relative spacing between pegs 110 and holes 113 may be appropriate. The use of at least four pegs 110 may provide for enhanced feedback, especially compared to the use of three or fewer pegs, while seating base 100 into the prepared bone during insertion. For example, upon initial contact of pegs 110 with a prepared flat bone surface, the surgeon may be able to easily determine if each of the pegs is simultaneously in contact with the bone. In particular, if all four pegs 110 are in contact with the proximal surface of the bone, the base 100 should not experience any significant amount of rocking or tilting. If the surgeon notices rocking of the base 100, it should be clear that all four pegs 110 are not simultaneously in contact with the bone. If base 100 included three pegs, on the other hand, this rocking motion would not be expected despite a mismatch between a plane defined by the tips of the pegs and a plane of the prepared proximal bone.

As shown in FIG. 3, pegs 110 extend distally from bone-engaging surface 103 to distal tips 120. Pegs 110 may also include flutes 115. Each flute 115 is positioned between two edges 117, and flutes 115 may be generally concave between the two edges 117. Each peg 110 may have a substantially identical structure to central anchor 140 but scaled to a smaller size. Those structures may provide substantially the same effect as the corresponding features on central anchor 140, although the effects may be less dramatic due to the smaller sizes of the pegs compared to the central anchor. However, in other embodiments, the pegs 110 do not need to have identical but scaled down features as the central anchor 140.

As shown in FIGS. 2-4, holes 111 and 113 extend from proximal surface 102 to bone-engaging surface 103. Holes 111 and 113 may be in any shape, round, oval, oblong, etc. Alternatively, holes 111 may be openings extending from proximal surface 102 to bone-engaging surface 103 near side wall 104, such that side wall 104 includes curved recesses in the side wall. In the illustrated embodiment, holes 111 are oblong and a major axis of each hole extends from a point near central anchor 140 radially outwardly toward a point near side flange 104 of collar 101. Holes 113, may also be oblong, and slightly curved so that a major axis of each hole extends in the circumferential direction around central anchor 140. Holes 111 and 113 may have various uses. For example, holes 111 and 113 may be used for passing one or more sutures through to aid in fixation of an object to the base 100. Still further, holes 111 and 113 may be used to engage insertion and/or extraction instrumentation. In the illustrated embodiment, there are four holes 111 and four holes 113, but there may be more or fewer of each of hole 111 and 113. Further, there is no requirement that the number of holes 111 equal the number of holes 113.

In addition to the uses described above, holes 113 may be sized and positioned to facilitate a revision procedure after the base 100 has been implanted into a patient for an amount of time. In the embodiment illustrated in FIG. 3, holes 113 are positioned adjacent fixation surfaces 159 of flutes 155 and fixation ring 138. With this positioning of holes 113, a surgeon may insert a tool through holes 113 in order to chisel, ream, or otherwise cut away at bone that is adjacent to fixation surface 159 and/or fixation ring 138. Strategically cutting away these areas of bone allows for easier removal of base 100 so that a new device may be implanted in its place.

Each hole 111 may be spaced generally midway between two adjacent pegs 110. However, in some embodiments each hole 111 may be positioned adjacent a corresponding peg 110. In such an embodiment, each hole 111 is preferably disposed adjacent a same side of the associated peg 110. In other words, each hole 111 may be disposed on the right side adjacent to each peg 110, or each hole 211 may be disposed on the left side adjacent to each peg. With each hole 111 adjacent the same side of an associated peg 110, a tool inserted through the holes 111 may be used to ream or cut bone adjacent pegs 110, such that the base 100 may be rotated to move the pegs into the bone cavity adjacent the holes 111. This process may allow for easier removal of base 100 during a revision surgery. Rather than having one hole associated with each peg 110, each peg may include two holes on either side of the peg so that the base 100 may be rotated in either direction to facilitate extraction of the base.

Base 100 may further define an opening 130. Opening 130 may extend distally along longitudinal axis 135 from proximal surface 102 of collar 101. Opening 130 may extend partially or fully through anchor 140 along longitudinal axis 135 or it may be shallow and extend only into collar 101. A humeral head component (not shown) may be placed within opening 130 and attached thereto, for example by a taper lock such as a Morse taper. The humeral head component may be attached by any known securement means including screw or friction fit.

It should be understood that base 100 may be formed of any suitable prosthetic grade material, including, for example, titanium alloys and/or other biocompatible metals and metal alloys. In some embodiments of base 100, the porous portions of the base, such as fixation surface 159 and fixation ring 138, may be provided via additive manufacturing over a base material such as titanium alloy. Although one particular type of base 100 of a stemless prosthetic shoulder implant is described above, various other types of prosthetic shoulder implants and corresponding bases may be used in conjunction with the impactors described below. Examples of bases of stemless prosthetic shoulder implants that may be suitable, potentially with minor modification, for use with the impactors described herein may be found in U.S. Patent Publication No. 2018/0271668, the disclosure of which is hereby incorporated by reference herein.

As should be evident, the distally-anchors of stemless prosthetic humeral implants are very short, particularly in comparison to typical stemmed humeral implants. As a result, in stemless prosthetic humeral implants, there is relatively little distal engagement with the bone of the proximal humerus. It may therefore be important that the proximal humeral bone cavity is prepared in a precise manner so as to maintain an appropriate press-fit between the base of the prosthetic humeral implant and the cavity of the proximal humerus.

Typically, when a base of a stemless prosthetic humeral implant, such as base 100, is implanted into the proximal humerus, an impactor is used to physically impact the proximal humerus to create a cavity that matches the shape of the anchor portions of the base, or otherwise connects to the base of the prosthetic humeral implant to drive the anchoring portions of the base into the proximal humerus via impaction. However, current impaction instrumentation does not aid the user in determining that the punch used to create the cavity is being driven perpendicular to the resection plane of the proximal humerus. Also, current impaction instrumentation typically does not aid the user in determining that the base of the prosthetic humeral implant will be driven into the bone perpendicular to the resection plane of the proximal humerus.

In order to try to address these issues, devices and/or methods may include the use of a pilot wire that is inserted perpendicular to the resection plane of the proximal humerus. Impaction instrumentation is then cannulated and engages the pilot wire to help drive the impaction instrument perpendicular to the resection plane of the proximal humerus. However, it has been observed that the pilot wire stability is typically insufficient to prevent off-angle impaction. Furthermore, implants are often not cannulated and implant impaction cannot be guided over the pilot wire in such cases.

Impaction instrumentation may also include a hard stop that will engage with the resection plane of the proximal humerus only after the base of the prosthetic stemless humeral implant (or punch device) has been impacted into the bone. The surgeon must then determine if the hard stop is fully seated against the resection plane to determine if the implant (or punch device) is fully seated and/or perpendicular to the resection plane. However, such an approach typically does not prevent off-angle impaction, at least because by the time the hard stop engages the bone, the impaction is already complete and it is not possible to adjust the implant if it is determined that off-angle impaction occurred.

In order to attain proper initial stability between the base of the prosthetic humeral implant and the proximal humerus, it may be important that the press-fit between the prepared bone cavity and the implant is uniform and controlled. The impactor devices described herein may assist in providing consistent and controlled press-fit between the bone cavity of the proximal humerus and the base of the prosthetic stemless humeral implant, promoting conditions for optimal initial stability.

Figure 5:
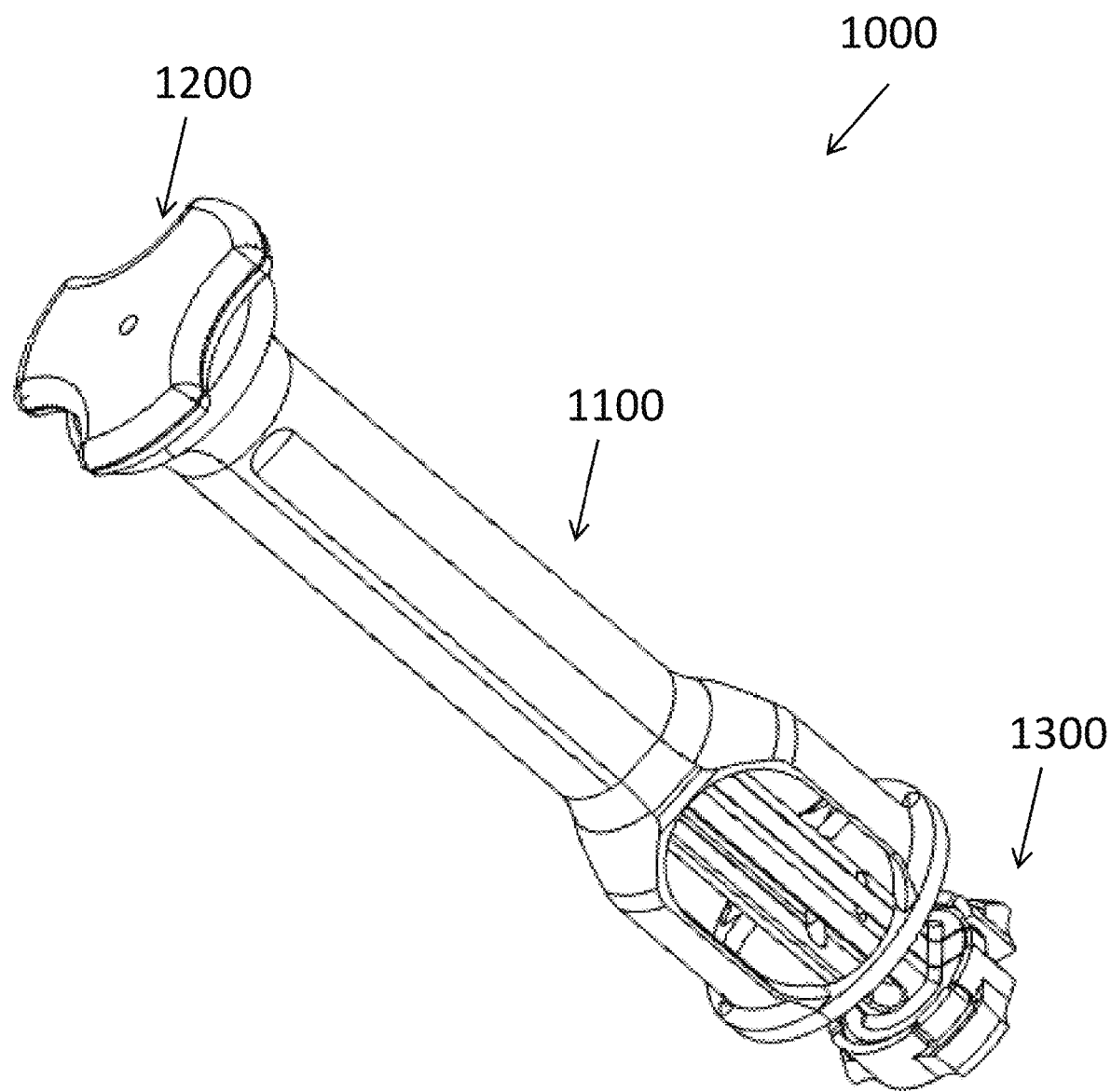
FIGS. 5 and 6 are top and bottom perspective views, respectively, of an impaction system according to an aspect of the disclosure.
Figure 6:
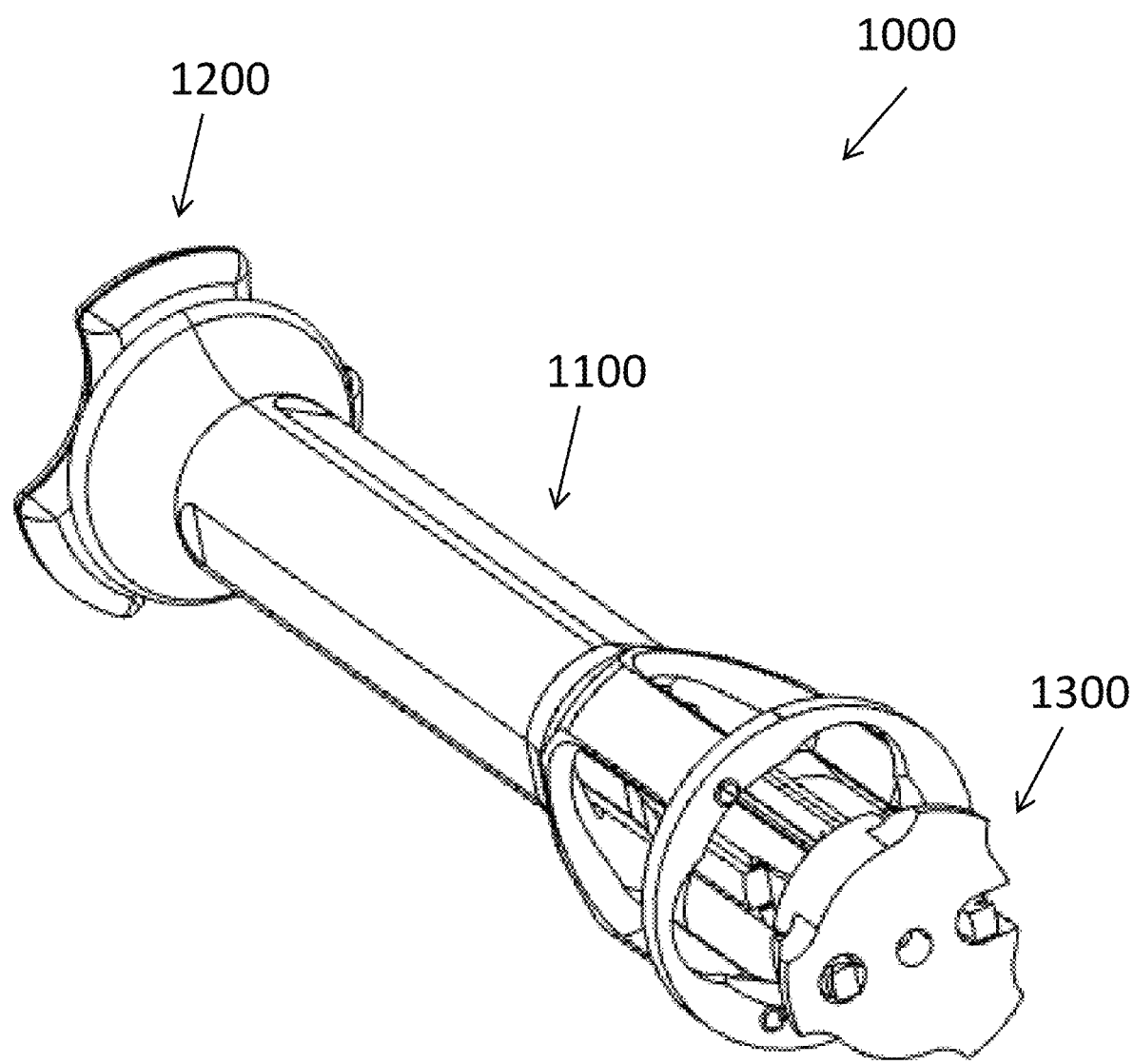

FIGS. 5 and 6 illustrate top and bottom perspective views, respectively, of an impaction system 1000 according to an aspect of the disclosure. FIGS. 5 and 6 illustrate the impaction system 1000 without a base or another component of a prosthetic heart valve coupled to the impaction system. Generally, impaction system 1000 may include a housing 1100, an impaction member 1200, and an impaction tip 1300. Generally, the housing 1100 assists in stabilizing the impaction system 1000 in a desired position prior to impaction, the impaction system 1200 provides the mechanism by which an impaction force is transferred to the implant, and the impaction tip 1300, if used, assists in evenly distributing force from the impaction member 1200 to the implant.

Figure 7:
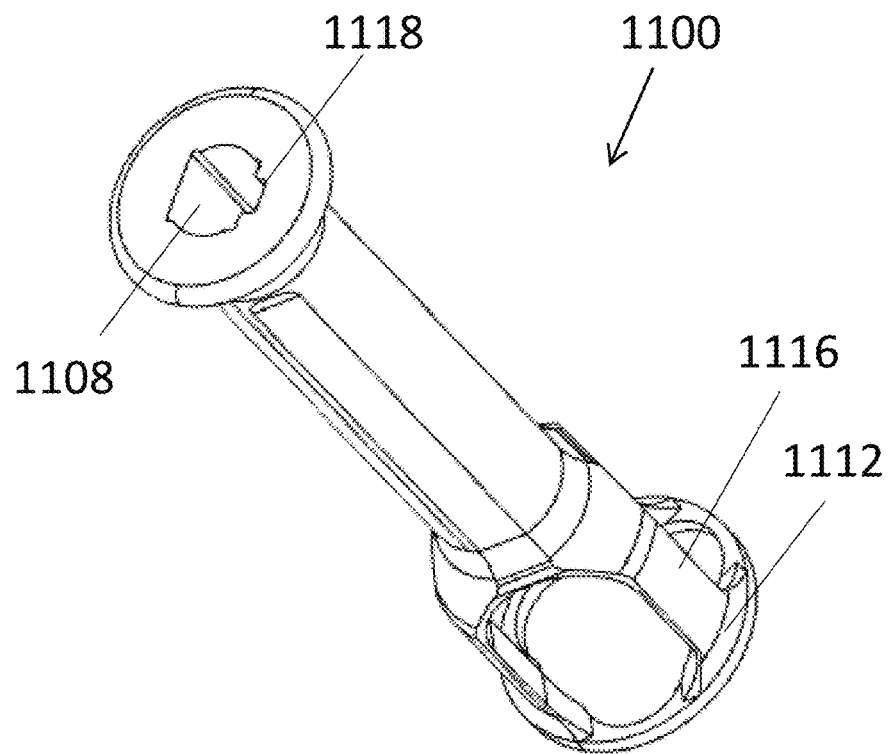
FIGS. 7 and 8 are top and bottom perspective views, respectively, of a housing of the impaction system of FIGS. 5 and 6.
Figure 8:
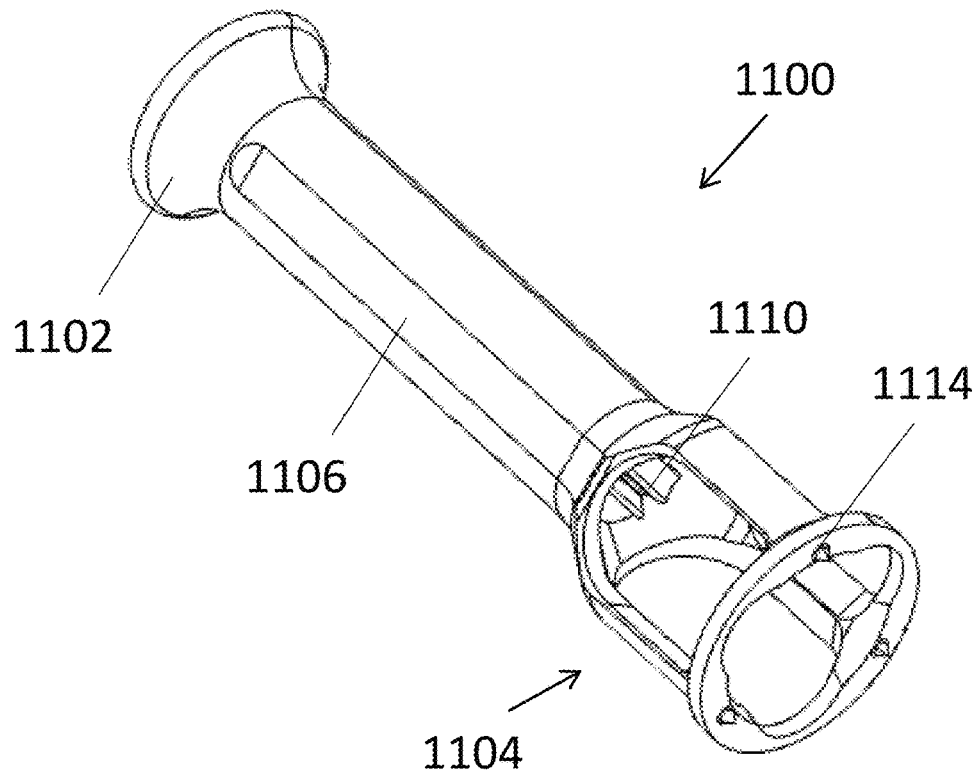

FIGS. 7 and 8 are top and bottom perspective views, respectively, of the housing 1100 of impaction system 1000. Housing 1100 includes a proximal flange 1102, a distal stabilizer 1104, and a shaft 1106 connecting the flange to the stabilizer. Flange 1102 may be substantially circular and have a diameter larger than shaft 1106, and may be adapted to contact an impactor handle 1204 of impaction member 1200. Flange 1102 may also include an aperture 1108 therein. Aperture 1108 may define a first end of a channel extending through shaft 1106, with a distal end of the channel ending in an aperture 1110 in the shaft 1106. The apertures 1108, 1110 may be sized and shaped to receive portions of impaction member 1200 therethrough so that the impaction member 1200 is slideable along the central longitudinal axis of the housing 1100. Stabilizer 1104 may extend from the distal end of shaft 1106 and include a rim 1112. In the illustrated embodiment, rim 1112 is substantially circular and defines a central opening. The distal surface of rim 1112 is preferably substantially flat so that, upon contact of rim 1112 with a planar surface, such as the resection plane of a proximal humerus, the central longitudinal axis of the impaction system 1000 is orthogonal or substantially orthogonal with respect to the distal surface of rim 1112 and the resection plane of the proximal humerus. The central opening defined by rim 1112 is preferably sized and shaped to allow impaction tip 1300, if used, and a base of a prosthetic humeral implant coupled to the impaction system 1000 to be driven through the central opening of the rim 1112.

As best seen in FIG. 8, the distal surface of rim 1112 may include one or more spikes 1114 or other engagement features. In the illustrated embodiment, rim 1112 includes three spikes 1114 positioned at substantially equal intervals around the circumference of the rim 1112, although it should be understood that more or fewer spikes 1114 may be suitable in other embodiments. Spikes 1114 may assist in maintaining the placement of the housing 1100 of the impaction system 1000 in a desired position after initially placing the impaction system 1000 on the proximal humerus, and during the process of impacting the base of the prosthetic stemless humeral implant into the proximal humerus, so that the position of the housing 1100 does not change. It should be understood that although spikes 1114 or other similar engagement features are desired, they may be omitted in come embodiments. Still further, other friction-enhancing features may be provided on the distal surface of rim 1112 other than, or in addition to, spikes 1114, such as a roughened surface.

In the illustrated embodiment, housing 1100 includes a plurality of extensions 1116 connecting the distal end of the shaft 1106 to the stabilizer 1104. Although three extension members 1116 are shown, more or fewer may be provided. And while openings are provided between circumferentially adjacent extension members 1116, the openings may not be necessary and a single solid extension member 1116 may be provided to connect the rim 1112 to the shaft 1106. However, it may be preferable to maintain openings between the plurality of extension members 1116 to (i) reduce the material of housing 1100 to reduce weight and manufacturing costs and/or (ii) provide visibility of the components positioned within stabilizer 1104, although such components are omitted from FIGS. 7 and 8.

Figure 9:
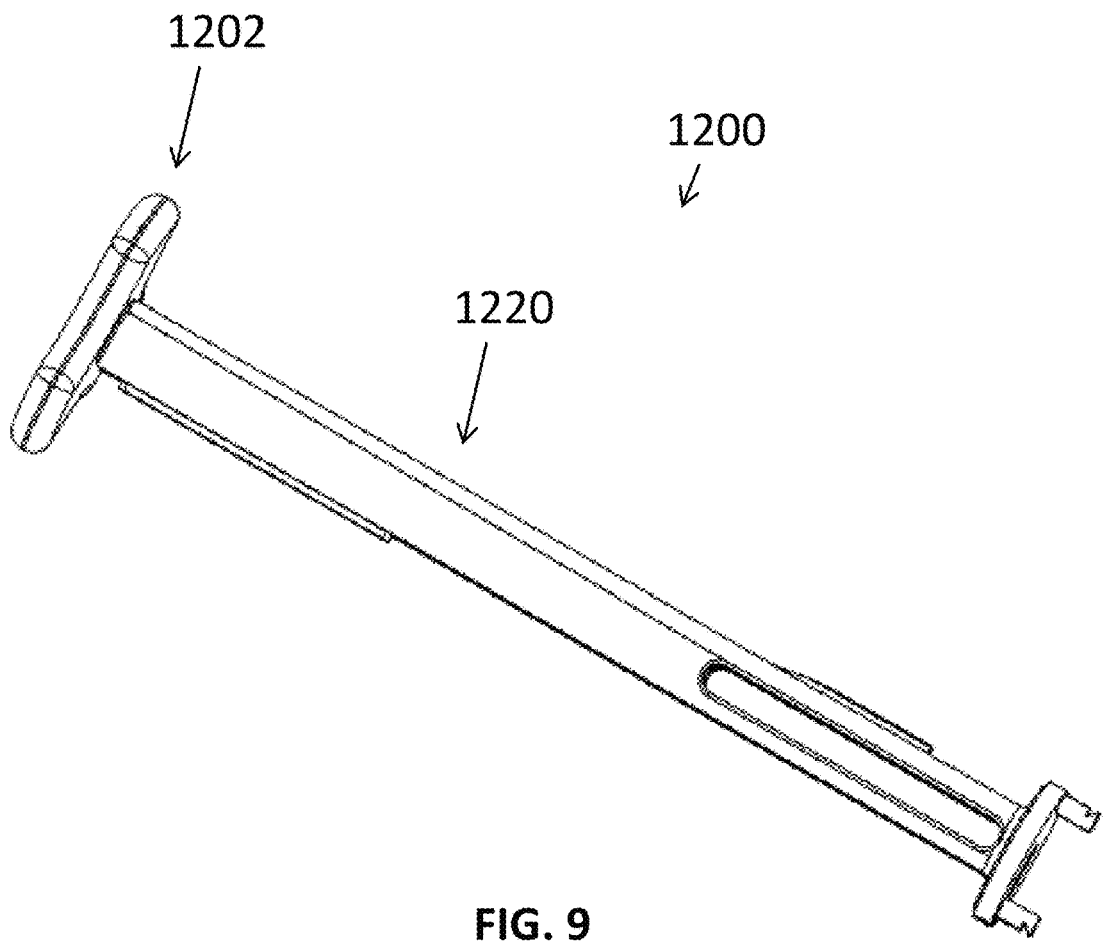
FIG. 9 is a perspective view of an impaction member of the impaction system of FIGS. 5 and 6.

FIG. 9 is a perspective view of the impaction member 1200. A proximal end of the impaction member 1200 is adapted to be impacted to drive a distal end of the impaction member 1200, and in particular a base of the prosthetic stemless humeral implant coupled to the distal end of the impaction member 1200, into the bone of the proximal humerus. As will be described below, the impaction member 1200 is slidably coupled to the housing 1110 so that, when the housing 1100 is in the desired position against the resection plane of the proximal humerus, impacting the impaction member 1200 will drive the impaction member 1200 along the central longitudinal axis of the impaction system 1000, which in the desired position is orthogonal or substantially orthogonal to the resection plane of the proximal humerus. Impaction member 1200 may be formed of two pieces, including handle portion 1202 and a shaft portion 1220.

Figure 10:
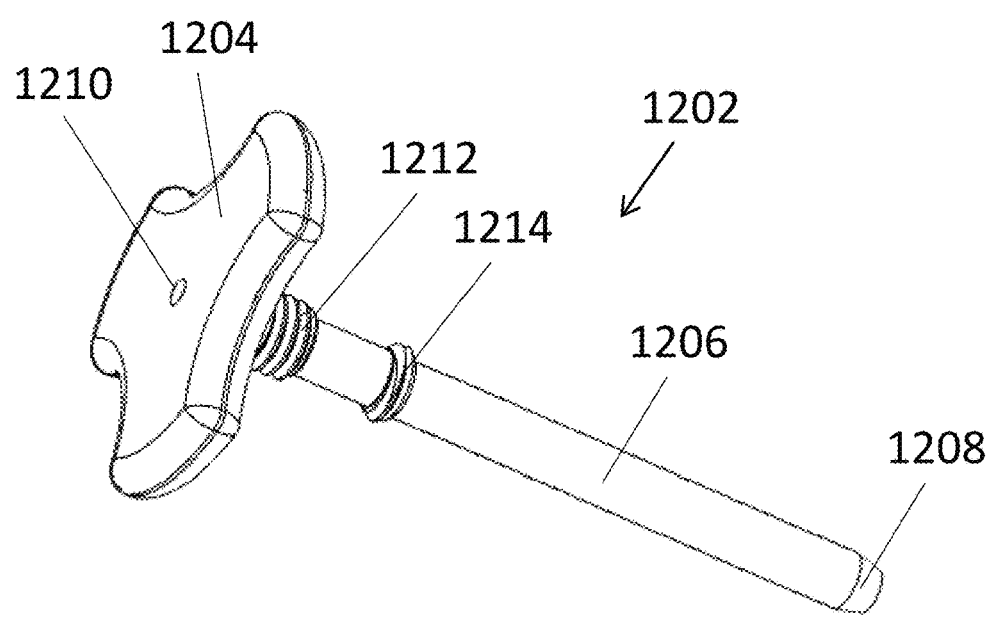
FIG. 10 is a perspective view of a handle portion of the impaction member of FIG. 9.

FIG. 10 is a perspective view of the handle portion 1202 of the impaction member 1200. The proximal end of the handle portion 1202 may include a handle 1204 at a proximal end thereof. Preferably, handle 1204 includes a relatively large flat surface conducive to being impacted, for example by a mallet or a hammer device. In the illustrated example, handle 1204 is contoured to assist a user in turning handle 1204, and thus handle portion 1202, as described below. Handle portion 1202 may include a shaft 1206 extending distally from a center of handle 1204, terminating in a distal tip 1208, which may be tapered to a smaller diameter than the shaft 1206. A pilot wire channel 1210 may extend partially or completely through the handle portion 1202, which may be sized and shaped to receive a pilot wire therethrough. If a pilot wire is used, as is described in greater detail below, it may be temporarily implanted into the proximal humerus to guide the impaction system 1000, along with a prosthetic stemless humeral implant attached thereto, into a desired position and orientation with respect to the resection plane of the proximal humerus. Shaft 1206 may include a first thread 1212 near or adjacent the proximal end of the shaft 1206, and a second thread 1214 (which may be referred to as a capture thread) positioned a spaced distance along the shaft 1206 form the first thread 1212. As described below, the first thread 1212 may engage a corresponding thread 1224 in shaft portion 1220 of impaction member 1200 so that, upon rotation of handle 1204, the handle portion 1202 is driven distally into the shaft portion 1220 to cause the impaction member 1200 to lock onto the base of the prosthetic stemless humeral implant. The second thread 1214 may be used to help retain the shaft 1206 within shaft portion 1220. The shaft portion 1220 may include additional corresponding threads and/or undercuts on the interior diameter thereof that may be used to retain the second thread 1214. This interaction may help prevent the shaft 1206 from slipping out of shaft portion 1220 if the first thread 1212 becomes disengaged from their corresponding threads 1224.

Figure 11:
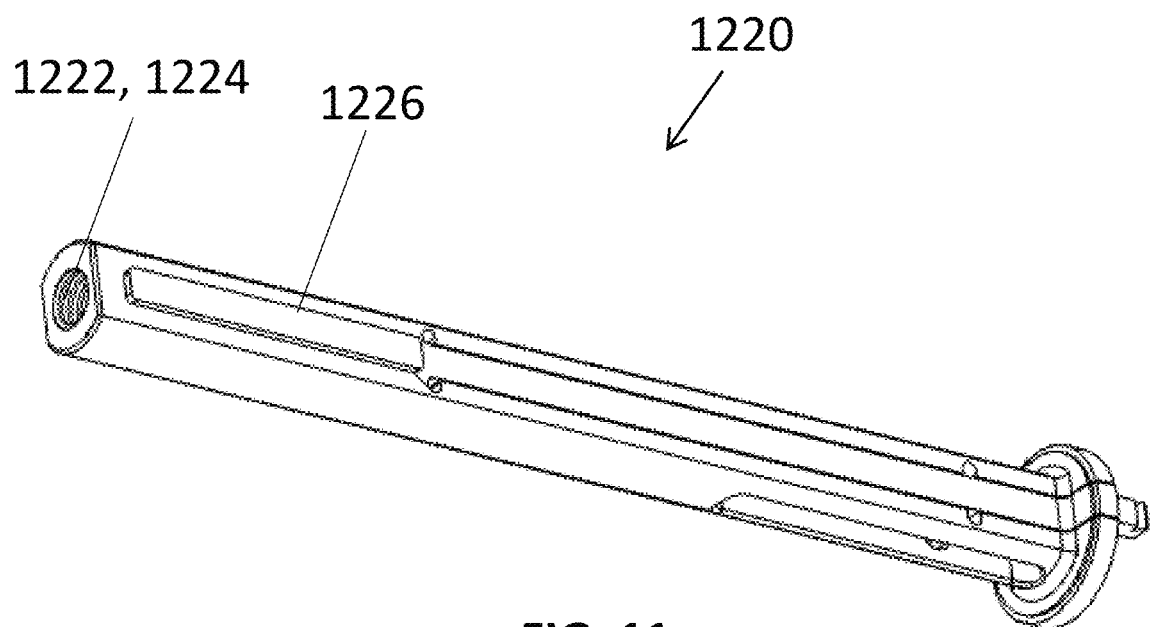
FIGS. 11-14 are various perspective views of a shaft portion of the impaction member of FIG. 9.

FIGS. 11-14 are various perspective views of shaft portion 1220 of impaction member 1200 at different rotational positions along the longitudinal axis of the shaft portion 1220. The proximal end of shaft portion 1220 may include an opening 1222 through which the handle portion 1202 may be inserted, and opening 1222 may include threading 1224 complementary to the first thread 1212 of the handle portion 1202. The portions of the shaft portion 1220 that are received within the shaft 1106 housing 1100 preferably have a non-circular profile or other features to prevent rotation of the shaft portion 1220 while it is received within the housing 1100. For example, in the illustrated embodiment, shaft portion 1220 includes two generally flat opposing surfaces connected by two generally rounded portions. Referring to FIG. 11, one of the flat portions may include a protruding track 1226 along a length thereof. Track 1226 may be configured to be received in a corresponding track recess 1118 in housing 1100, as shown in FIG. 7. The protruding track 1226 may function to assist the impaction member 1200 in sliding within housing 1100.

Figure 12:
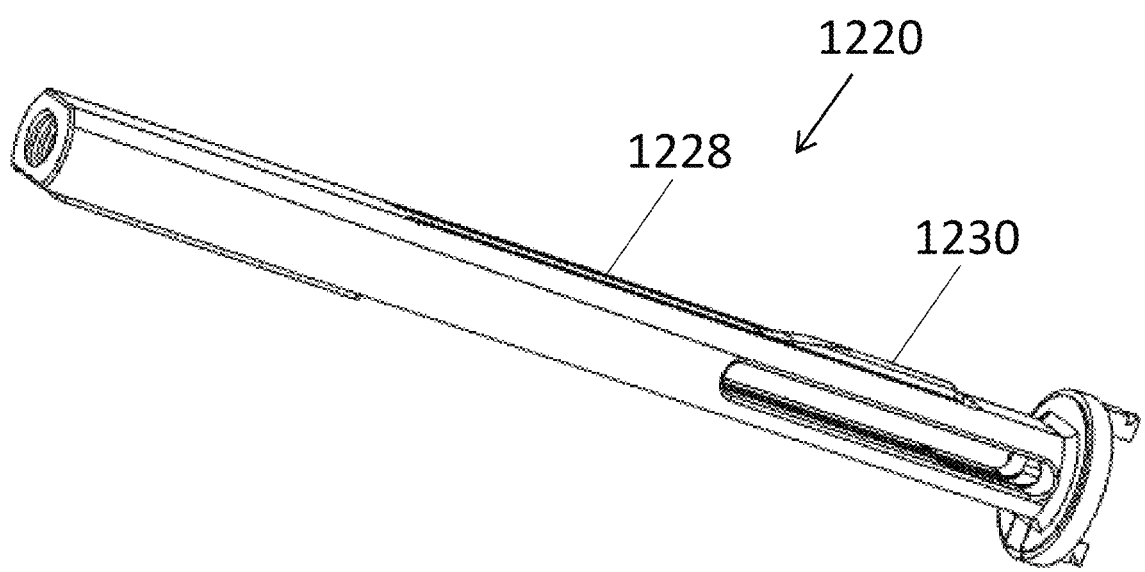
Figure 13:
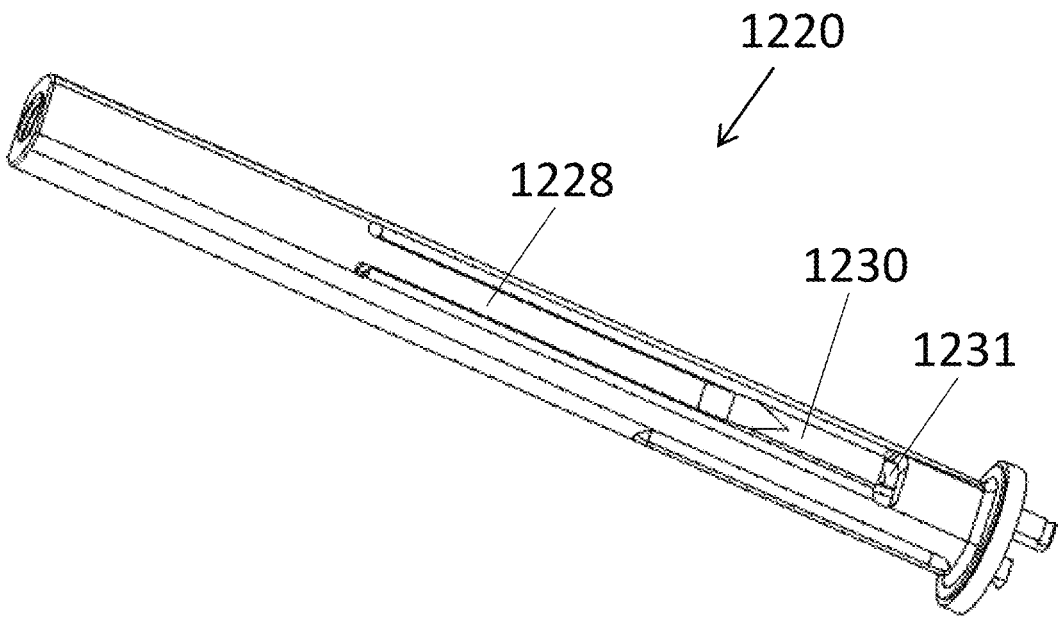

Referring to FIGS. 12-13, shaft portion 1220 may include a flexure member 1228. As best shown in FIG. 13, flexure member 1228 may extend along the flat surface of the shaft portion 1220 opposite the flat surface that includes the protruding track 1226. Flexure member 1228 may be formed by cutting or otherwise forming slots on opposite sides of the flexure member 1228, each of the slots extending distally to an opening 1231. With this configuration, although flexure member 1228 is integral with shaft portion 1220, flexure member 1228 is capable of flexing as the flexure member 1228 is only attached to the shaft portion 1220 at a proximal end of the flexure member 1228. A distal end of the flexure member 1228 may be formed with friction bump-out 1230. The friction bump-out 130 may be a portion of increased thickness or otherwise include a portion that extends beyond the flat surface in which the flexure member 1228 is formed, as best seen in FIG. 12. Referring again to FIG. 7, the aperture 1108 in housing 1100 may be sized and shaped to closely match the profile of the shaft portion 1220, not including the bump-out 1230. As a result, when the shaft portion 1220 is received within the housing 1100, the bump-out 1230 is deflected radially inwardly with respect to the shaft portion 1220, resulting in friction that tends to resist sliding between the shaft portion 1220 and the housing 1100. The friction may be sufficient to inhibit the shaft portion 1220 from freely sliding with respect to housing 1100, but not be so great as to make intentional movement of the shaft portion 1220 relative to the housing 1100. In other words, the bump-out 1230 of the flexure member 1228 is configured such that, gravity or other relatively small forces will not result in the shaft portion 1220 sliding relative to the housing 1100. However, upon impaction or other intentional movement of the shaft member 1220, as described in greater detail below, the bump-out 1230 of the flexure member 1228 will not hinder the desired movement.

Figure 14:
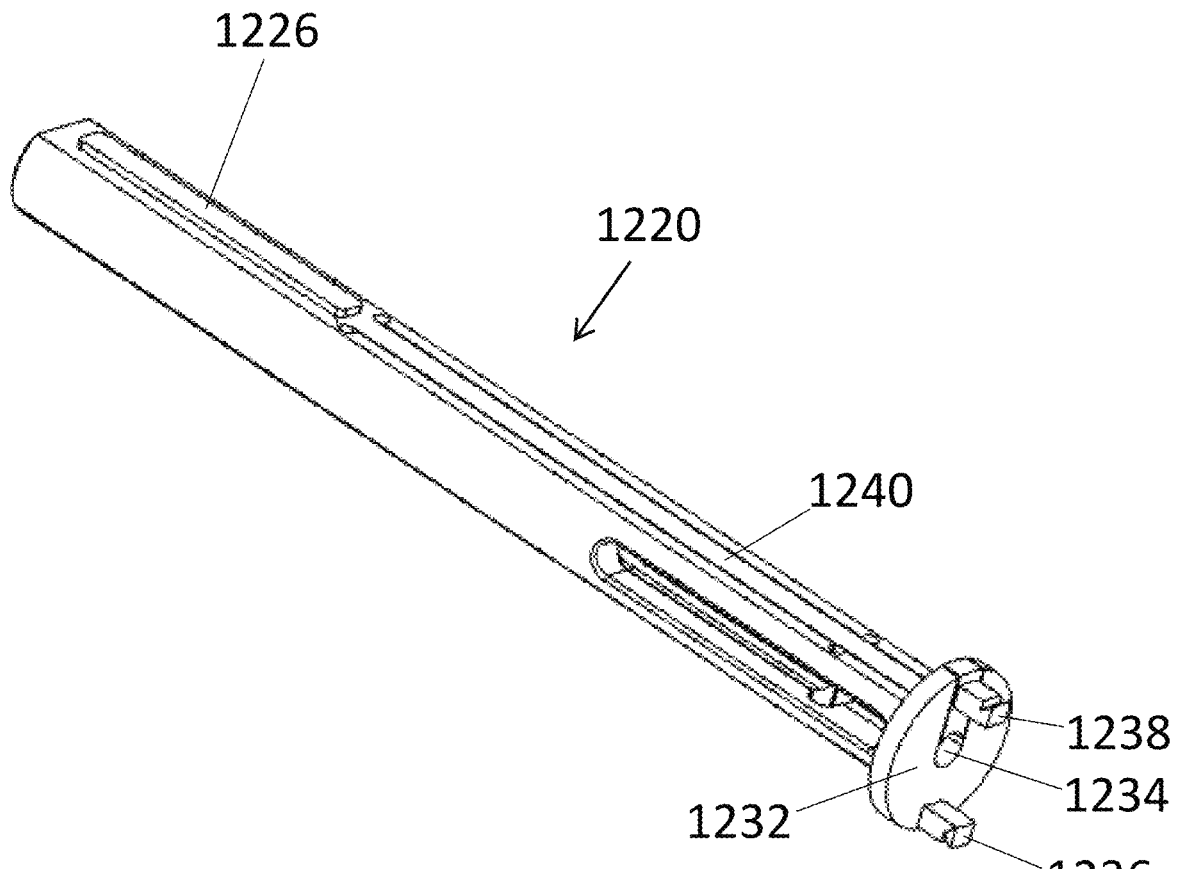

The distal end of shaft portion 1220 may include a generally circular distal flange 1232, as best seen in FIG. 14. Flange 1232 may include a central aperture 1234 so that the pilot wire described above may pass through the shaft portion 1220. A first finger 1236 may extend from a distal end of the flange 1232 on a first side of aperture 1234. Preferably, first finger 1236 is monolithic with, or otherwise fixed to or immobile with respect to the flange 1232. First finger 1236 may include a hooked end hooking away from the center of the flange 1236, or another geometry adapted to hook into a corresponding mating recess of the base of the prosthetic stemless humeral implant, described in greater detail below. A second finger 1238 may extend from the distal end of the flange 1232 on a second side of aperture 1234 opposite the first finger 1236. Second finger 1238 may be shaped similarly to first finger 1236, for example with a hooked end hooking away from the center of flange 1236, or another geometry adapted to hook into a corresponding mating recess of the base of the prosthetic stemless humeral implant. However, second finger 1238 is preferably mobile with respect to the flange 1232. In particular, as shown in FIG. 14, second finger 1238 may be positioned at a distal end of a second flexure member 1240. Similar to flexure member 1228, second flexure member 1240 may be formed between two slots formed in the flat surface of the shaft portion 1220, the two slots extending to the terminal distal end of the shaft portion 1220. With this configuration, the second flexure member 1240 is capable of being forced radially away from the center longitudinal axis of the shaft member 1220, with movement of the second flexure member 1240 causing corresponding movement of the second finger 1238.

Figure 15:
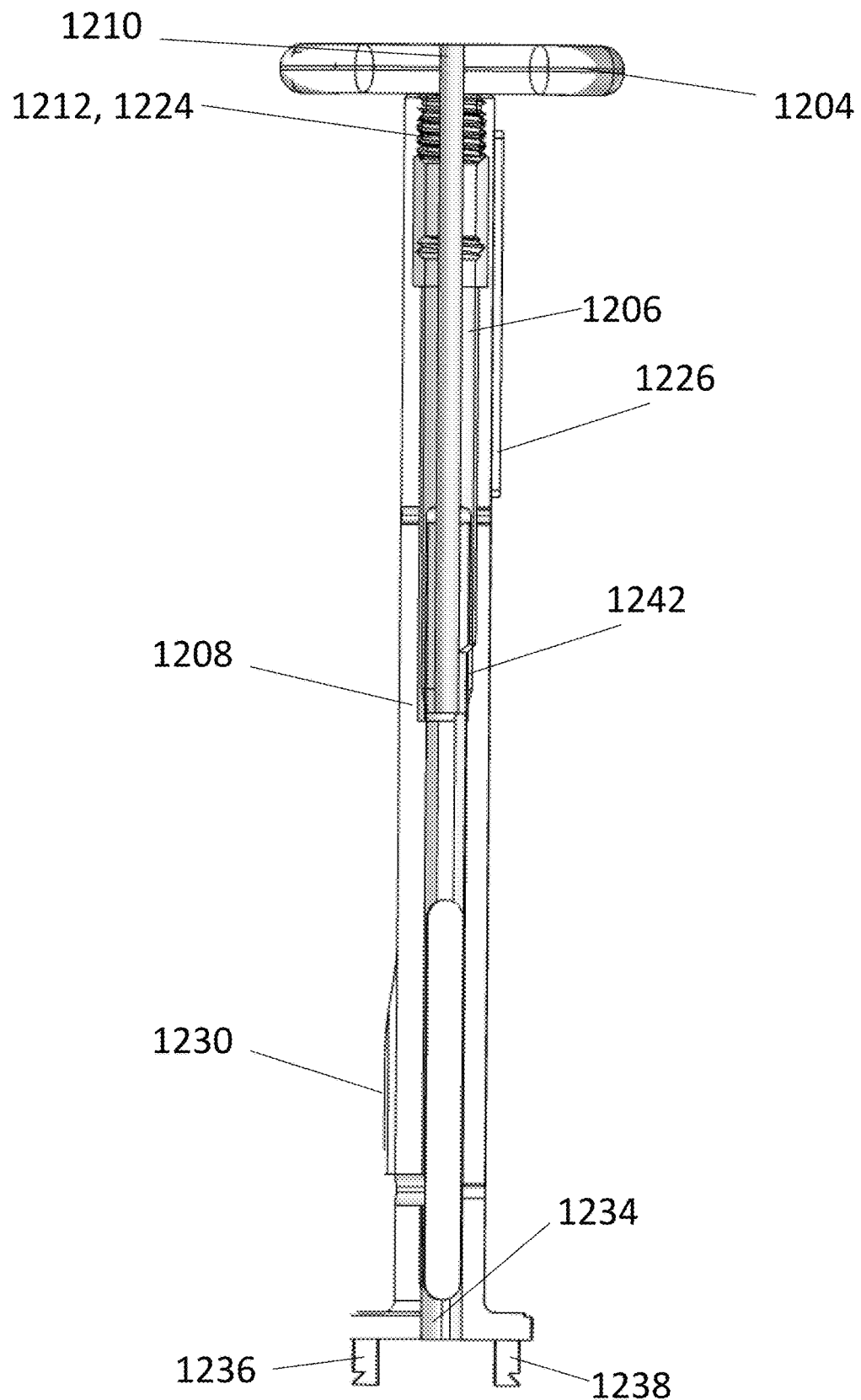
FIG. 15 is a cross-section of the handle portion and the shaft portion of the impaction member of FIG. 9 in the assembled condition.

FIG. 15 is a cross-section of the handle portion 1202 and the shaft portion 1220 of the impaction member of FIG. 9 in the assembled condition. When the handle portion 1220 is received within the shaft portion 1220, as noted above, turning handle 1204 to engage threads 1212 with threads 1224 will cause the shaft 1206 of the handle portion 1202 to advance distally (or retract proximally), depending on the direction of rotation. The shaft 1206 of handle portion 1202 is received within a passageway defined by the shaft portion 1220 of the impaction member 1200. As can be seen in FIG. 15, an interior surface of the shaft portion 1220 defining the passageway may define a shoulder 1242 that extends radially inwardly toward the center of the longitudinal axis of the impaction member 1200 generally near the proximal-to-distal center of the impaction member 1200. Preferably, the shoulder 1242 is defined on the interior of a portion of the flexure member 1240, which is also the side of the shaft portion 1220 that includes the second finger 1238 which is the mobile finger 1238. The inner diameter of the passageway in the shaft portion 1220 is generally about equal to the outer diameter of the shaft 1206 of the handle portion 1202. However, at the location of the shoulder 1242, the inner diameter of the passageway in the shaft portion 1220 decreases to a value that is less than the outer diameter of the shaft 1206 of the handle portion 1202. As a user rotates knob 1204 to drive the shaft 1206 distally, the tip 1208 of the shaft 1206 contacts the shoulder 1242 as it drives distally. If the tip 1208 includes a taper, the taper may assist in forcing the flexure member 1240 to splay radially outwardly as the shaft 1206 contacts the shoulder 1242. As a result, as the flexure member 1240 splays radially outwardly, the second finger 1238 which is attached to the flexure member 1240 splays radially outwardly, increasing the distance between first finger 1236 and second finger 1238. In other words, in a first proximal position of the handle portion 1202, there is a first relatively small distance between the first and second fingers 1236, 1238. In a second distal position of the handle portion 1202, there is a second relatively large distance between the first and second fingers 1236, 1238. As is explained in more detail below, the fingers 1236, 1238 may be inserted into corresponding mating recesses of a base of a prosthetic stemless humeral implant while the handle portion 1202 is in the first proximal position, and by transition the handle portion 1202 to the second distal position, the outward relative splaying between the first and second fingers 1236, 1238 can lock or otherwise secure the base of the prosthetic stemless humeral implant to the impaction member 1200 in preparation for impaction.

Figure 16:
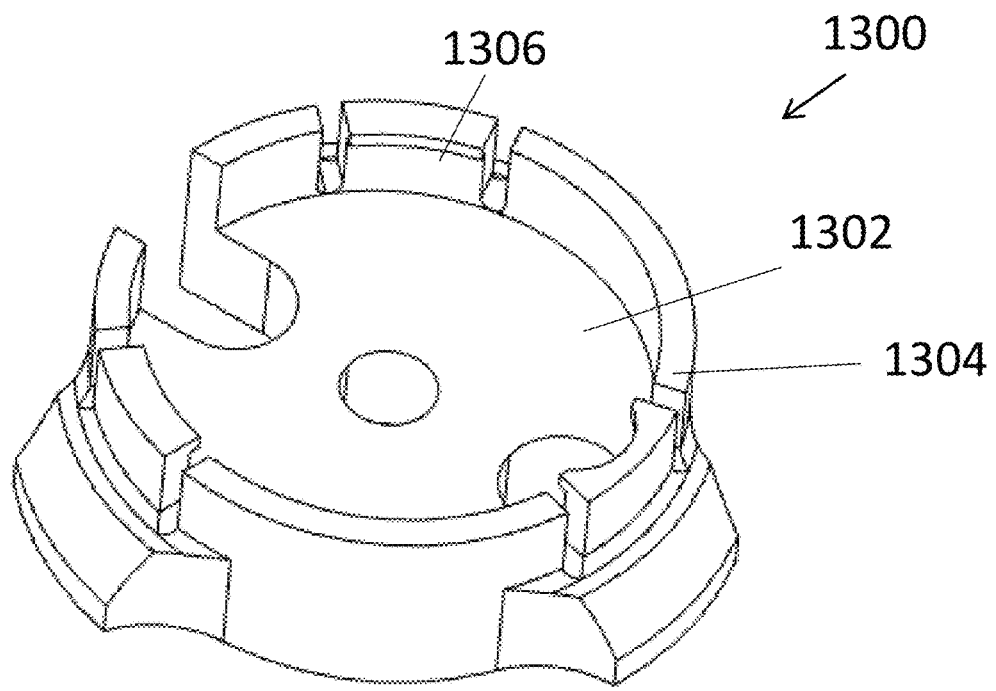
FIGS. 16 and 17 are top and bottom perspective views, respectively, of an impaction tip of the impaction system of FIGS. 5 and 6.
Figure 17:
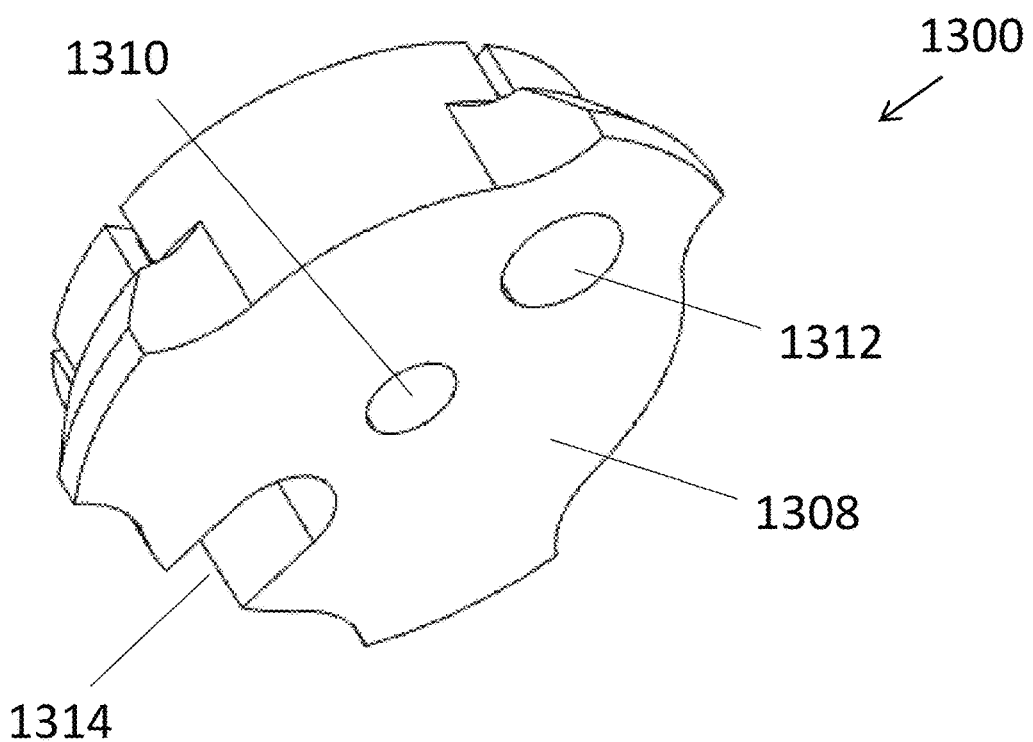
Figure 18:
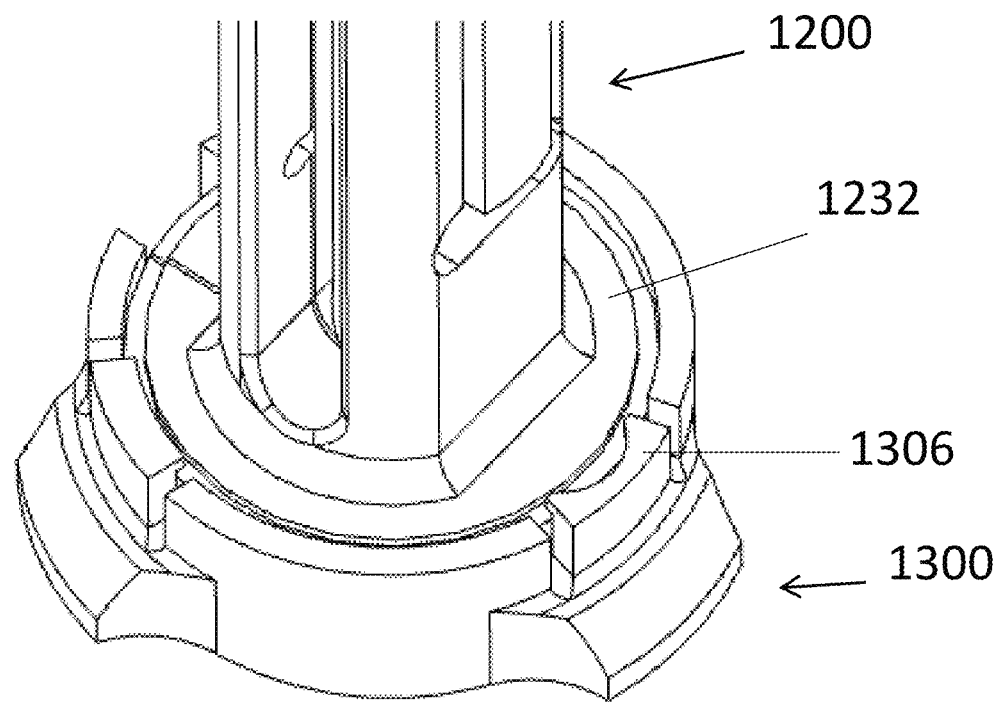
FIGS. 18 and 19 are enlarged top and bottom perspective views, respectively, of the impaction tip of FIGS. 16 and 17 coupled to the impaction member of FIG. 9.

FIGS. 16 and 17 are top and bottom perspective views, respectively, of impaction tip 1300. Although impaction tip 1300 could be omitted in certain embodiments, it is preferable to include because it assists in evenly transmitting forces from the strike of impaction to the base of the prosthetic stemless humeral implant. Impaction tip 1300 may also include a plurality of extension members extending radially outward therefrom. In the illustrated embodiment, impaction tip 1300 includes three of these extension members (not separately labeled), although fewer or more may be provided. These extension members may engage the harder and denser cortical shell of the proximal humerus upon impaction. These extension members may thus act as a hard stop during impaction, ultimately setting the depth of the implant/punch/broach. It would also be good to point out here that the (3x) extensions that protrude past the inner diameter of this impaction tip do so in order to engage with the harder cortical shell of the proximal humerus. Referring to FIG. 16, impaction tip 1300 includes a substantially planar proximal surface 1302 that is sized and shaped to contact the distal surface of the flange 1232 of impaction member 1200. The proximal surface 1302 may be partially bounded by a generally circular rim 1304 extending proximally from the proximal surface 1302, the rim 1304 adapted to overlie side portions of the flange 1232 of impaction member 1200. A plurality of tabs 1306 may be interrupt the rim 1304 along its circumference. Tabs 1306 may have proximal lips that extend radially inwardly farther than the remainder of rim 1304, and may have an amount of flexibility. When the flange 1232 of impaction member 1200 is inserted into impaction tip 1300, the tabs 1306 may flex and when the flange 1232 is fully seated against proximal surface 1302, the lips of the tabs 1306 may snap back to engage or otherwise lock the impaction tip 1300 to the impaction member 1200, as shown in FIG. 18.

Figure 19:
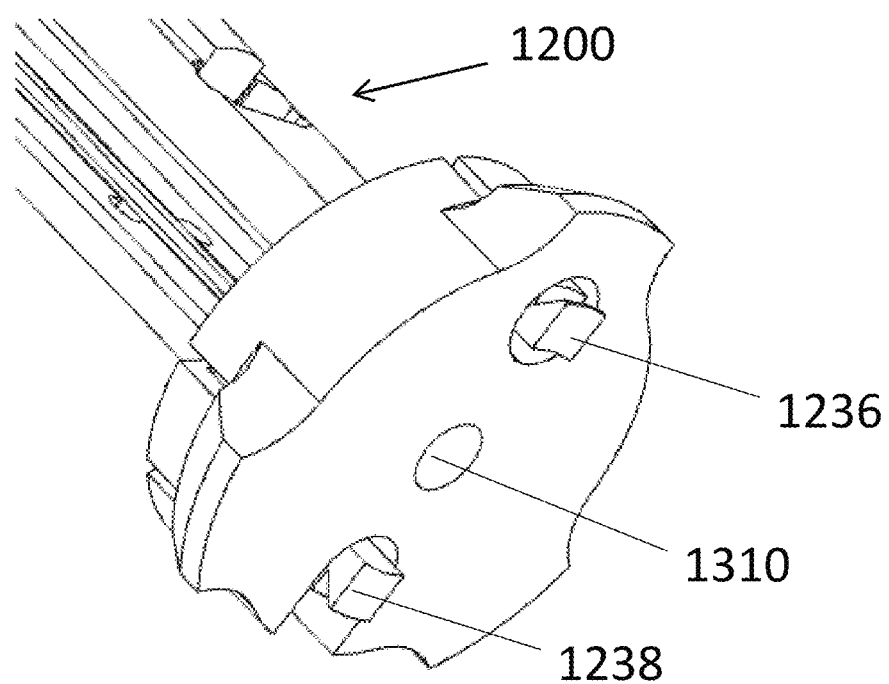

Referring to FIG. 17, impaction tip 1300 includes a substantially planar distal surface 1308 that is sized and shaped to contact the proximal surface of a base of a prosthetic stemless humeral implant, which may be similar to base 100. Impaction tip 1300 may include a pilot wire aperture 1310 at a longitudinal center thereof, the pilot wire aperture 1310 leading to a pilot wire passageway that is sized and shaped to receive a pilot wire therethrough. The impaction tip 1300 may include an aperture 1312 adapted to receive a portion of the first finger 1236 therethrough, so that at least the hook portion of the first finger 1236 projects beyond the distal surface 1308. The impaction tip 1300 may include a slot 1314 to receive a portion of the second finger 1238 therein, so that at least the hook portion of the second finger 1238 projects beyond the distal surface 1308. Aperture 1312 may be closed since first finger 1236 is immobile, but slot 1314 may have an open side to allow the second finger 1238 to splay radially outwardly as the knob 1204 of the impaction member 1200 is rotated. FIG. 19 illustrates the distal surface of the impaction tip 1300 when the impaction member 1200 is coupled to the impaction tip 1300. The hooked portions of the first and second fingers 1236, 1238 are visible, and it should be understood that pilot wire aperture 1310 aligns with the central aperture 1234 in flange 1232 so that a pilot wire may extend through the center of the impaction tip 1300 and continue through the center of the impaction member 1200. As should be understood, the relatively large area of contact provided between the distal planar surface 1308 of the impaction tip 1300 and the proximal surface of the base of the prosthetic stemless humeral implant may assist in suitably transferring forces from the impaction of handle 1204 to the base of the prosthetic stemless humeral implant, without creating undue stress at other points of contact such as the first and second fingers 1236, 1238.

Figure 20:
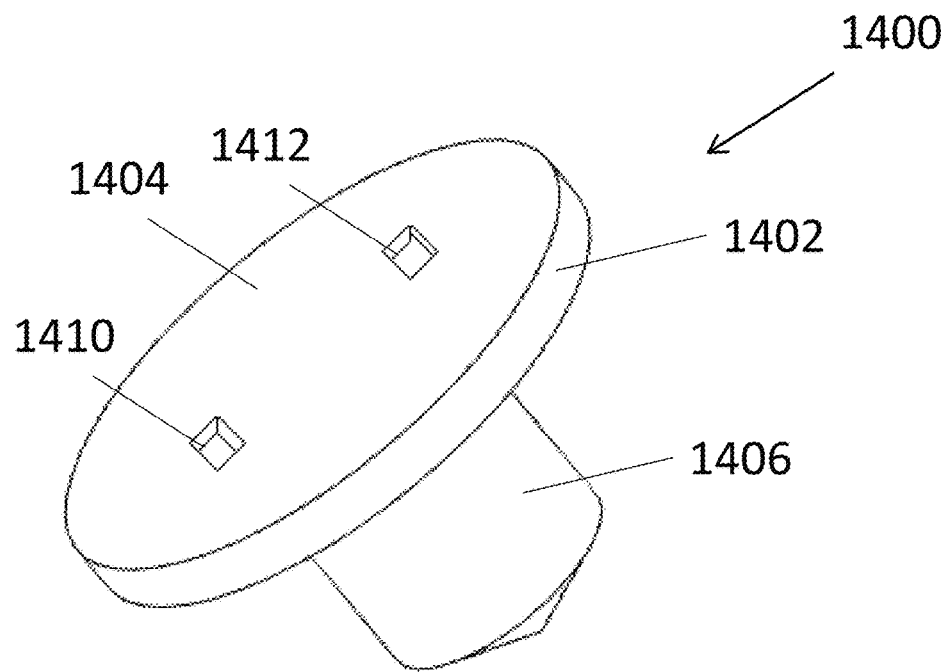
FIGS. 20 and 21 are top and bottom perspective views, respectively, of a base of a prosthetic stemless humeral implant.
Figure 21:
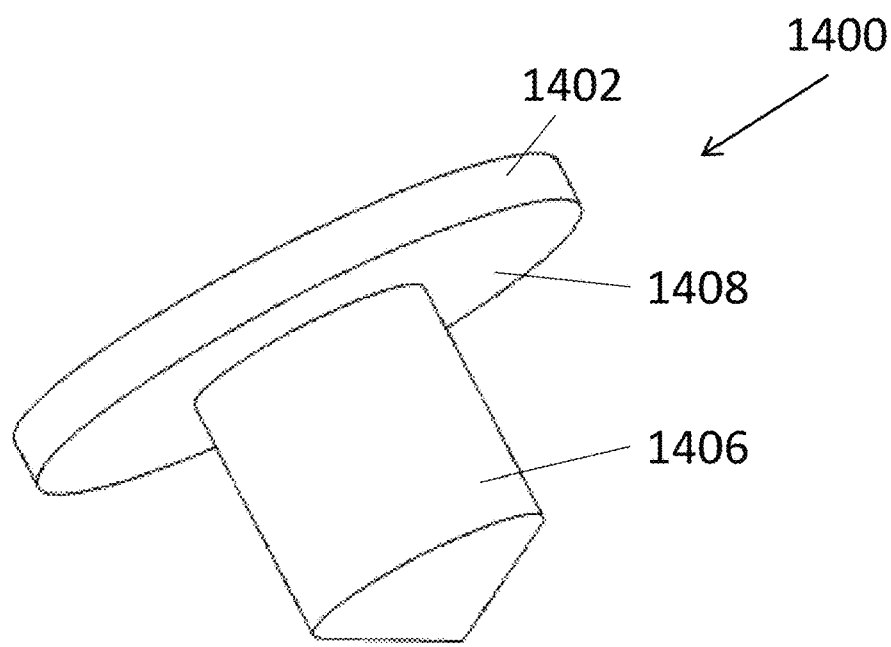

FIGS. 20 and 21 are top and bottom perspective views, respectively, of a base 1400 of a prosthetic stemless humeral implant. It should be understood that base 1400 is illustrated in a highly simplified manner in order to illustrate feature of the base 1400 that couple to corresponding features of the impaction system 1000. Otherwise, it should be understood that base 1400 may include any of the features described in connection with base 100, and thus similar features of base 1400 are not described in greater detail. Generally, base 1400 includes a collar 1402 with a proximal surface 1404, and an anchor 1406 extending from a distal surface 1408 of the collar 1402. The proximal surface 1404 of collar 1402 may include first and second apertures 1410, 1412 sized and shaped to receive first and second fingers 1236, 1238 therein. The structures defining first and second aperture 1410, 1412 may be substantially identical so that either aperture 1410, 1412 may receive either finger 1236, 1238. However, in some embodiments, the first and second aperture 1410, 1412 may only fit fingers 1236, 1238 in a single orientation so that the base 1400 is always in a specific, pre-defined rotational orientation when coupled to the impaction system 1000. The apertures 1410, 1412 may each include a lip, undercut, or similar feature on a surface closer to the outer radial rim of the collar 1402, the lips being sized and shaped to mate with the hooked portions of the fingers 1236, 1238. It should be understood that base 100 may be modified to include apertures similar to apertures 1410, 1412 described in connection with base 1400. Alternately, any pair of opposing apertures 111 or 113 shown and described in connection with base 100 in FIG. 2 may be slightly modified to include features similar to those of apertures 1410, 1412, so that base 100 could be used with impaction system 1000 in the same or similar fashion as described in connection with base 1400. Further, it should be understood that although neither base 100 nor base 1400 are illustrated with a cannulation to receive a pilot wire therethrough, either base may include a cannulation extending along the longitudinal center of the base from the proximal surface 1404 of the proximal collar 1402 through the distal tip of the anchor 1406, the cannulation being sized and shaped to receive the pilot wire therethrough, with the proximal opening of the cannulation in the proximal collar 1402 being aligned with the pilot wire aperture 1310 in the impaction tip 1300 when the base 1400 is coupled to the impaction tip 1300.

Figure 22:
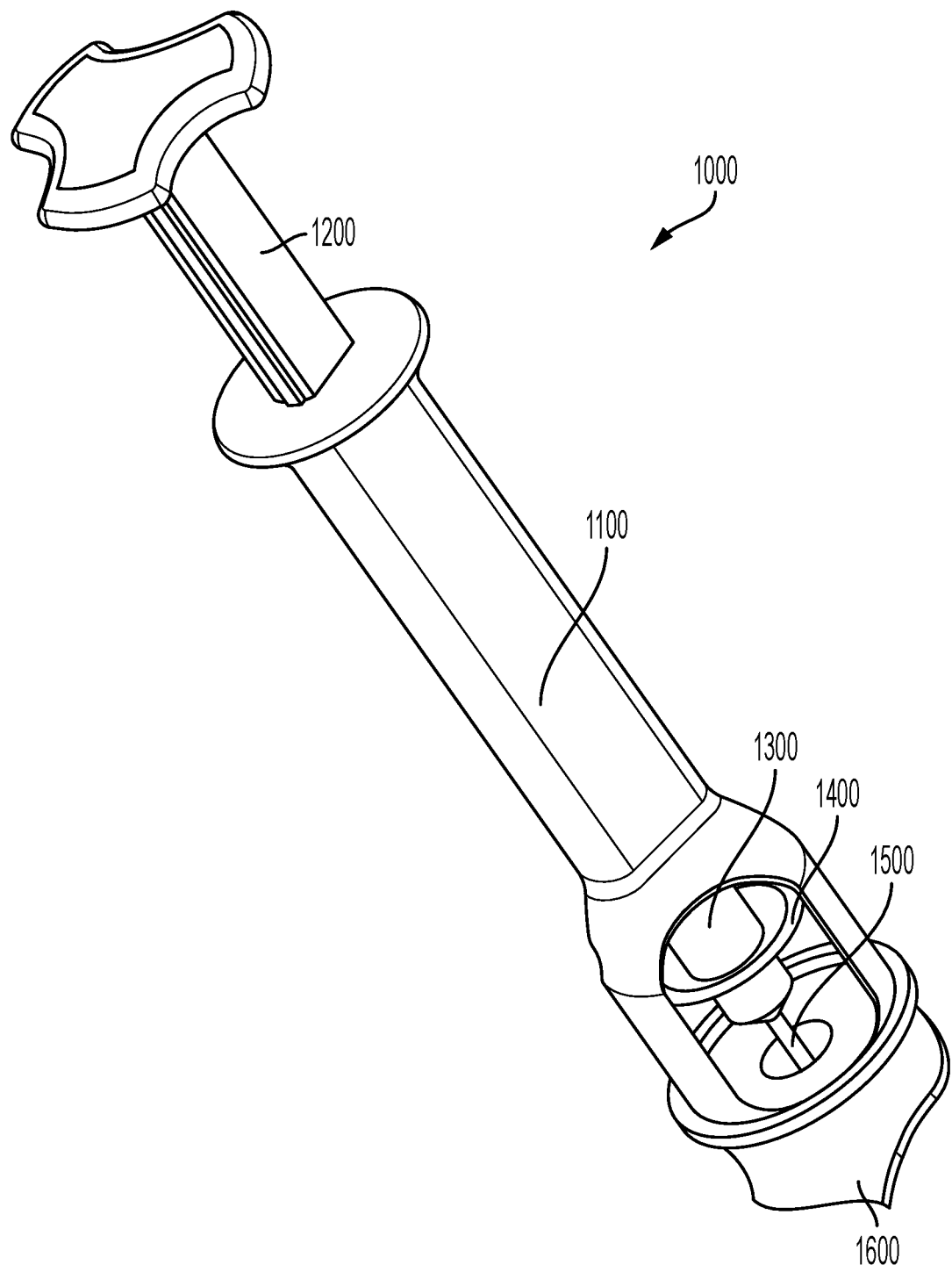
FIGS. 22-24 illustrate steps in a method of use of the impaction system of FIGS. 5 and 6.

In use, a patient may be prepared for the shoulder implant procedure according to known techniques. Such techniques may include gaining access to the proximal humerus of the patient through the skin, and resecting at least a portion of the humeral head along a substantially planar resection plane. If the base of the prosthetic stemless humeral implant is cannulated, a pilot wire may be used to assist the implantation. In particular, as shown in FIG. 22, a pilot wire 1500 may be inserted into the proximal humerus 1600 so that the pilot wire 1500 is positioned in the proximal humerus 1600 where the tip of the anchor 1406 of the base 1400 is intended to enter the proximal humerus 1600. In addition for assisting in positioning, the pilot wire 1500 may extend orthogonally or substantially orthogonally from the resection plane of the proximal humerus 1600 so that the impaction system 1000 may be guided along the desired direction orthogonal to the resection plane of the proximal humerus 1600.

Figure 23:
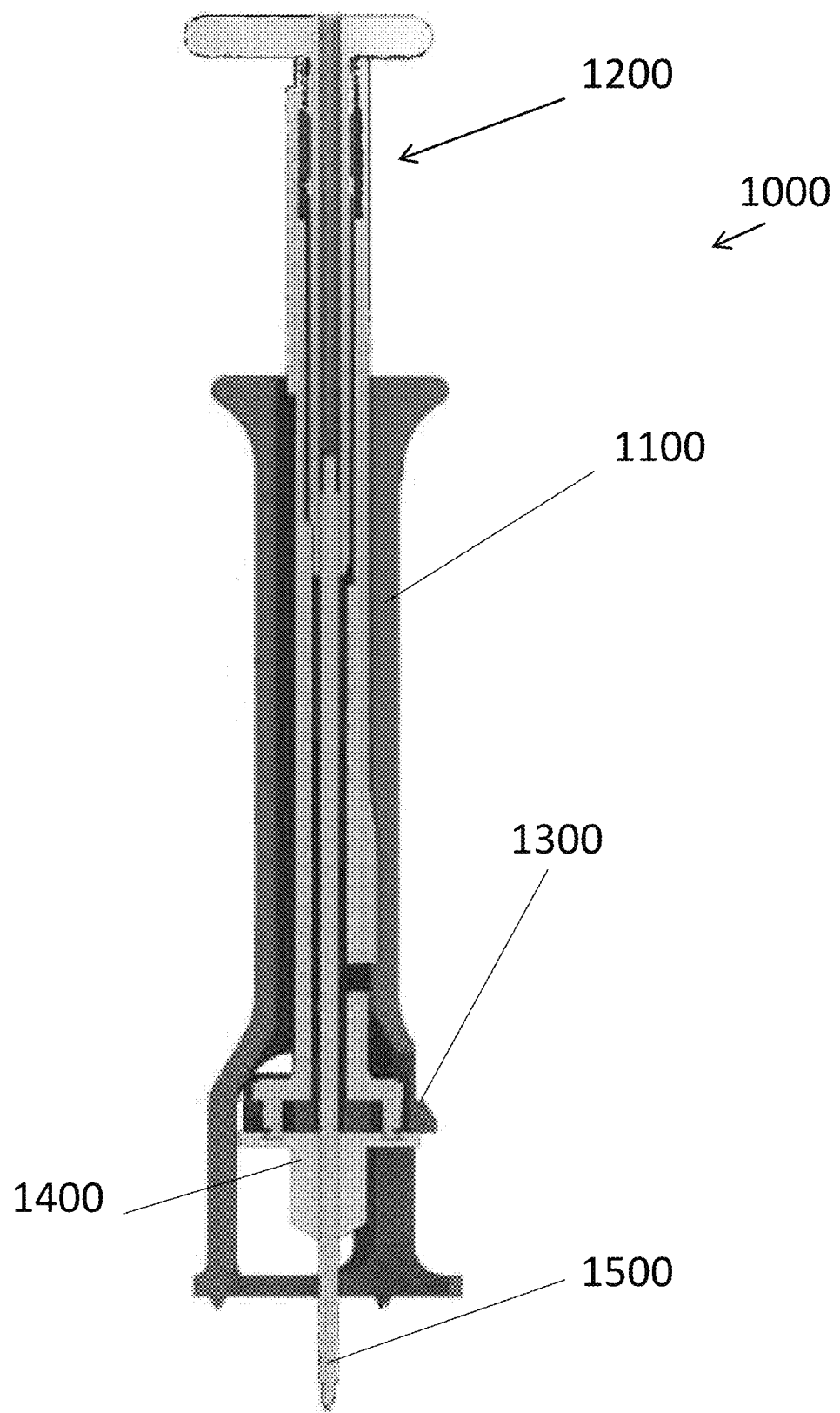

Prior to advancing the impaction system 1000 over the pilot wire, the impaction system 1000 may be assembled and coupled to the base 1400 of the prosthetic stemless humeral implant. It should be understood that the impaction system 1000 may be provided to the end user in the assembled condition, or otherwise the end user may assemble the device at the appropriate time prior to use. Once the impaction system 1000 is assembled, the knob 1204 may be unscrewed so that fingers 1236, 1238 are in a non-splayed condition with a first relatively short distance between the fingers 1236, 1238. The fingers 1236, 1238 may be inserted into apertures 1410, 1412 of base 1400, and the know 1204 may be turned to splay finger 1238 radially outwardly relative to finger 1236, so that the fingers 1236 and 1238 fully engage the collar 1402 and lock the base 1400 to impaction system 1000, with the proximal surface 1404 of the collar 1402 being flush and in contact with the distal surface 1308 of the impaction tip 1300. At this point, with the base 1400 assembled to the impaction system 1000, the assembly may be advanced over the pilot wire 1500 until the distal surface of the rim 1112 of the stabilizer 1104 is flush and in contact with the resection plane of the proximal humerus 1600, as shown in FIG. 22. The user should confirm that there is good contact between the stabilizer 1104 and the resection plane of the proximal humerus 1600, and if spikes 1114 are included on the stabilizer 1104, impaction system 1000 may be pressed to dig the spikes 1114 into the bone to help maintain the desired relative positioning between the stabilizer 1104 and the resection plane of the proximal humerus 1600. FIG. 23 illustrates a cross-section of the impaction system 1000 with the pilot wire 1500 extending partially therethrough, in a position similar to that shown in FIG. 22.

Figure 24:
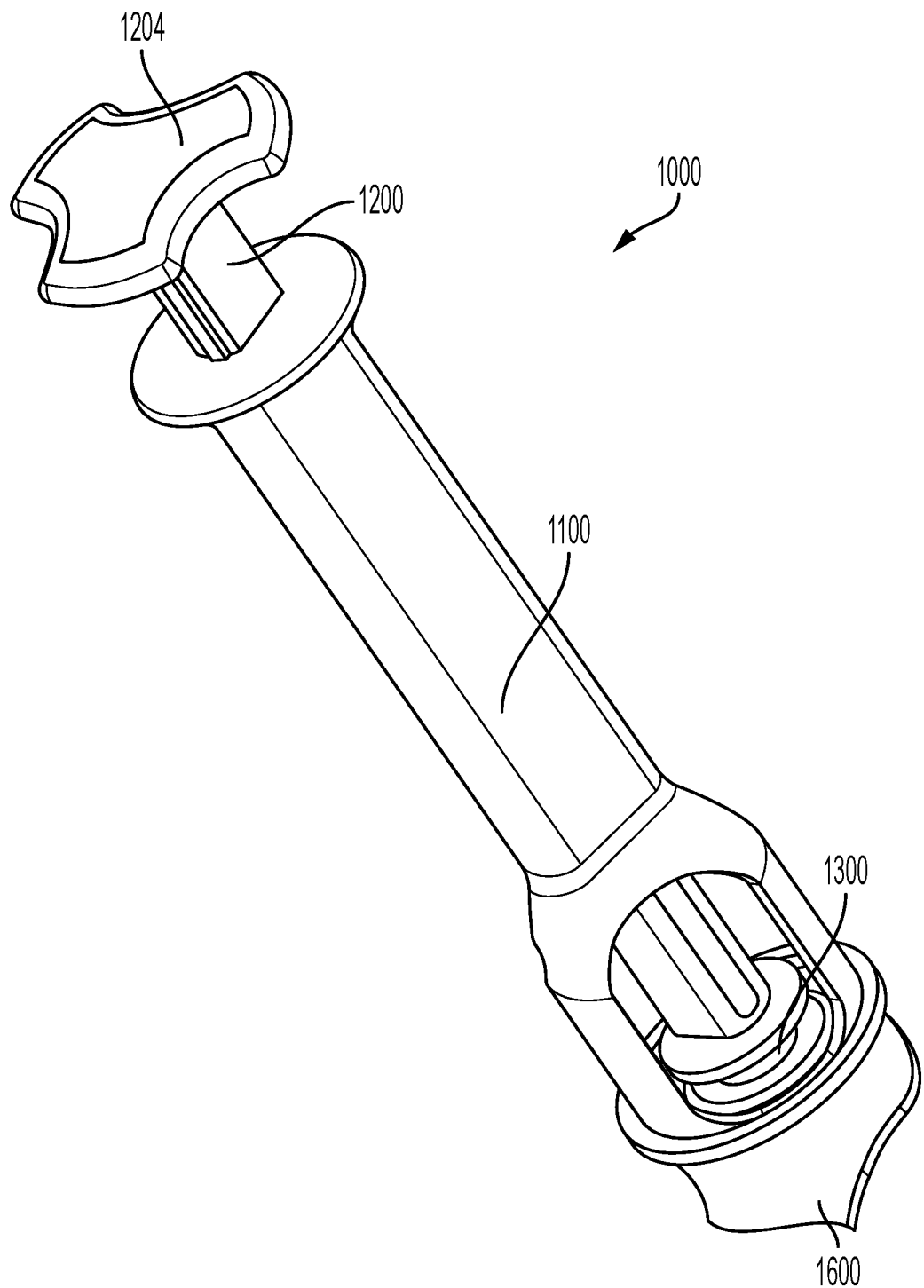

During the step of making initial contact between the stabilizer 1400 and the proximal humerus 1600, the impaction member 1200 is in a first proximal position relative to housing 1100, such that when the stabilizer 1400 is in contact with the resection plane of the proximal humerus 1600, the base 1400 of the prosthetic stemless humeral implant is a spaced distance from the proximal humerus 1600. As described above, the impaction member 1200 may be maintained in this position with the assistance of the friction provided between the impaction member 1200 and the housing 1100 by virtue of the bump-out 1230 of the flexure member 1228. The openings or windows provided in stabilizer 1104 may assist with the confirmation of the desired positioning between the impaction system 1000, base 1400, and proximal humerus 1600. Once the desired position is confirmed, the user may strike the knob 1204 of the impaction member 1200, for example with a mallet or similar device, to drive the base 1400 into the proximal humerus 1600, with the stabilizer 1400 and the pilot wire 1500 (if used) assisting in ensuring that the base 1400 is driven in the desired direction orthogonal to the resection surface of the proximal humerus 1600. During the impaction, the impaction member 1200 is prevented from rotating, as described above, and the protruding track 1226 may assist in guiding the impaction member 1200 distally. As shown in FIG. 24, after impaction, the impaction member 1200 has moved distally with respect to housing 1100, and the base 1400 is not visible in FIG. 24 because it has entered the proximal humerus 1600. The user may confirm that the base 1400 is fully positioned at the correct depth in the proximal humerus by viewing the impaction tip 1300 through the windows or openings in the stabilizer 1400, confirming that the impaction tip 1300 has engaged the resection plane of the proximal humerus 1600. At this point, the knob 1204 may be unscrewed to unlock the fingers 1236, 1238 from the base 1400, and the impaction system 1000 may be removed from the pilot wire 1500, and the pilot wire 1500 may be removed from the bone. With the base 1400 of the prosthetic stemless humeral implant in the desired implanted position, a corresponding head of a prosthetic stemless humeral implant may be coupled to the base 1400 to complete the implant of the prosthetic stemless humeral implant. If not already prepared, the glenoid may be prepared to accept a glenoid implant if being used, and the incision may be closed to complete the shoulder implant procedure.

Although the use of a pilot wire 1500 is described, it should be understood that the pilot wire 1500 may be fully omitted, whether or not the base 1400 of the prosthetic stemless humeral implant includes a cannulation to receive such a guide wire 1500. Although the guidewire 1500 may be helpful, it should be understood that the stability and positioning provided by the stabilizer 1104 of the housing 1100 may be sufficient to ensure that the base 1400 of the prosthetic stemless humeral implant is driven into the proximal humerus 1600 along the desired trajectory and in the desired position.

Figure 25:
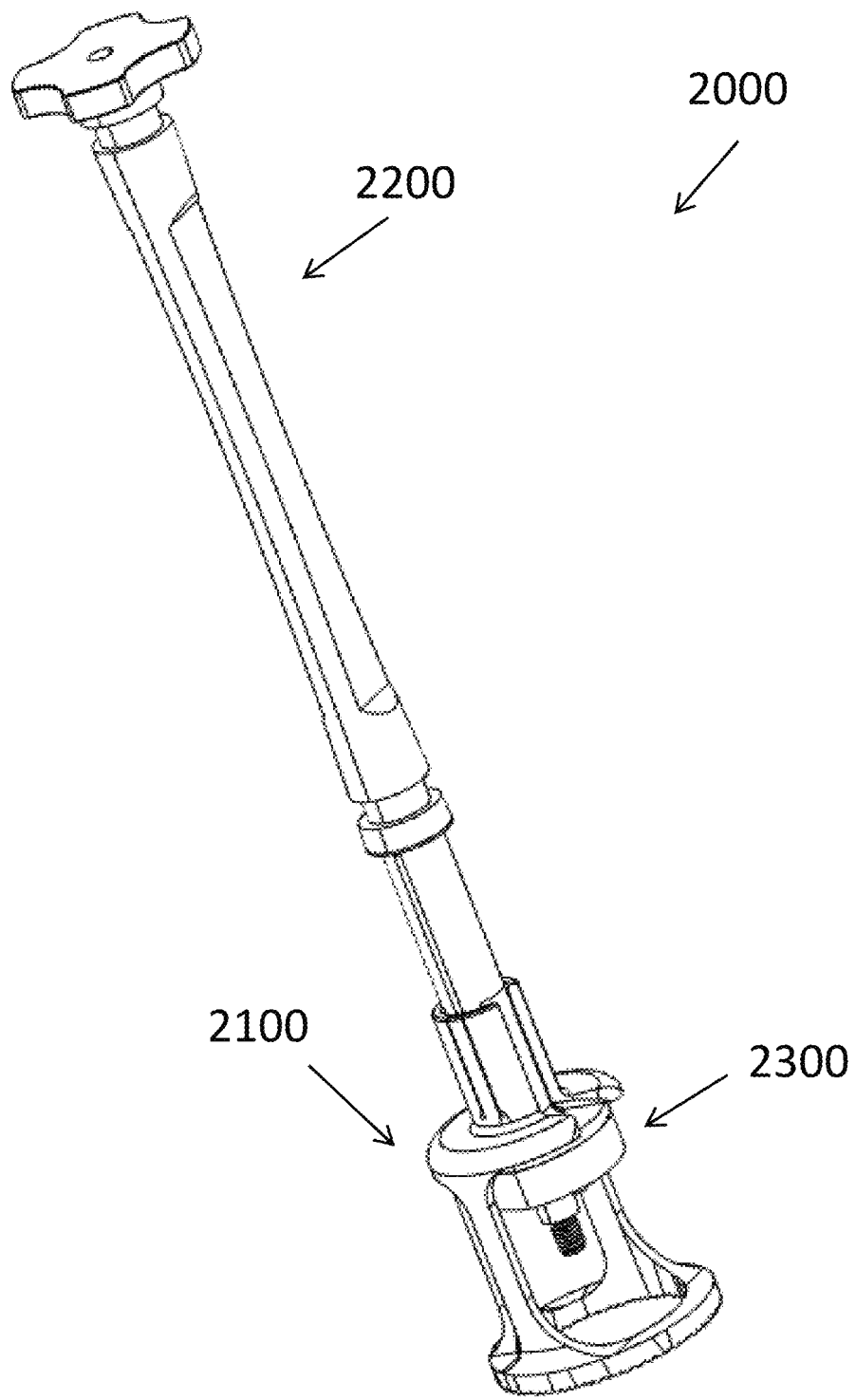
FIG. 25 is a perspective view of an impaction system according to another embodiment of the disclosure.

FIG. 25 illustrates another embodiment of an impactor assembly 2000 intended to provide the same or similar benefits as that described above for impactor assembly 1000. Various parts of impactor assembly 2000 are similar or identical to those described above in connection with impactor assembly 1000. Those components are generally labeled with a part number similar to the corresponding part in the impactor assembly 1000, using a 2000 prefix instead of a 1000 prefix. Impaction system 2000 may include a housing 2100, an impaction member 2200, and an impaction tip 2300, which each serve generally similar purposes to their corresponding parts in impactor assembly 1100.

Figure 26:
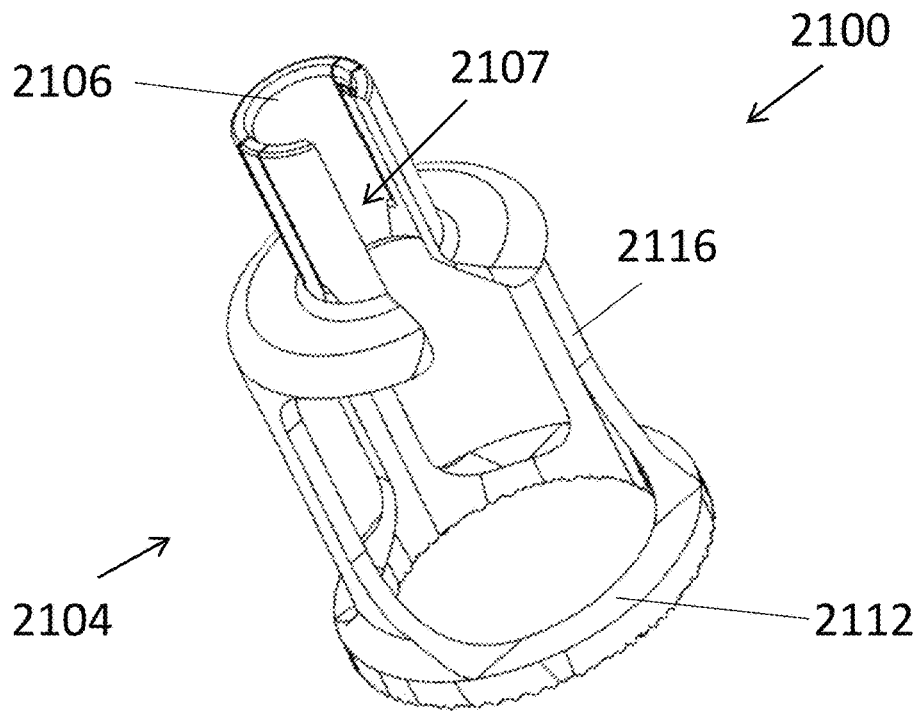
FIGS. 26 and 27 are top and bottom perspective views, respectively, of a housing of the impaction system of FIG. 25.
Figure 27:
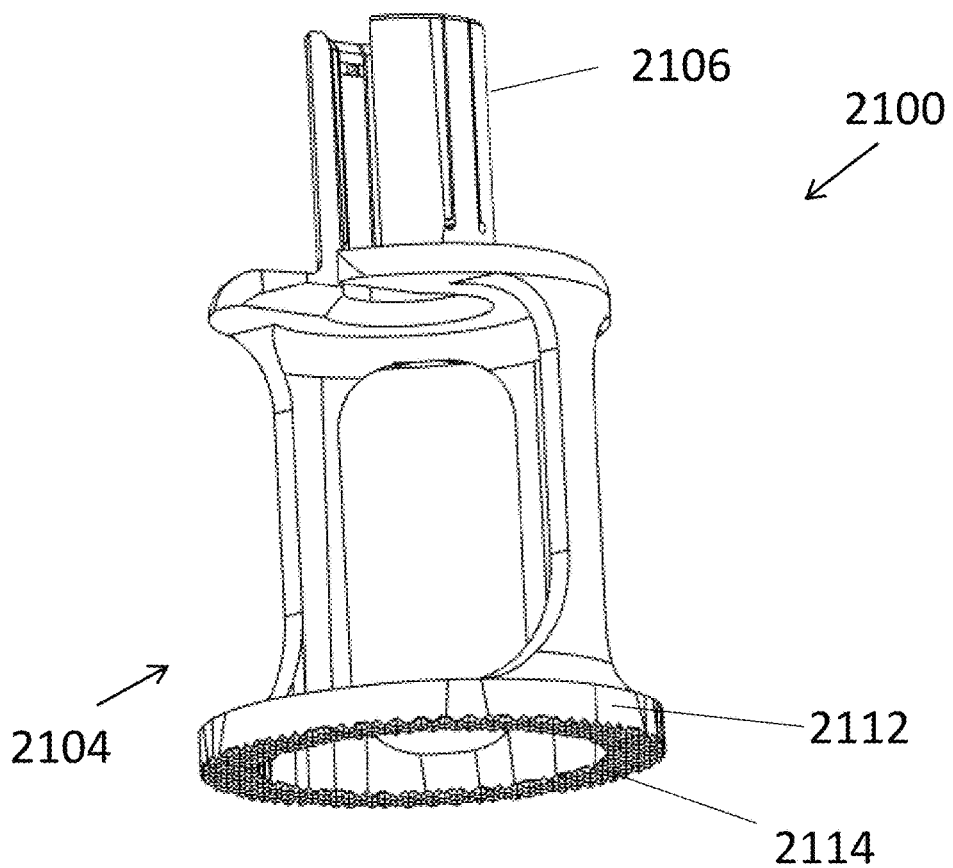

FIGS. 26 and 27 are top and bottom perspective views, respectively, of the housing 2100 of impaction system 2000. Generally, compared to housing 1100, housing 2100 is shorter and allows for a side entry of the impaction member 2200 through the housing 2100. Housing 2100 includes a distal stabilizer 2104 and a short shaft 2106 extending proximally from the stabilizer 2104. Shaft 2106 is defined by a substantially circular member that spans less than a full circumference, so that a slot 2107 leads into an interior space of the shaft 2106 between a proximal opening of the shaft 2106 and a distal opening of the shaft 2106. As explained in greater detail below, the impaction member 2200 may be inserted laterally through the slot 2107 when coupling or de-coupling the impaction member 2200 to the housing 2100. Stabilizer 2104 may extend from the distal end of shaft 2106 and include a rim 2112. In the illustrated embodiment, rim 2112 is substantially circular and defines a central opening. The distal surface of rim 2112 is preferably substantially flat so that, upon contact of rim 2112 with a planar surface, such as the resection plane of a proximal humerus, the central longitudinal axis of the impaction system 2000 is orthogonal or substantially orthogonal with respect to the distal surface of rim 2112 and the resection plane of the proximal humerus. The central opening defined by rim 2112 is preferably sized and shaped to allow impaction tip 2300, if used, and a base of a prosthetic humeral implant coupled to the impaction system 2000 to be driven through the central opening of the rim 2112.

As best seen in FIG. 27, the distal surface of rim 2112 may include a frictional engagement feature 2114. In the illustrated embodiment the frictional engagement feature 2114 is a patterned surface, such as a waffle-pattern, knurling, or another pattern. However it should be understood that spikes similar to those described in stabilizer 1104 may be used instead of the frictional engagement feature 2114, and similarly the spikes 1114 of stabilizer 1104 may instead take a form similar to the engagement feature 2114 of stabilizer 2104. Frictional engagement feature 2114 may assist in maintaining the placement of the housing 2100 of the impaction system 2000 in a desired position after initially placing the impaction system 2000 on the proximal humerus, and during the process of impacting the base of the prosthetic stemless humeral implant into the proximal humerus, so that the position of the housing 2100 does not change. It should be understood that although engagement feature 2114 may be omitted in come embodiments.

In the illustrated embodiment, housing 2100 includes a plurality of extensions 2116 connecting the distal end of the shaft 2106 to the rim 2112 of the stabilizer 2104. Although three extension members 2116 are shown, more or fewer may be provided. It should be noted that, while extension members 1116 of housing 1100 are positioned at substantially equal intervals around the circumference of rim 1112, extension members 2116 are positioned to allow for a relatively large opening adjacent slot 2107, so that no extension members 2107 would block the ability of the impaction member 2200 from being inserted laterally into shaft 2106 via slot 2107. As with stabilizer 1104, stabilizer 2104 includes openings or windows to allow for visualization of components positioned within the stabilizer 2104.

Figure 28:
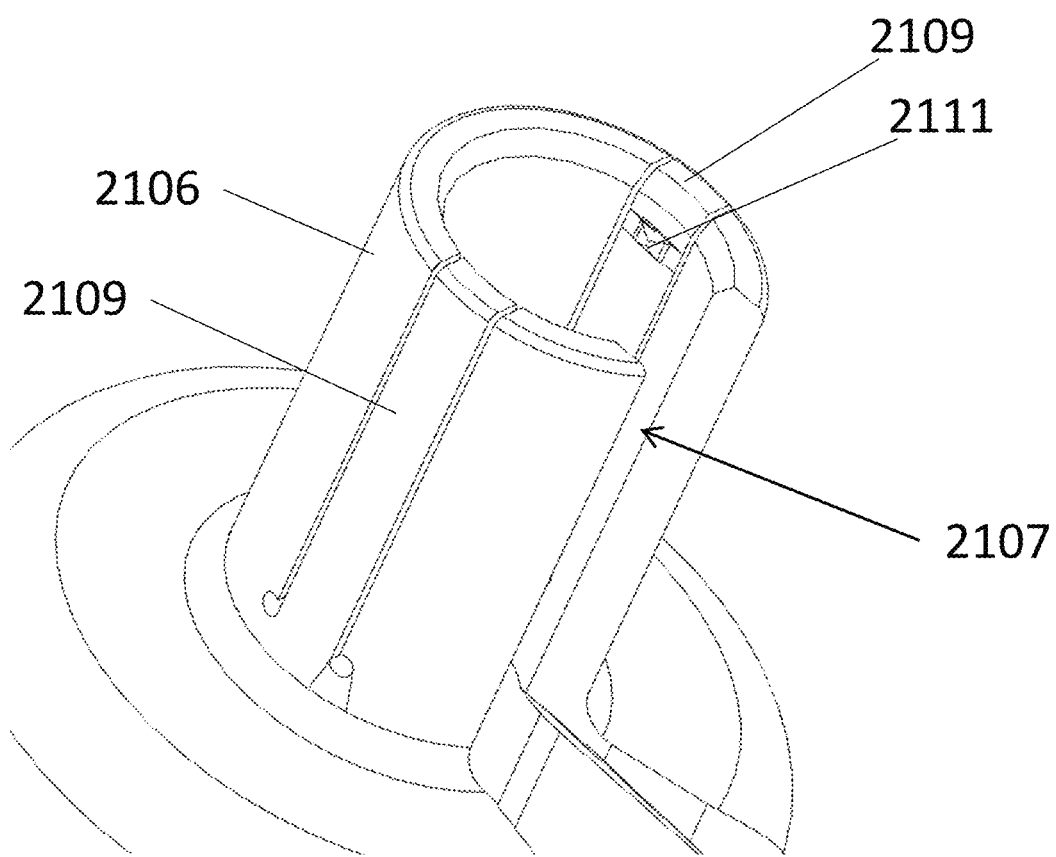
FIG. 28 is an enlarged perspective view of a shaft portion of the housing of FIGS. 26 and 27.

FIG. 28 is an enlarged perspective view of a shaft portion of the housing of FIGS. 26 and 27. The shaft 2106 may include two flexure members 2109. Each flexure member 2109 may be defined between two slots that extend from a proximal portion of the shaft 2106 through the distal end of the shaft 2106, so that the flexure member 2109 is capable of flexing radially inward or outward relative to the central longitudinal axis of shaft 2106. Each flexure member 2109 may also include a detent 2111 on an interior surface of the flexure member 2109, the detent 2111 extending a distance toward the longitudinal center of the shaft 2106. Preferably, the flexure members 2109 are positioned on substantially diametrically opposed portions of the shaft 2106, on opposite sides of the entry slot 2107. As is explained in greater detail below, the flexure members 2109 and detents 2111 may assist in connecting a portion of the impaction member 2200 to the housing 2100.

Figure 29:
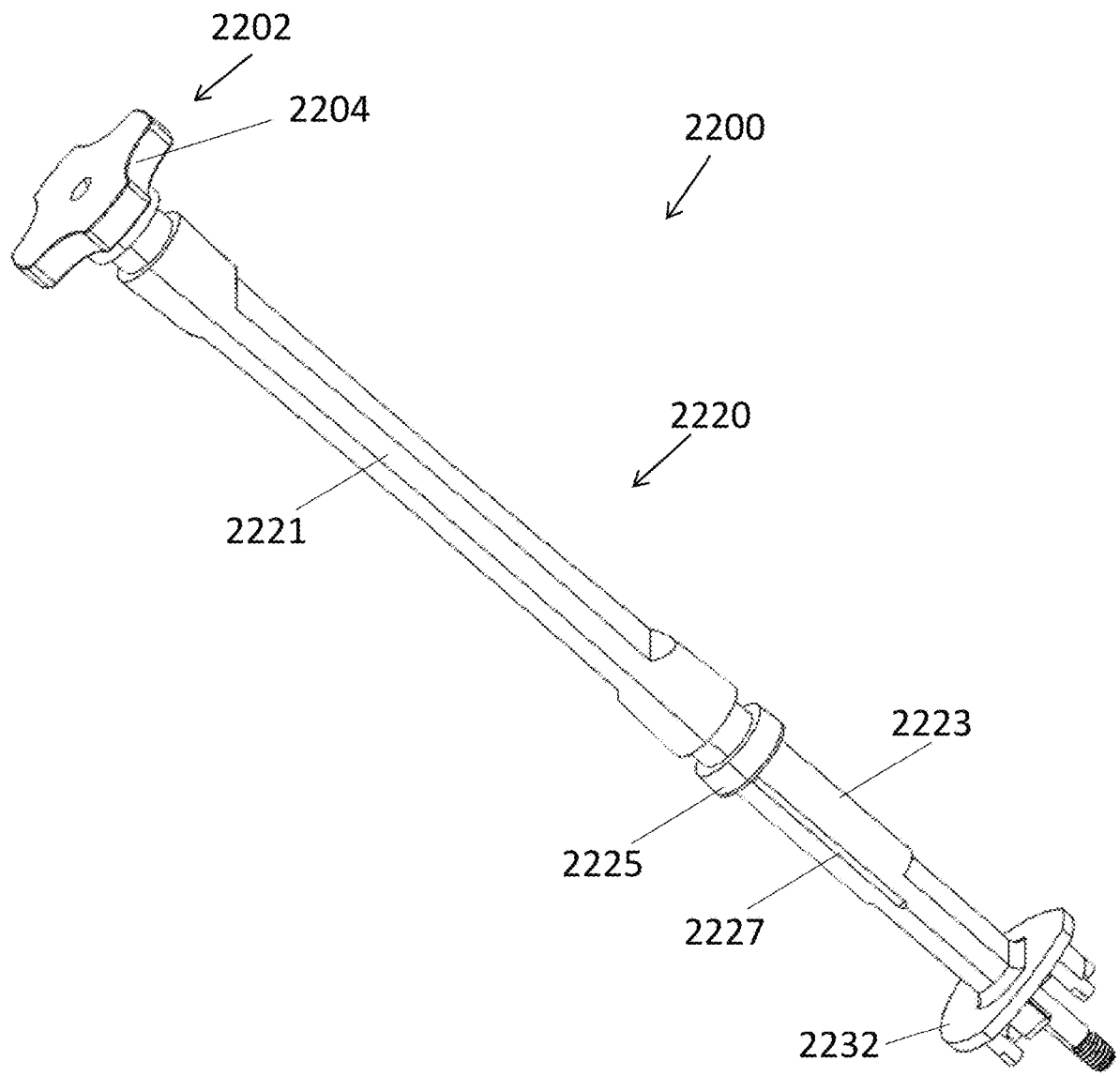
FIGS. 29 and 30 are top and bottom perspective views, respectively, of an impaction member of the impaction system of FIG. 25.
Figure 30:
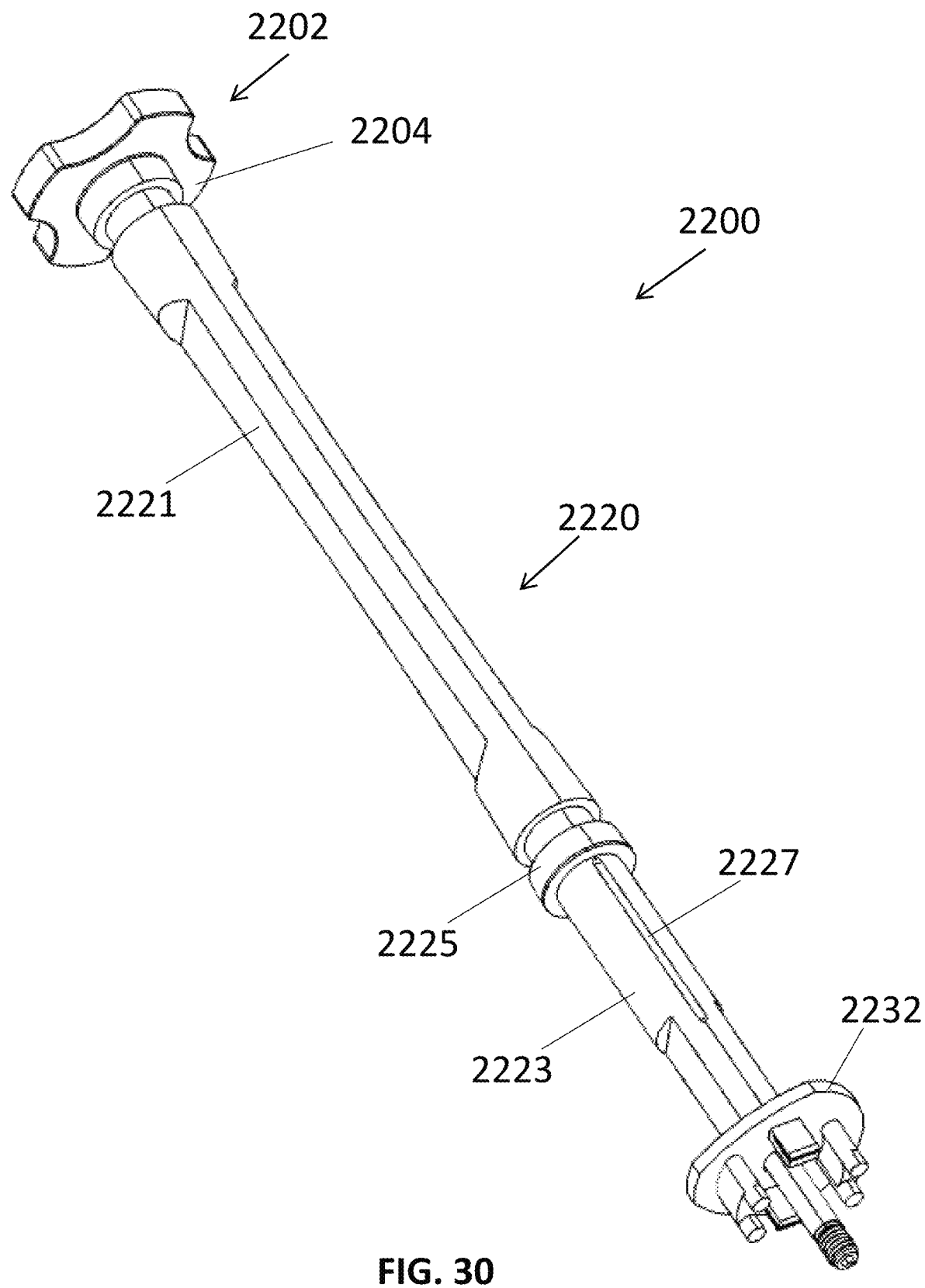

FIGS. 29 and 30 are top and bottom perspective views, respectively, of the impaction member 2200. A proximal end of the impaction member 2200 is adapted to be impacted to drive a distal end of the impaction member 2200, and in particular a base of the prosthetic stemless humeral implant coupled to the distal end of the impaction member 2200, into the bone of the proximal humerus. As will be described below, the impaction member 2200 is slidably coupled to the housing 2110 so that, when the housing 2100 is in the desired position against the resection plane of the proximal humerus, impacting the impaction member 2200 will drive the impaction member 2200 along the central longitudinal axis of the impaction system 2000, which in the desired position is orthogonal or substantially orthogonal to the resection plane of the proximal humerus. Impaction member 2200 may be formed of two pieces, including handle portion 2202 and a shaft portion 2220.

Figure 31:
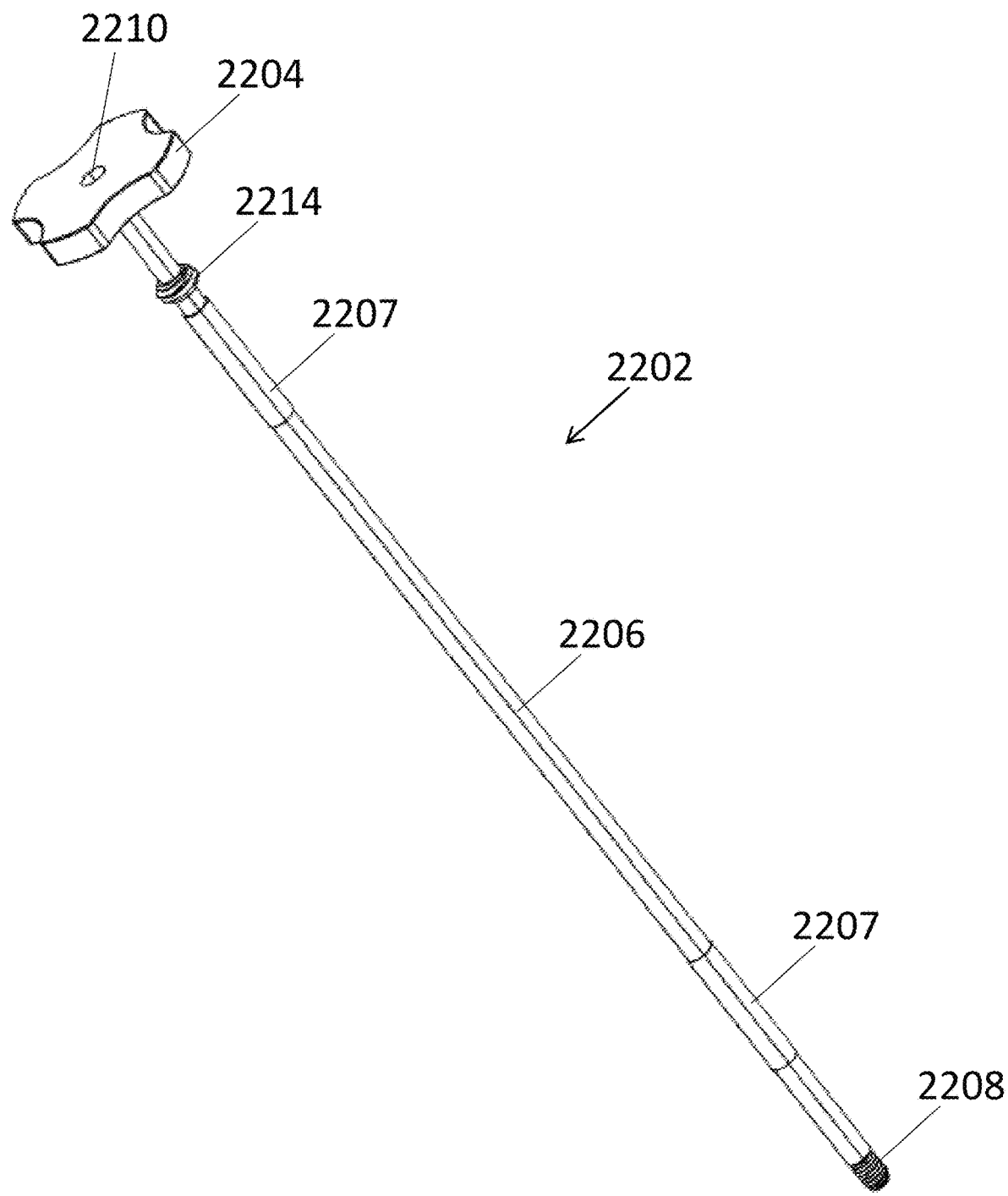
FIG. 31 is a perspective view of a handle portion of the impaction member of FIGS. 29 and 30.

FIG. 31 is a perspective view of the handle portion 2202 of the impaction member 2200. The proximal end of the handle portion 2202 may include a handle 2204 at a proximal end thereof. Preferably, handle 2204 includes a relatively large flat surface conducive to being impacted, for example by a mallet or a hammer device. In the illustrated example, handle 2204 is contoured to assist a user in turning handle 2204, and thus handle portion 2202, as described below. Handle portion 2202 may include a shaft 2206 extending distally from a center of handle 2204, terminating in a distal tip 2208, which may be threaded. A pilot wire channel 2210 may extend partially or completely through the handle portion 2202, which may be sized and shaped to receive a pilot wire therethrough. If a pilot wire is used, as is described in greater detail below, it may be temporarily implanted into the proximal humerus to guide the impaction system 2000, along with a prosthetic stemless humeral implant attached thereto, into a desired position and orientation with respect to the resection plane of the proximal humerus. Similar to second thread 1214 of shaft 1206, shaft 2206 may include a capture thread 2214 that may be used to help retain the shaft 2206 within shaft portion 2220. The shaft portion 2220 may include additional corresponding threads and/or undercuts on the interior diameter thereof that may be used to retain the capture thread 2214. This interaction may help prevent the shaft 2206 from slipping out of shaft portion 2220. Shaft 2206 may also include two larger diameter portions 2207 along the central outside diameter of the rod. These larger diameter portions 2207 may help to isolate the contact surfaces between the outside diameter of shaft 2206 and the inner diameter of shaft portion 2220.

FIG. 32 is a cross section of the shaft portion 2220 of impaction member 2200, and FIG. 33 is a cross-section of handle portion 2202 received within shaft portion 2220. Referring to FIGS. 29-30 and 32-33, the proximal end of shaft portion 2220 may include an opening 2222 through which the handle portion 2202 may be inserted. The shaft portion 2220 may include a proximal shaft 2221 and a distal shaft 2223 separated by a collar 2225. Part of the distal shaft 2223 may have a substantially circular profile, with another part of the distal shaft 2223 having a portion with two opposing flat surfaces each connected by a rounded portion. The rounded portion may have a similar or identical radius of curvature as the portion of distal shaft 2223 with a circular profile, and the distanced between the opposing flattened portions is smaller than the diameter of the portion of the distal shaft 2223 with a circular profile. That distance between opposing flattened portions of distal shaft 2223 is slightly smaller than the width of the slot 2107 in the shaft 2106 of housing 2100, while the diameter of the circular portion is larger than the width of the slot 2107 in the shaft 2016 of housing 2100. With this configuration, the flattened portion of the distal shaft 2223 may be passed laterally through the slot 2107 in the shaft 2106 of housing 2100 in a first orientation, and then turned ninety degrees rotationally. Upon being turned, the detents 2111 in the flexure members 2109 of the shaft 2106 of housing 2100 may snap into corresponding grooves 2227 in the distal shaft 2223. After being turned about ninety degrees, the diameter of the rounded portion of distal shaft 2223 prevents the impaction member 2200 from laterally exiting the housing 2100 via the slot 2107 of the shaft 2106. The mating between the detents 2111 and the grooves 2227 provides a track along which the impaction member 2200 slide relative to the housing 2100. The collar 2225 may have a diameter larger than the inner diameter of the shaft 2106 of the housing 2100 so that the collar 2225 acts as a positive stop when the impaction member 2200 slides distally relative to the housing 2100. A distal flange 2232 positioned at the distal end of the distal shaft 2223, described in greater detail below, may similarly act as a positive stop when the impaction member 2200 slides proximally relative to the housing 2100.

Figure 34:
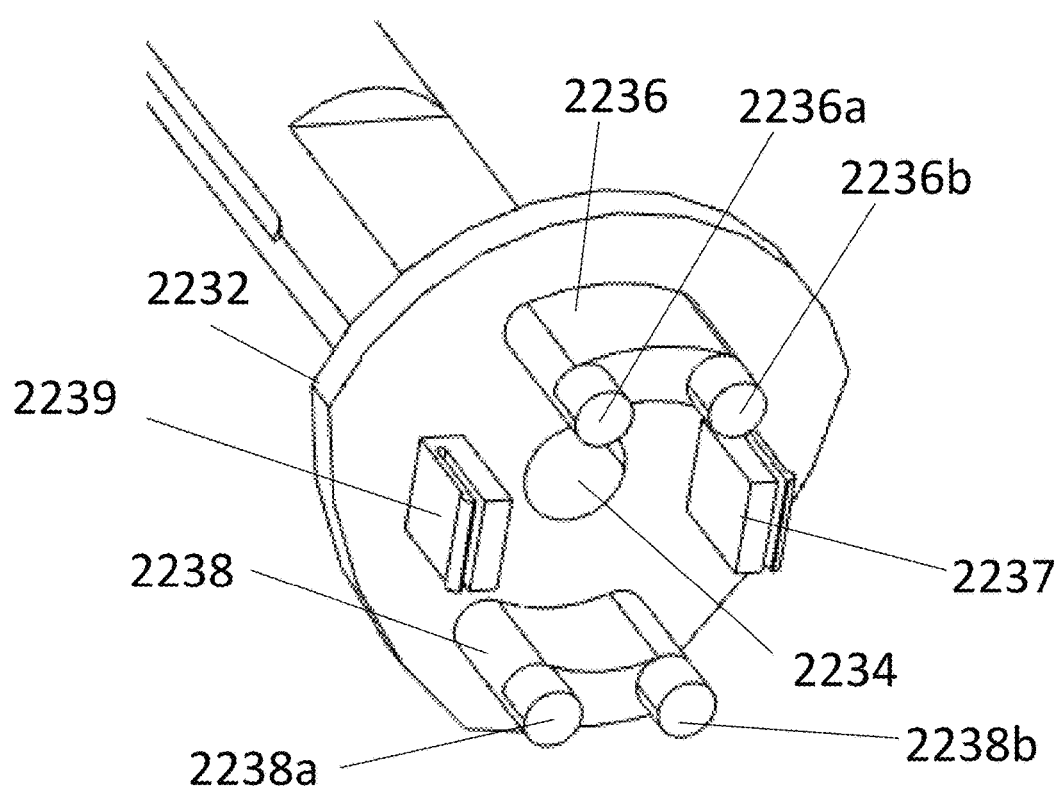
FIG. 34 is an enlarged view of a distal end of the shaft portion of FIG. 32.

FIG. 34 is an enlarged view of the distal flange 2232 of the distal shaft 2223 of the shaft portion 2220. In the illustrated embodiment, the distal flange 2232 has a shield-type shape, with a generally rounded top portion and a generally triangular bottom portion extending from the rounded top portion. It should be understood that the shape of the distal flange 2232 preferably corresponds to the shape of the collar of a base, which may help the user appropriately align the base to the impaction member 2200, although such correspondence is not necessary. In other embodiments, the distal flange 2232 may have a substantially circular shape.

Flange 2232 may include a central aperture 2234 so that the pilot wire described above may pass through the shaft portion 1220. A pair of fingers 2237, 2239 may extend distally from opposing sides of the central aperture 2234. Each finger 2237, 2239 may be substantially identical, and include a relatively thick inner extension nearer the central aperture 2234 and a relatively thin outer extension nearer the outer circumference of flange 2232. The outer extension may be coupled to the inner extension only near the connection to the flange 2232, such that the outer member of the fingers 2237, 2239 is able to flex. The relatively thin outer extension of each finger 2237, 2239 may also include a tab or lip at a distal end thereof, which may snap into a corresponding mating member in the impaction tip 2300 to secure the impaction tip 2300 to the impaction member 2200, described in greater detail below. Flange 2232 may also include a pair of anti-rotation tabs 2236, 2238 extending distally from distal flange 2232, each anti-rotation tab 2236, 2238 being positioned on opposing sides of the central aperture 2234. Each anti-rotation tab 2236, 2238 may include a pair of protrusions 2236a-b, 2238a-b that may be received within corresponding recesses in the base of the prosthetic stemless humeral implant. As described in greater detail below, these protrusions 2236a-b, 2238a-b may assist in preventing the base of the prosthetic stemless humeral implant from rotating as the distal tip 2208 of the handle portion 2202 of the impaction member 2220 is rotated into a corresponding thread in the implant member.

Figure 35:
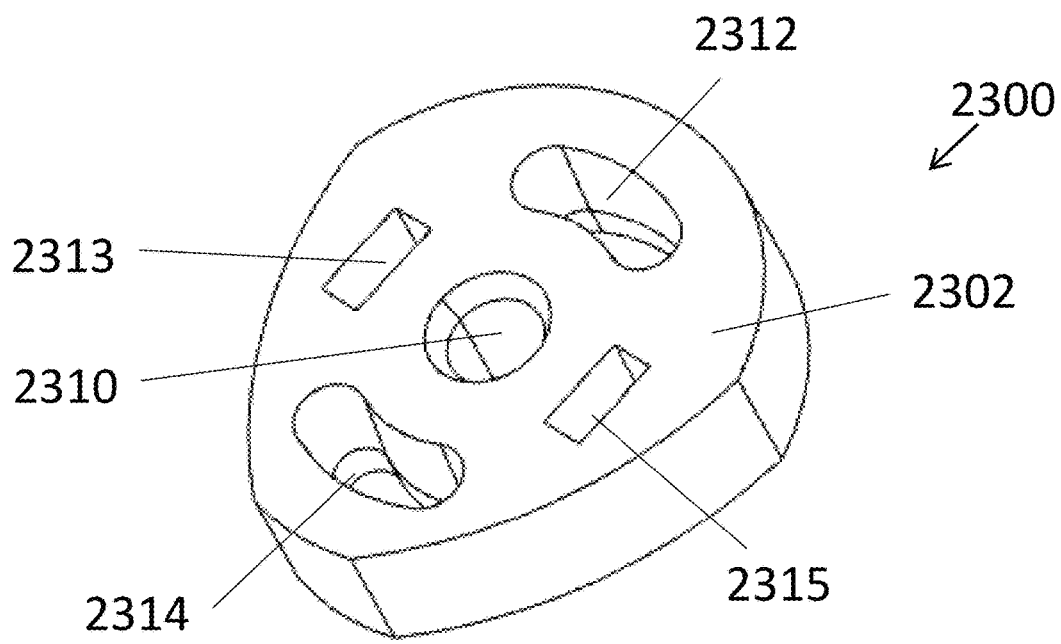
FIGS. 35 and 36 are top and bottom perspective views, respectively, of an impaction tip of the impaction system of FIG. 25.
Figure 36:
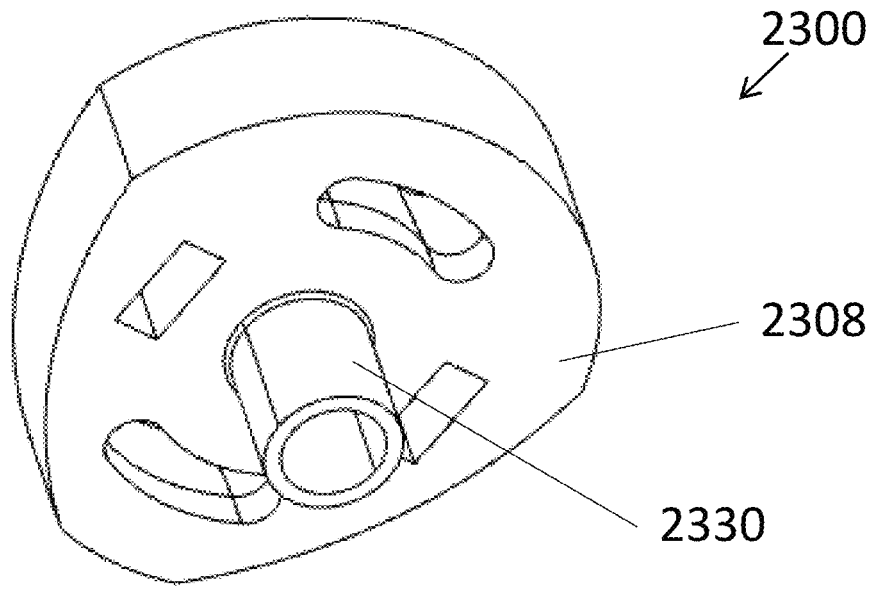
Figure 37:
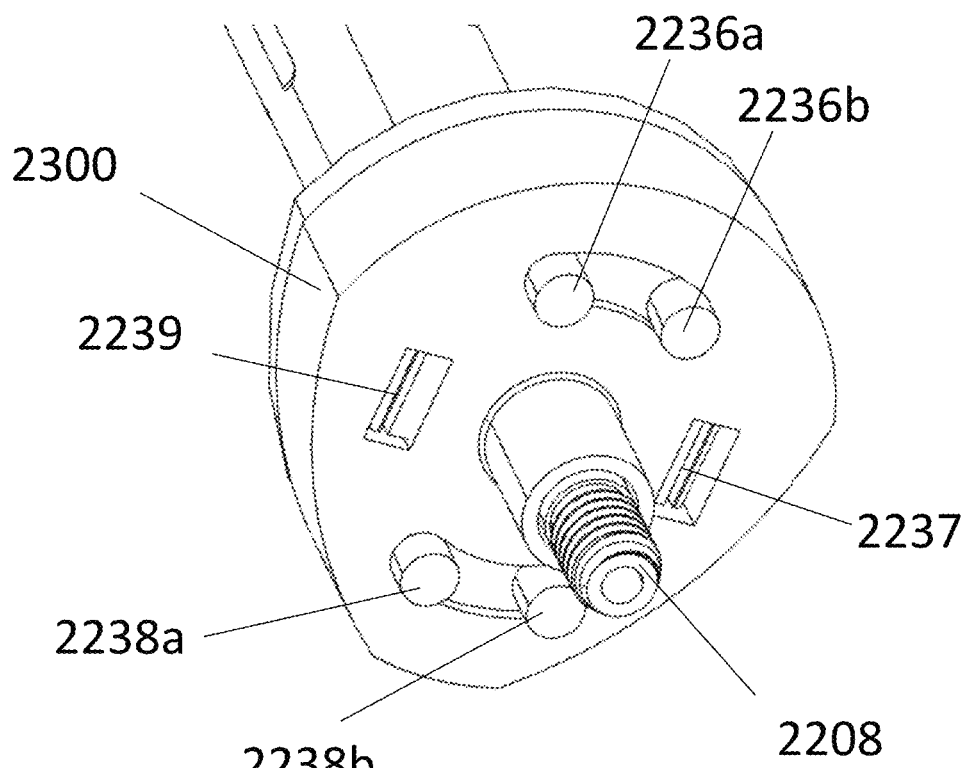
FIG. 37 is a bottom perspective view of the impaction member received within the impaction tip.

FIGS. 35 and 36 are top and bottom perspective views, respectively, of impaction tip 2300. Impaction tip 2300 assists in evenly transmitting forces from the strike of impaction to the base of the prosthetic stemless humeral implant. Impaction tip 2300 includes a substantially planar proximal surface 2302 that is sized and shaped to contact the distal surface of the flange 2232 of impaction member 2200, and a substantially planar distal surface 2308 that is sized and shaped to contact the proximal surface of a base of a prosthetic stemless humeral implant. Impaction tip 2300 may include a pilot wire aperture 2310 at a longitudinal center thereof, the pilot wire aperture 2310 leading to a pilot wire passageway that is sized and shaped to receive a pilot wire therethrough. The impaction tip 2300 may include a first aperture 2313 and a second aperture 2315 on opposite sides of the pilot wire passageway having shapes and sizes adapted to receive fingers 2237, 2239 snugly therein. Apertures 2313 and 2315 may include undercuts, recesses, or other surfaces that the tabs or lips of the fingers 2237, 2239 can flex into to snap the impaction tip 2300 onto the impaction member 2200. However, such "snapping" action is not required, as the impaction tip 2300 is ultimately sandwiched between the flange 2232 and the collar 2402 via threads on distal tip 2208 (best illustrated in FIG. 39). When the fingers 2237, 2239 are received within apertures 2313, 2315, the fingers 2237, 2239 do not protrude beyond the distal surface 2308 of the impaction tip 2300. Impaction tip 2300 may include another pair of apertures 2312, 2314 on opposite sides of the pilot wire aperture 2310. Apertures 2312, 2314 may have a shape corresponding to the shape of the anti-rotation tabs 2236, 2238 so that the anti-rotation tabs 2236, 2238 are received therein. When the anti-rotation tabs 2236, 2238 are received within apertures 2312, 2314, only the protrusions 2236a-b, 2238a-b protrude beyond the distal surface 2308 of the impaction tip 2300, as shown in FIG. 37. The distal surface of impaction tip 2300 may also include a cylindrical tube 2330 extending distally from the distal surface 2308 of the impaction tip 2300, concentric to the pilot wire aperture 2310. The cylindrical tube 2330 may be sized and shaped to receive the distal tip 2208 of the impaction member 2200 therethrough, as shown in FIG. 37.

Figure 38:
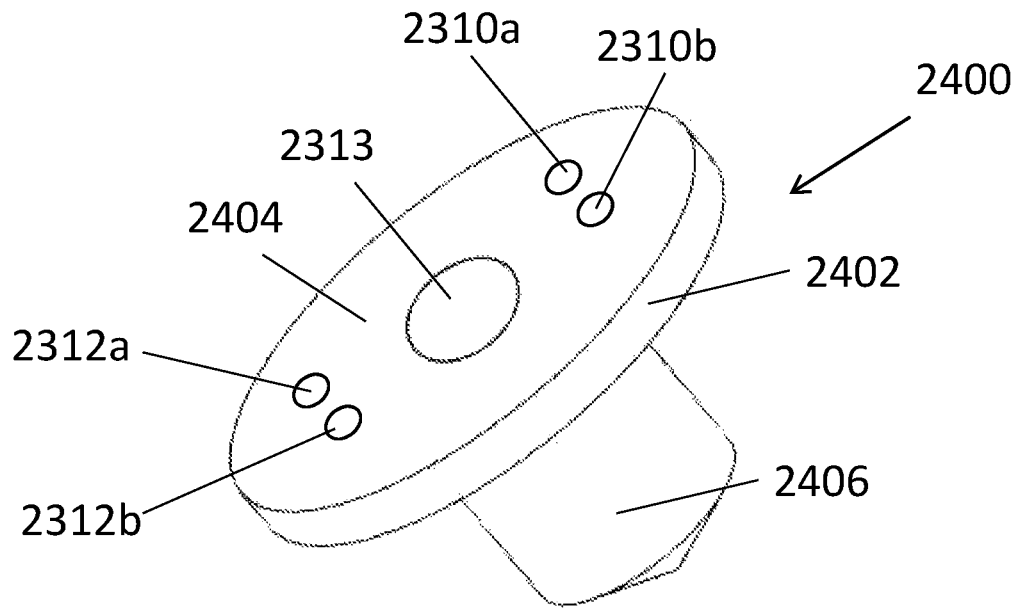
FIG. 38 is a top perspective view of a base of a prosthetic stemless humeral implant for use with the impaction system of FIG. 25.

FIG. 38 is a top perspective view of a base 2400 of a prosthetic stemless humeral implant. It should be understood that base 2400 is illustrated in a highly simplified manner in order to illustrate feature of the base 2400 that couple to corresponding features of the impaction system 2000. Otherwise, it should be understood that base 2400 may include any of the features described in connection with base 100, and thus similar features of base 2400 are not described in greater detail. Generally, base 2400 includes a collar 2402 with a proximal surface 2404, and an anchor 2406 extending from a distal surface of the collar. The collar 2402 may also include a central aperture 2313 extending a depth into anchor 2406. The central aperture 2313 may assist in coupling the impaction member 2200 to the base 2400, and may also function to allow a prosthetic humeral head to couple to the base 2400, similar to base 100. The collar 2402 may include a first pair of apertures 2310a, 2310b sized and shaped to receive the protrusions 2236a, 2236b of anti-rotation tab 2236, and a second pair of apertures 2312a, 2312b sized and shaped to receive the protrusions 2238a, 2238b of anti-rotation tab 2238. Although the proximal surface 2404 of the collar 2402 is illustrated as circular, it should be understood that it may have other shapes, including the shield-like shape of the impaction tip 2300 and the flange 2232.

Figure 39:
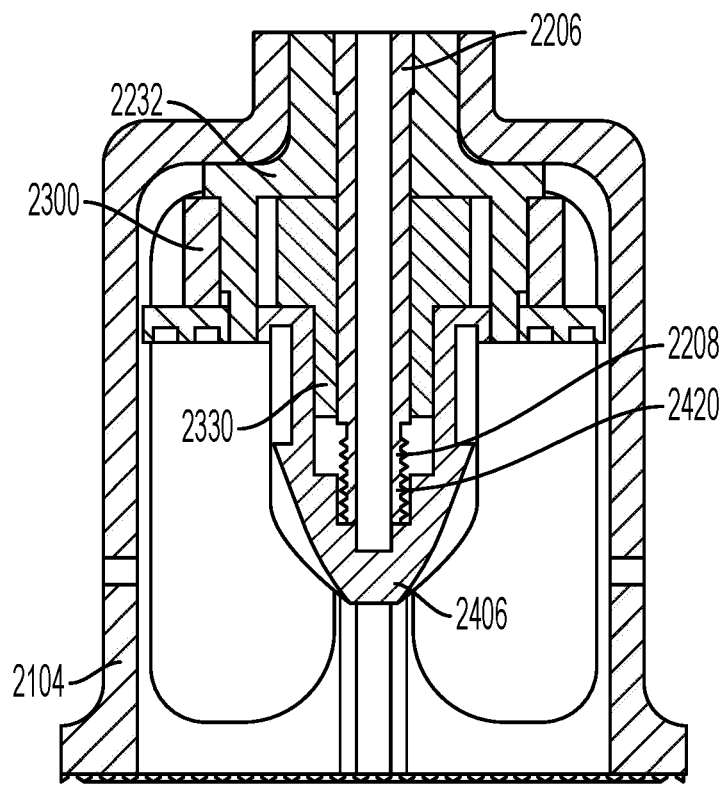
FIG. 39 is a cross-section of the base of FIG. 38 assembled to the impaction system of FIG. 25.

FIG. 39 is a cross-section of the base 2400 coupled to the impaction system 2000. As illustrated, the protrusions 2236a-b and 2238a-b are received within the apertures 2312a-b and 2314a-b in the collar 2402. The cylindrical tube 2330 of the impaction tip 2300 is received within the central aperture 2313 of the collar 2402. The shaft 2206 of the impaction member 2200 passes through the impaction tip 2300 and the distal tip 2208 extends beyond the cylindrical tube 2330 into engagement with corresponding mating threads 2420 within central aperture 2313. In order to secure the impaction member 2200 to the base 2400, the knob 2204 of the impaction member 2200 may be rotated, which causes rotation of the shaft 2206 and the distal tip 2208. As the distal tip 2208 threads into the corresponding threads 2420, the protrusions 2236a-b, 2238a-b of the anti-rotation tabs 2236, 2238 prevent the base 2400 from rotating, allowing the threads to fully engage to secure the base 2400 to the impaction system 2000. It should be understood that, although not illustrated, base 2400 can include a cannulation to accept a pilot wire, as can all the components of impaction system 2000, although a pilot wire is not necessary for use of the impaction system 2000.

The impaction system 2000 may be used in substantially the same manner as impaction system 1000 to drive the base 2400 into the proximal humerus. After the base 2400 is coupled to the impaction member 2200 and the impaction tip 2300 as described above, the assembly may be slid laterally into the housing 2100 as described above. The entire unit may then be advanced over a guidewire within the proximal humerus, and the procedures completed in substantially the same manner as described above with respect to impaction system 1000. Because the impaction using a mallet (or other suitable device) and the remainder of the implant procedure is substantially the same as described above in connection with impaction system 1000, it is not described again here. It should further be understood that housing 2100 may serve as a guide to locating the center of the resection plane of the proximal humerus. This could be done with the housing 2100 attached to the remainder of impaction system 2000, or otherwise the housing could be used independently as a guide, with the remainder of the impaction system attached to the housing while the housing is in the desired position on the proximal humerus.

Figure 40:
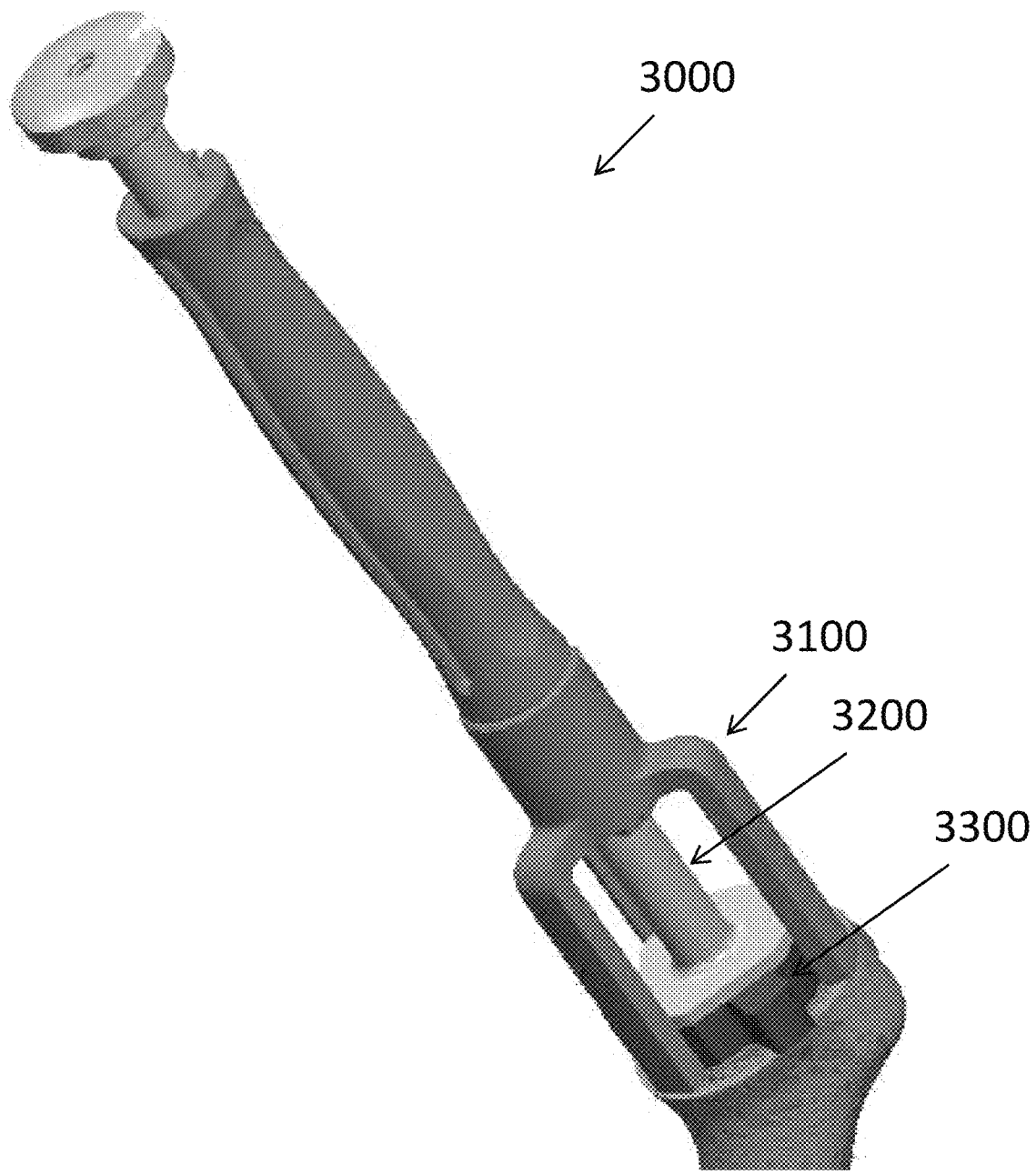
FIG. 40 is a perspective view of another embodiment of an impactor assembly in contact with a proximal humerus.

FIG. 40 illustrates a further embodiment of an impactor assembly 3000 intended to provide the same or similar benefits as those described above for impactor assembly 2000. Various parts of impactor assembly 3000 are similar or identical to those described above in connection with impactor assembly 2000. Those components are generally labeled with a part number similar to the corresponding part in the impactor assembly 2000, using a 3000 prefix instead of a 2000 prefix, although not all such components are labeled or separately described herein for purposes of brevity. Impaction system 3000 may include a housing 3100, an impaction member 3200, and an impaction tip 3300, which each serve generally similar purposes to their corresponding parts in impactor assembly 2000.

Figure 41:
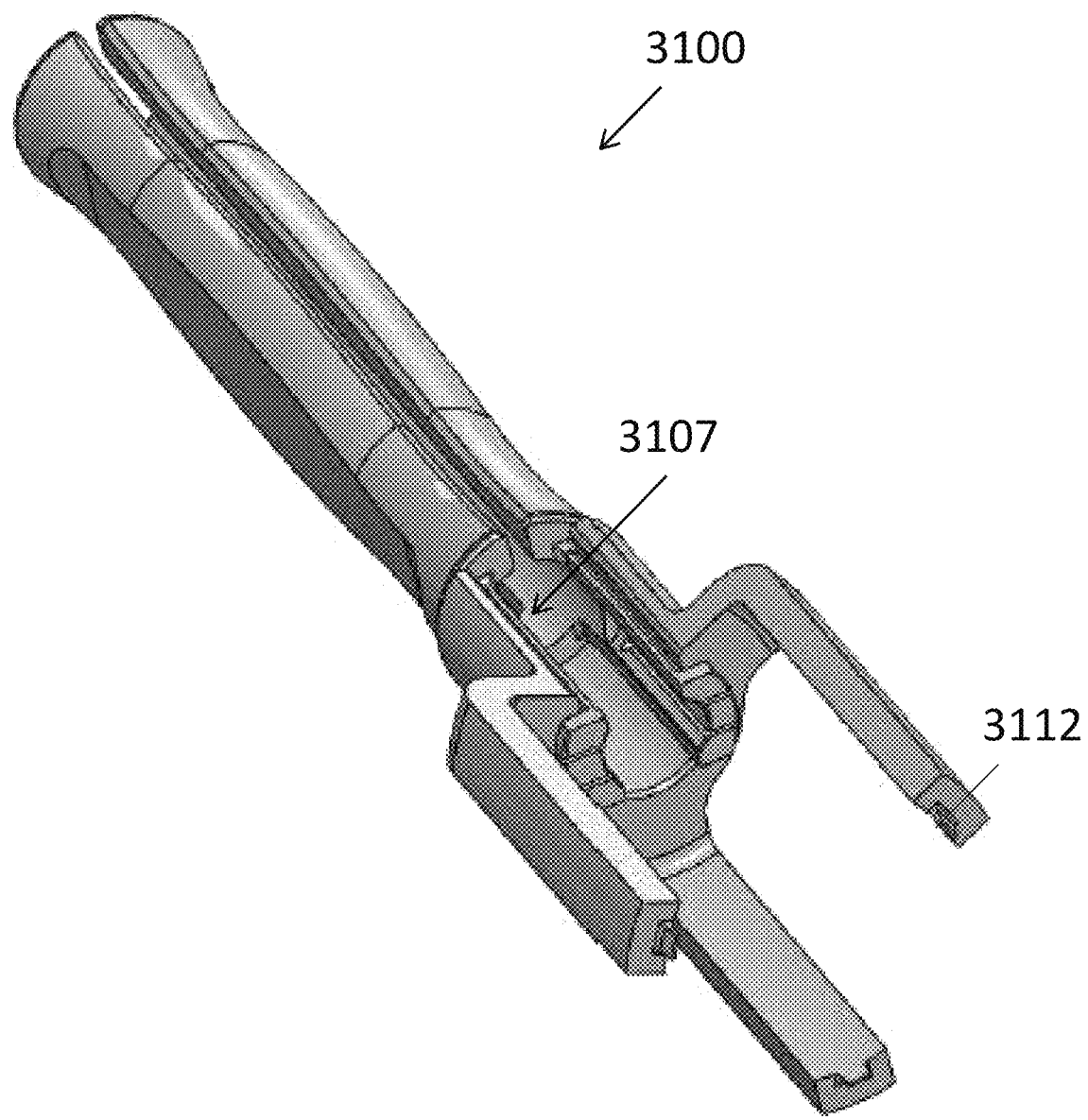
FIG. 41 is a perspective view of a housing of the impactor assembly of FIG. 40.

FIG. 41 is a perspective view of housing 3100, which may be generally similar to housing 2100 with certain exceptions. For example, the distal end of housing 2100 may omit a circular rim similar to rim 2114, and rather include frictional engagement members 3112 in the form of tabs or spikes that extend distally from the distal end of the struts or supports, with the frictional engagement members adapted to help keep the housing in contact with the proximal humerus. The elimination of rim 2114 may assist in improved visibility of contact with the proximal humerus. Similar to housing 2100, housing 3100 may include a slot 3107 to assist in lateral insertion of impaction member 3200 therethrough. Housing 3100 may include a more significant shaft portion extending proximally from the distal engagement portion compared to housing 2100.

Figure 42:
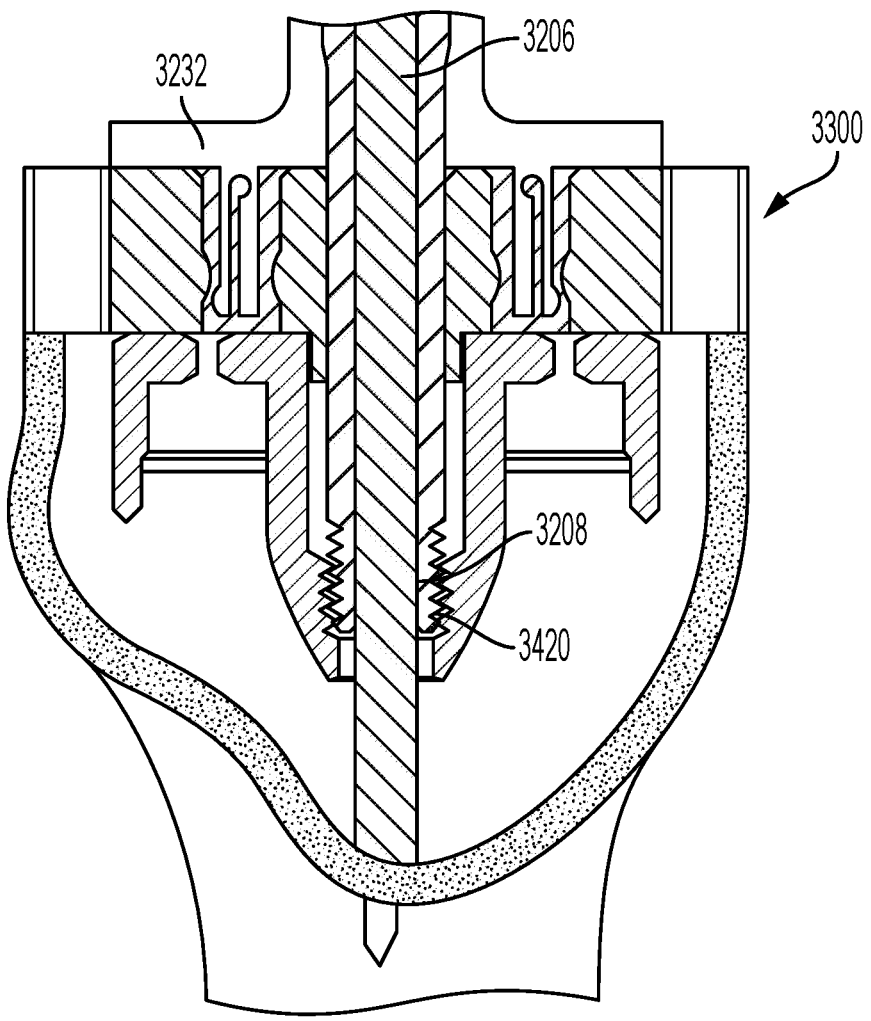
FIG. 42 is a cross-section of the impactor assembly of FIG. 40 positioned on the proximal humerus after impaction.

FIG. 42 illustrates a cross-section of impactor assembly 3000 assembled to a base of a stemless humeral implant which has been impacted into a proximal humerus using a guidewire or pilot wire. Similar to impactor assembly 2000, the handle portion of the impaction member 3200 may include a shaft 3206 that terminates in a threaded distal tip 3208 adapted to thread into a corresponding threads 3420 of a base member. Further, similar to other embodiments described herein, the impaction member 3200 may terminate in a flange 3232 that includes fingers or other flex members adapted to snap into impaction tip 3300.

Figure 43:
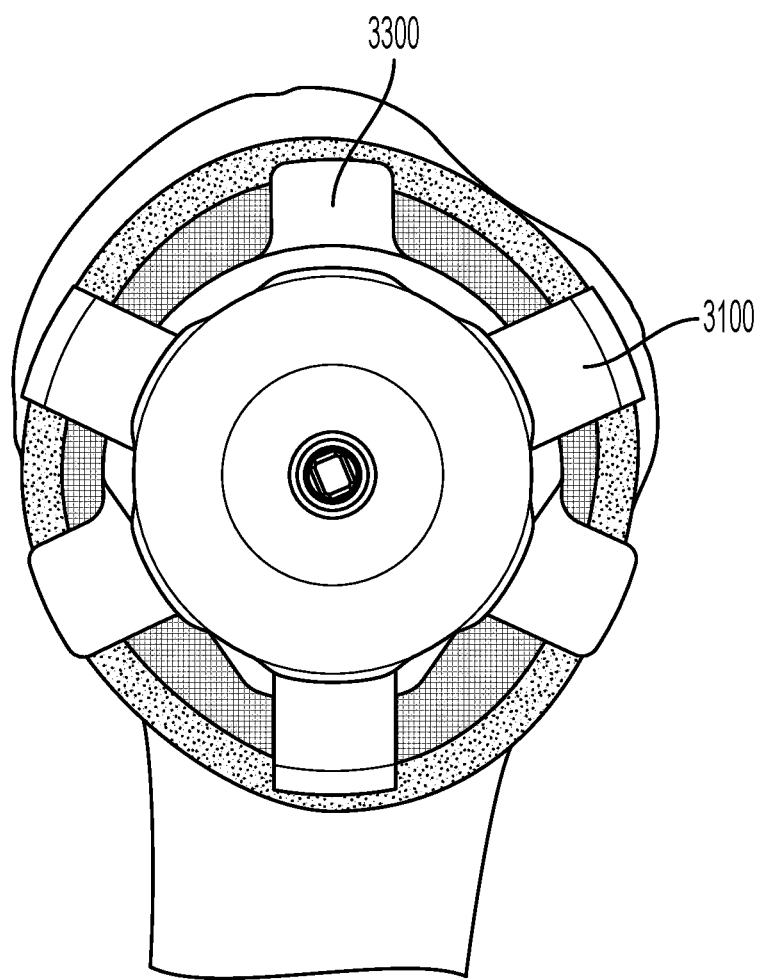
FIG. 43 is a top view of the impactor assembly of FIG. 40 positioned on the proximal humerus.

Referring now to FIG. 43, a top view of impactor assembly 3000 is shown with the impactor assembly in contact with the proximal humerus. As with impactor assembly 2000, the impaction tip 3300 of impactor assembly 3000 may include a plurality of radial extensions, three in the illustrated embodiment, which may serve as hard-stops by being in contact with the harder, denser cortical shell of the proximal humerus. As with other embodiments described herein, the distal end of housing 3100 may serve to stabilize the remainder of the system on the proximal humerus in the desired position and orientation, and the handle of the impaction member 3200 may be impacted to drive the base of the stemless humeral implant into the proximal humerus in the desired orientation.

Figure 44A:
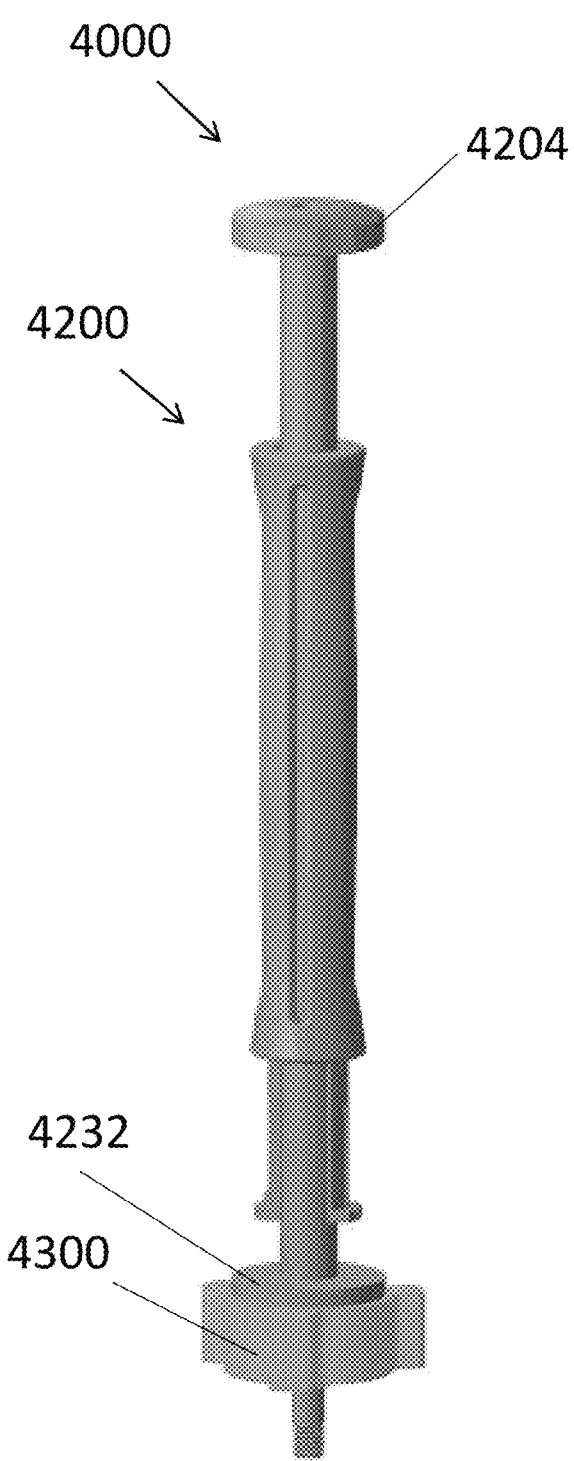
FIGS. 44A and 44B are perspective and cross-sectional views, respectively, of an impactor assembly according to another aspect of the disclosure.
Figure 44B:
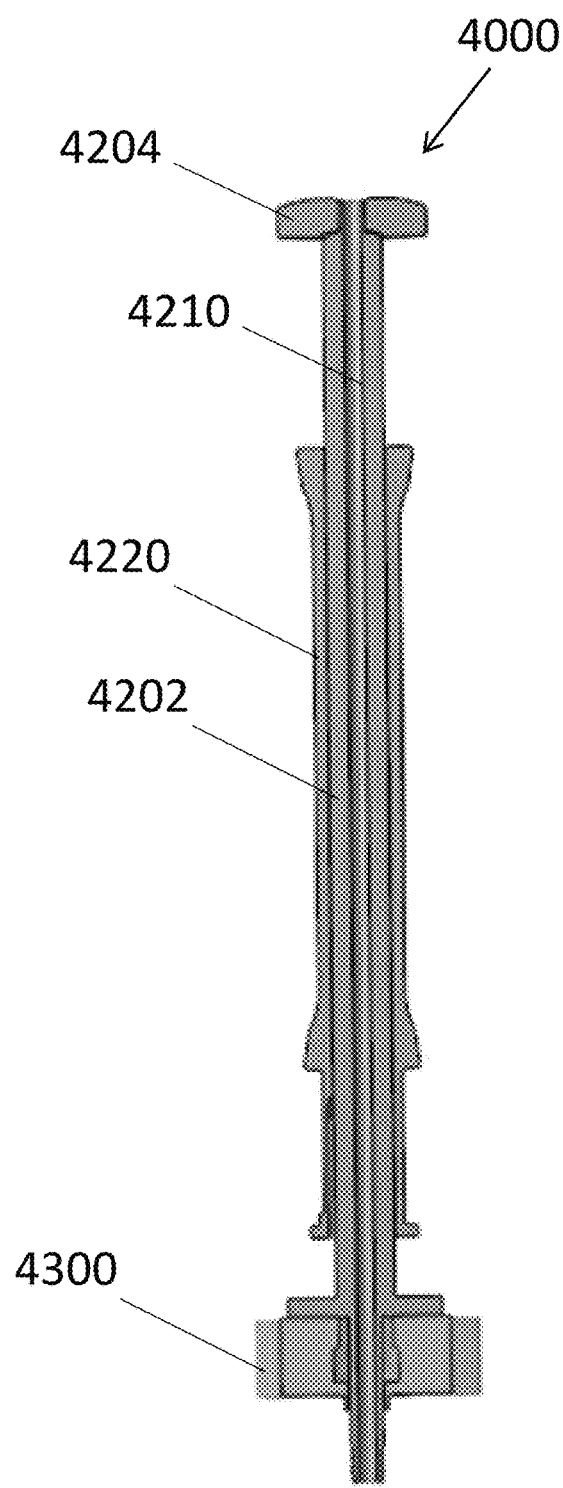

FIGS. 44A-B illustrate a further embodiment of an impactor assembly 4000 intended to provide the same or similar benefits as those described above for impactor assemblies 2000 and 3000. Various parts of impactor assembly 4000 are similar or identical to those described above in connection with impactor assemblies 2000 and 3000. Those components are generally (but not necessarily) labeled with a part number similar to the corresponding part in the impactor assemblies 2000 or 3000, using a 4000 prefix instead of a 2000 or 3000 prefix, although not all such components are labeled or separately described herein for purposes of brevity. Impaction system 4000 may include an impaction member 4200 and an impaction tip 4300, which each serve generally similar purposes to their corresponding parts in impactor assemblies 2000, 3000.

The impaction member 4200 is illustrated with the impactor assembly 4000 in FIG. 44A and is shown in cross-section with the assembly in FIG. 44B. Impaction member 4200 may be generally formed of two pieces, including handle portion 4202 (shown isolated in FIG. 44C) and a shaft portion 4220 (shown isolated in FIG. 44D).

Figures 44C, 44D:
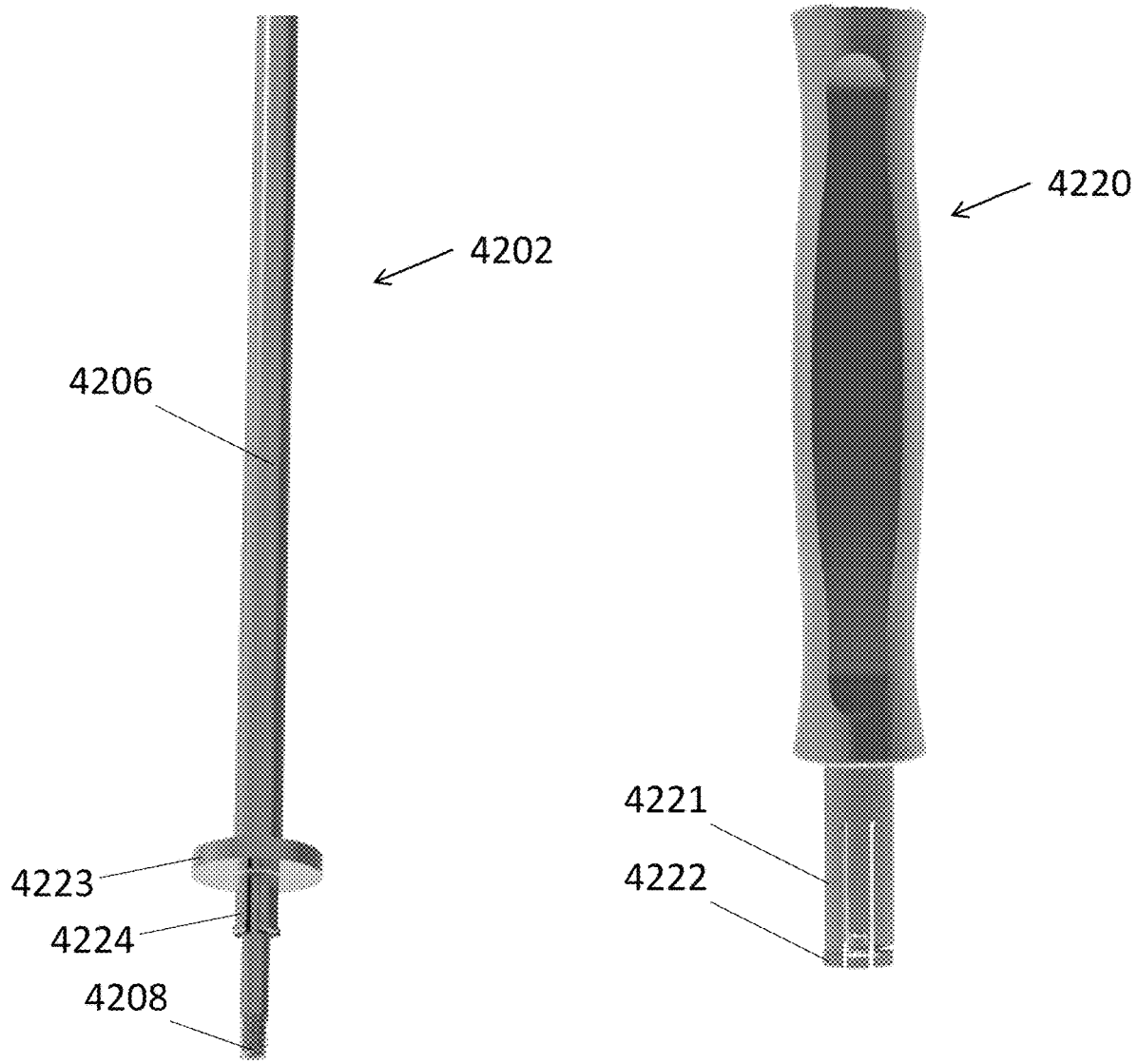
FIGS. 44C-G are various views of components of the impactor assembly.

FIG. 44C is a perspective view of the handle portion 4202 of the impaction member 4200, with the proximal or top end omitted from the drawing. The proximal end of the handle portion 4202, best illustrated in FIGS. 44A-B, may include a handle 4204 at a proximal end thereof. Preferably, handle 4204 includes a relatively large flat surface conducive to being impacted, for example by a mallet or a hammer device. In the illustrated example, handle 4204 is contoured to assist a user in turning handle 4204, and thus handle portion 4202, as described below. Handle portion 4202 may include a shaft 4206 extending distally from a center of handle 4204, terminating in a distal tip 4208, which may be threaded. A pilot wire channel 4210 may extend partially or completely through the handle portion 4202, which may be sized and shaped to receive a pilot wire therethrough. If a pilot wire is used, it may be temporarily implanted into the proximal humerus to guide the impaction system 4000, along with a prosthetic stemless humeral implant attached thereto, into a desired position and orientation with respect to the resection plane of the proximal humerus.

FIG. 44D is a perspective view of the shaft portion 4220 of impaction member 4200. Shaft portion 4220 may include lumen of passageway extending therethrough, from an open proximal end to an open distal end, through which the shaft 4206 of handle portion 4202 may extend. The shaft portion 4220 may be ergonomically designed with contours to help a user in comfortably gripping the shaft portion 4220. A plurality of fingers 4221 may extend distally from a distal end portion of the shaft portion 4220. In the illustrated embodiment, three fingers 4221 are shown extending at substantially equal intervals circumferentially around the lumen of shaft portion 4220, so that the shaft 4206 of the handle portion 4202 may extend between the fingers 4221. However, more or fewer fingers 4221 may be provided. Each finger 4221 may include a protrusion 4222 extending radially outward from a distal tip portion of the finger. Although not illustrated, fingers 4221 may be configured to mate with a stabilizer or housing similar to those described above, including for example housings 2100 or 3100. In some embodiments, the fingers 4221 are configured to connect with arms or legs of a stabilizer substantially similar to that shown in FIG. 41. It should be understood that the shaft portion 4220 may be snug over the handle member 4202 so that the shaft portion and the handle member are slideable or translatable relative to one another, but some friction may be provided to prevent free sliding if desired. Further, the distance which the shaft portion 4220 may slide may be limited via contact with the handle 4204 in the proximal direction, or the distal flange 4232 (described in greater detail below) in the distal direction.

Figure 44E:
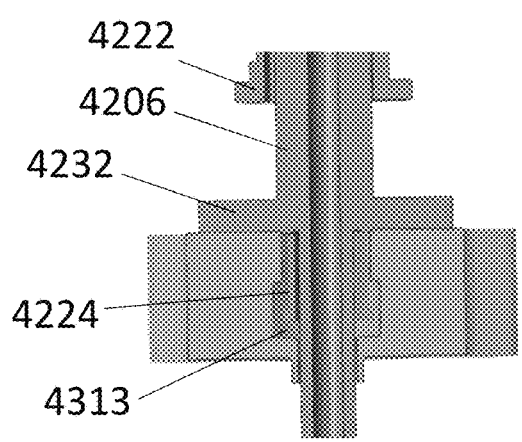
Figure 44F:
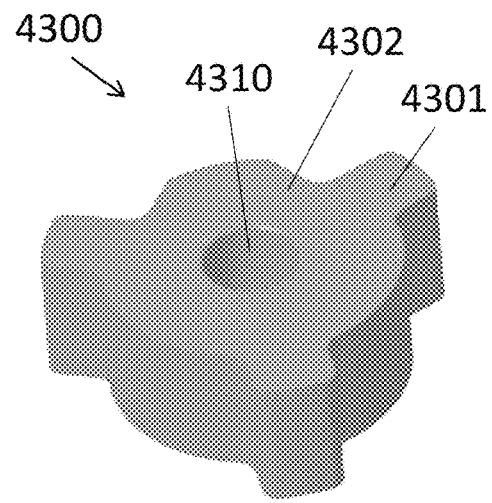
Figure 44G:
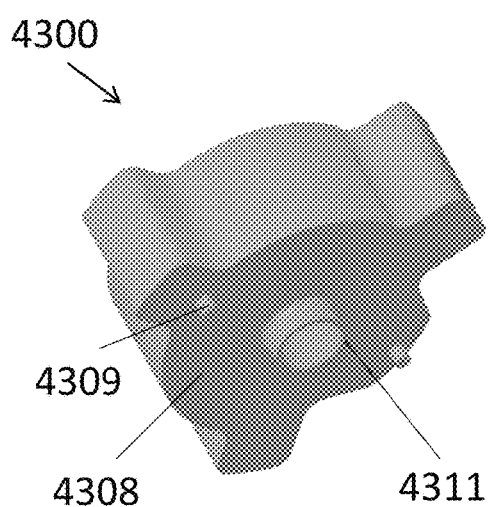

FIG. 44E illustrates a cross-section of the interface between the distal flange 4232 of the handle portion 4202 and the impaction tip 4300. The distal flange 4232 may be generally circular or cylindrical and may be integral with the shaft 4206 of the handle portion 4202. FIGS. 44F-G are top and bottom perspective views, respectively, of impaction tip 4300. As with other impaction tips described herein, impaction tip 4300 may assist in evenly transmitting forces from the strike of impaction to the base of the prosthetic stemless humeral implant. Impaction tip 4300 includes a substantially planar proximal surface 4302 that is sized and shaped to contact the distal surface of the flange 4232 of impaction member 4200, and a substantially planar distal surface 4308 that is sized and shaped to contact the proximal surface of a base of a prosthetic stemless humeral implant. Impaction tip 4300 may include an aperture 4310 at a longitudinal center thereof, which may allow a portion of shaft 4206 to pass therethrough. Generally, the impaction tip 4300 may have a generally cylindrical center with a plurality of wings 4301 extending radially outward therefrom. The generally cylindrical center of the impaction tip 4300 may be sized similarly to the distal flange 4232. The wings 4301 may extend radially outward of the distal flange 4232. The impaction tip 4300 may include one or more pins 4309 extending from the distal surface 4308. In the illustrated embodiment, two pins 4309 extend from the distal surface 4308 at substantially diametrically opposed portions of the impaction tip 2300. Further, a rim 4311 may extend from the distal surface 4308 around aperture 4310. The pins 4309 and rim 4311 may engage portions of a stemless prosthetic humeral implant, described in greater detail below.

Referring back to FIG. 44E, impaction tip 2300 may include a recessed groove 4313 in aperture 4310 between the proximal surface 4302 and distal surface 4308. The undercut or recessed groove 4313 may have a larger diameter than portions of the aperture 4310 directly distal to and directly proximal to the recessed groove. Handle portion 4202 may include a plurality of flexure members 4224 extending distally from the distal flange 4223. The flexure members 4224 may include outward protrusions at distal ends thereof, the outward protrusions sized and shaped to be received within the recessed groove 4313 so that they cannot pull out of the recessed groove. One, two, three, or more flexure members 4224 may be provided, preferably in a substantially even circumferential spacing around the distal portion of shaft 4206.

Figure 44H:
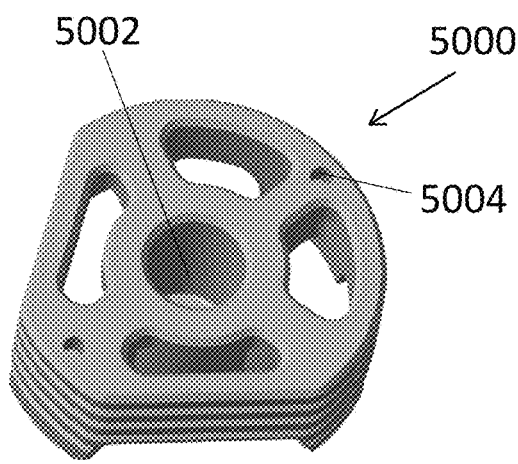
FIG. 44H is a perspective view of a base of a prosthetic stemless humeral implant that may be used with the impactor assembly of FIGS. 44A-B.

FIG. 44H illustrates an exemplary base 5000 of a stemless prosthetic humeral implant. Base 5000 can be similar to any of the bases described above, or those described in U.S. Patent Application No. 63/021,377, filed May 7, 2020 and titled "Stemless Metaphyseal Humeral Implant," the disclosure of which is hereby incorporated by reference herein. FIG. 44H illustrates the proximal surface of base 5000, which may have a general "shield" shape. A number of anchoring features may extend distally from the base 5000, the anchoring features intended for being driven into the bone of the proximal humerus to secure the base therein. The proximal surface of base 5000 may include a central aperture 5002, and one or more pin holes 5004. In the illustrated embodiment, base 5000 includes two pin holes 5004 positioned on the superior and inferior sides of the base. Preferably, base 5000 includes a number and positioning of pin holes 5004 substantially complementary to the number and positioning of pins 4309. The central aperture 5002 may be sized and shaped to receive rim 4311. Central aperture 5002 may also be threaded to engage with the threaded distal tip 4208 of shaft 4206 of handle portion 4202. Still further, a pilot hole may extend completely through central aperture 5002 so that the base 5000 may be inserted over a pilot wire.

In use, a proximal humerus may be prepared as described above, for example by resecting a substantially planar surface into the proximal humerus, and inserting a pilot wire into the proximal humerus to define the center target location for the implantation of base 5000. If not assembled previously, the impaction tip 4300 may be assembled to the handle portion 4202. For example, the distal tip 4208 of the handle portion may be passed through the aperture 4310 impaction tip 4300. As the flexure members 4224 pass into the aperture 4310, the flexure members may flex inwardly, and then "pop" back or flex outwardly once the distal protrusions of the flexure members enter the recessed groove 4313 of the impaction tip 4300. The shaft 4206 of handle portion 4202 will be able to move a small amount proximally or distally with the protrusions of the flexure members 4224 being too large to exit the aperture 4310, which may allow for vertical adjustment during tightening of the threaded distal tip 4208 to the base 5000. The distal tip 4208 of the handle portion 4202 may then be threaded into corresponding threads of the central aperture 5002 to connect the base 5000 to the handle portion 4202. During threading, the distal surface 4308 of the impaction tip 4300 will move toward the proximal surface of the base 5000. The impaction tip 4300 and base 5000 should be oriented relative to another so that, upon completion of the threading, the pins 4309 enter pin holes 5004, and the rim 4311 enters aperture 5002. With this configuration, the base 5000 will be rotationally locked relative to the impaction tip 4300.

Although not shown, a housing or stabilizer generally similar to housing 3100 may be provided with impactor assembly 4000, for example connected to the fingers 4221 of shaft portion 4220. The housing or stabilizer may include, for example, three legs or tines that extend distally beyond impaction tip 2300, for example with each tine abutting a corresponding wing 4301. With this configuration, the impaction tip 4300 may be rotationally fixed relative to the stabilizer. The impactor assembly 4000 may be slid over the pilot wire (if the pilot wire is used) until the distal end of the stabilizer contacts the prepared proximal humerus. As described above, the stabilizer may assist in confirming the desired trajectory of the base 5000. With the proper orientation confirmed, the impactor assembly 4000 may be impacted, for example via striking handle 4204 with a mallet, to drive the distal anchors of base 5000 into the bone of the proximal humerus. Upon being struck, the handle portion 4202 may be driven distally with respect to the shaft portion 4220, resulting in the impaction tip 4300 and the base 5000 also being driven distally. The wings 4301 of the impaction tip 4300 may extend radially outwardly a distance large enough to contact the harder cortical bone of the proximal humerus, providing a hard stop to limit the distance which the impaction tip 4300, and thus the base 5000, may be driven.

Figure 45A:
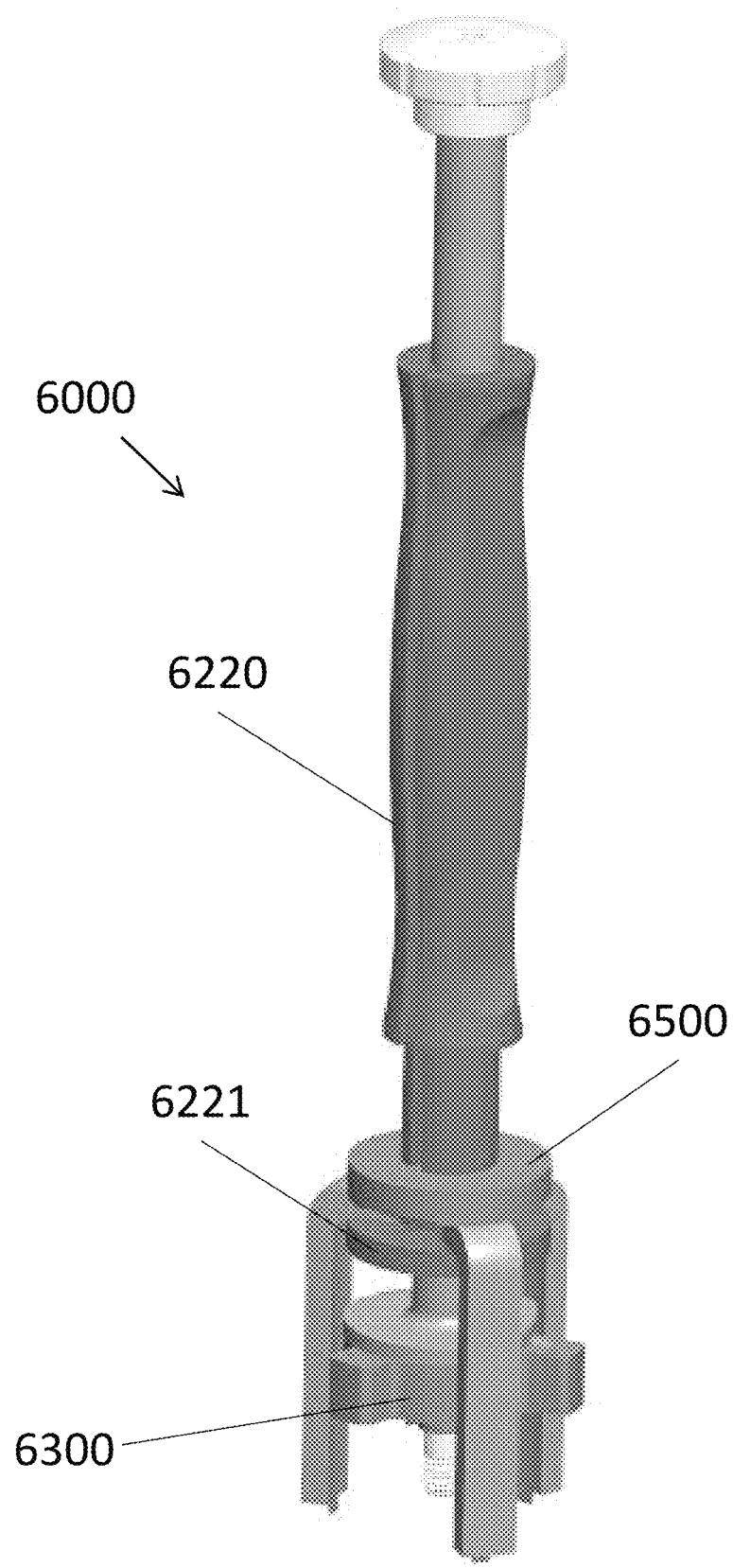
FIG. 45A a perspective view of an impactor assembly according to a further aspect of the disclosure.
Figure 45B:
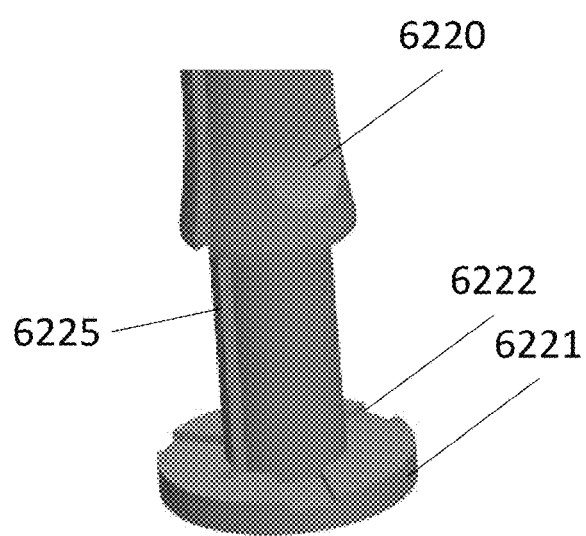
FIGS. 45B-C are various views of components of the impactor assembly.

FIG. 45A illustrates an alternate embodiment of an impactor assembly 6000. Impactor assembly 6000 may be similar or identical to impactor assembly 4000, with certain modifications, described below. The similar or identical features of impactor assembly 6000 will not be described here again.

A first difference between impactor assemblies 6000 and 4000 is that shaft portion 6220 includes a distal flange 6221. Distal flange 6221 may include a plurality of slots 6222 extending radially outward from the shaft portion 6220 to the outer perimeter of the distal flange 6221. The slots 6222 are preferably spaced at equidistantly at regular intervals around the circumference of the distal flange 6221, and the number of slots 6222 preferably corresponds to the number of tines or legs of the stabilizer member, described in greater detail below. The shaft portion 6220 may also include one or more slots 6225 extending vertically along the shaft portion 6220. Similar to other embodiments described herein, including for example that shown in FIG. 40, the vertical slot(s) 6225 may function to prevent relative rotation. For example, a member passing through the shaft portion 6220 (such as an impaction rod) may engage with slot(s) 6225 so that rotation between the impaction rod and the shaft portion 6220 is prevented.

Figure 45C:
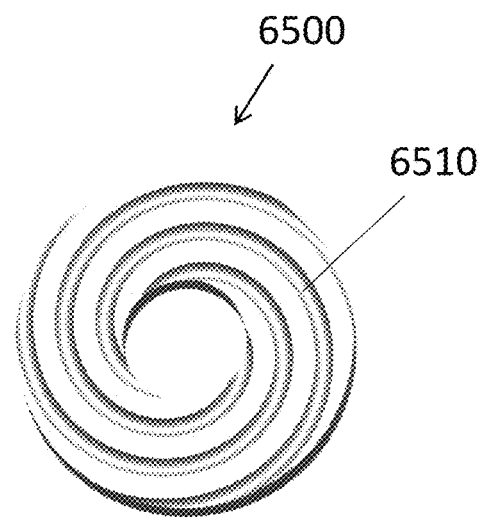

A second different between impactor assemblies 6000 and 4000 is that impactor assembly 6000 may include a helix plate 6500. Helix plate 6500 may include a substantially flat proximal surface (best shown in FIG. 45A) that surrounds a portion of the shaft portion 6220 in a position proximal to the distal flange 6221. The distal surface of helix plate 6500 is illustrated in FIG. 45C. The distal surface of helix plate 6500 may include a plurality of helical or spiral grooves 6510 spiraling or extending helically from the center aperture of helix plate 6500 to the outer circumference or diameter of helix plate 6500. In the illustrated embodiment, helix plate 6500 includes three grooves 6510. The number of grooves 6510 preferably corresponds to the number of tines or legs in the stabilizer, described in greater detail below.

Impactor assembly 6000 may include a stabilizer 6100 having a first end configured to be sandwiched between the helix plate 6500 and the distal flange 6221, and a second end adapted to contact a prepared surface of the proximal humerus, in a similar fashion as other stabilizers described herein. In the illustrated embodiment, stabilizer 6100 includes three independent legs 6110, although in other embodiments the stabilizer may include four legs, or more than four legs. The legs 6110 generally include an angled trailing end that is sandwiched between the helix plate 6500 and the distal flange 6221. The trailing end of each leg 6110 may include a distal surface that sits within a corresponding slot 6222 so that the trailing end is rotationally locked relative to the slot, but able to translate radially inwardly or outwardly relative to the slot. The trailing end of each leg 6110 may include a protrusion or pin extending from the proximal surface, the protrusion adapted to be received within a corresponding one of the grooves 6510 of the helix plate 6500.

Figure 45D:
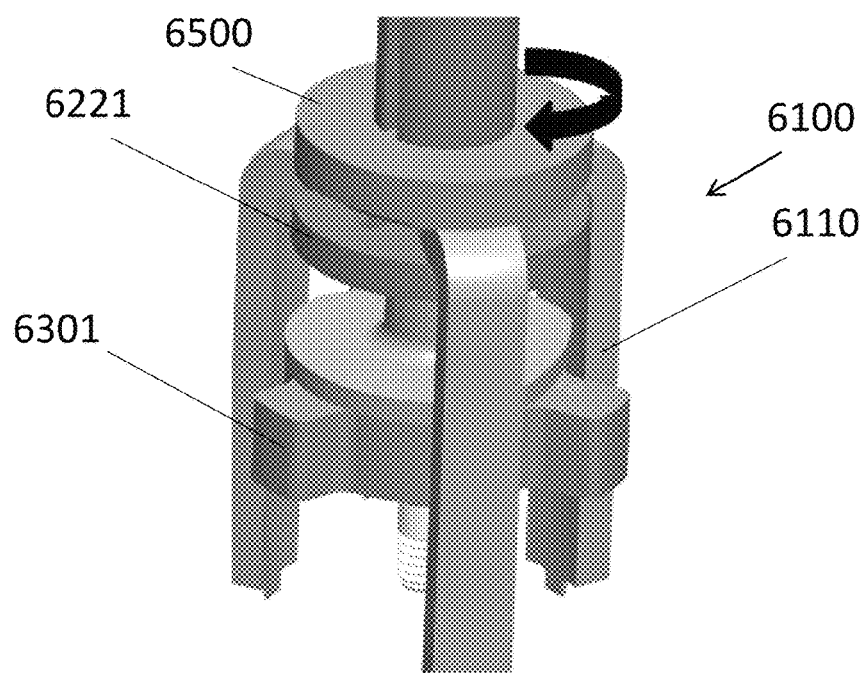
FIG. 45D is an enlarged view of a portion of the impactor assembly of FIG. 45A.

Referring to FIG. 45D, when the legs 6110 are assembled to the impactor assembly 6000, each leg 6110 extends between a pair of adjacent wings 6301 of impaction tip 6300. A user may manually rotate the helix plate 6500 relative to the shaft portion 6220 and the distal flange 6221 to rotate the helical grooves 6510 relative to the protrusions or pins in the trailing end of the legs 6110. As the helix plate 6500 is rotated, the legs 6110 are prevented from rotation relative to the distal flange 6221 by virtue of the legs being received within the slots 6222. Further, as the helix plate 6500 rotates, the pins or protrusions extending from the trailing end of the legs 6110 remain within the helical slots 6510, causing the legs 6100 to move radially toward the shaft portion 6220 or radially away from the shaft portion. In other words, rotating the helix plate 6500 causes the legs 6110 to expand or retract together to change the diameter of a circle that passes through all of the legs 6110. With this configuration, a single impactor assembly 6000 may be used with implants/anatomies of different sizes without needing multiple differently sized impactor assemblies. Thus, the user can adjust the size of the stabilizer legs 6110 for the specific implant and/or anatomy to provide the best fit of the stabilizer legs relative to the implant (which bas be similar to base 5000 or any other base described herein) and relative to the proximal humeral surface which the leading ends of the legs 6110 will engage. It should be understood that, in some embodiments, once the size/position of the stabilizer legs 6110 has been adjusted to the desired level, a feature may be provided to lock the legs in that position. For example, although not shown in FIG. 45D, the helix plater 6500 may include a plurality of pin holes extending from the proximal surface through the distal surface, and the distal flange 6221 may also include one or more indents, slots, or recesses on a proximal surface thereof. A pin or similar member may be inserted through one of the holes in the helix member and into a corresponding indent, slot, or recess in the proximal surface of distal flange 6221 so that the pin prevents further rotation. In some embodiments, holes in the helix member 6500 may correspond to pre-defined sizes of the stabilizer legs 6110 that in turn correspond to different sizes of base 5000. In other words, for example, if the base 5000 is provided in five different sizes, five holes may be provided in the helix member 6500 that correspond to the desired size of stabilizer legs 6110 for each size of base 6500.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An impactor system for impacting a base of a shoulder implant into a humerus, the system comprising:
   a housing having distal stabilizer configured to contact a proximal resected surface of the humerus, the distal stabilizer defining an open space; and
   an impaction member slidably received within the distal stabilizer, the impaction member having a proximal surface and a distal surface with a distal connection mechanism extending therefrom and adapted to contact the base of the shoulder implant,
   wherein the impaction member is movable from a first proximal position in which the base of the shoulder implant and the distal surface of the impaction member, when connected to the impaction member, is positioned within the open space defined by the distal stabilizer, to a second distal position in which the base of the shoulder implant and the distal surface of the impaction member, when connected to the impaction member, is positioned at least partially distal to the open space defined by the distal stabilizer.

2. The impactor system of claim 1, wherein the distal stabilizer includes a substantially circular rim.

3. The impactor system of claim 1, wherein the distal stabilizer includes a plurality of extensions extending along an axis substantially parallel to a longitudinal axis of the impactor system.

4. The impactor system of claim 3, wherein each of the plurality of extensions is circumferentially spaced apart from one another.

5. The impactor system of claim 3, wherein each of the plurality of extensions includes a frictional engagement member adapted to frictionally engage the proximal resected surface of the humerus.

6. The impactor system of claim 1, wherein the distal stabilizer of the housing includes a longitudinal slot sized and shaped to allow a portion of the impaction member to be laterally inserted through the longitudinal slot into the housing, the longitudinal slot extending longitudinally along a shaft extending from a proximal rim of the distal stabilizer.

7. The impactor system of claim 1, further comprising an impaction tip configured to be in contact with both a distal portion of the impaction member and a proximal surface of the base of the shoulder implant.

8. The impactor system of claim 7, wherein the impaction tip includes two apertures, and the impaction member includes a distal flange and two fingers extending distally form the distal flange, the two fingers configured to be received within respective ones of the two apertures.

9. The impactor system of claim 8, wherein the distal flange has a shape substantially similar to a shape of the proximal surface of the base of the shoulder implant.

10. The impactor system of claim 8, wherein the impaction member includes a handle having a threaded distal tip, the threaded distal tip configured to pass through the impaction tip and into a corresponding threaded portion of the base of the shoulder implant.

11. The impactor system of claim 7, wherein the impaction tip includes a plurality of extensions extending radially outward from a longitudinal center of the impaction tip, the plurality of extensions shaped and positioned to contact a cortical rim of the proximal resected surface of the humerus.

12. The impactor system of claim 7, wherein the impaction tip includes a plurality of wings extending radially outward therefrom, and the distal stabilizer includes a plurality of stabilizer legs, each of the plurality of wings adapted to extend between a pair of circumferentially adjacent stabilizer legs.

13. A method of impacting a base of a shoulder implant into a humerus, the method comprising:
    connecting the base of the shoulder implant to a distal connection mechanism of an impaction member;
    contacting a distal stabilizer of a housing to a proximal resected surface of the humerus, the distal stabilizer defining an open space;
    impacting a proximal end of the impaction member while the impaction member is slidably received within the distal stabilizer to move the impaction member from a first proximal position in which the base of the shoulder implant is positioned within the open space defined by the distal stabilizer, to a second distal position in which the base of the shoulder implant is positioned at least partially within the humerus.

14. The method of claim 13, wherein the distal stabilizer includes a substantially circular rim at a distal end of the distal stabilizer, and contacting the distal stabilizer to the proximal resected surface of the humerus includes contacting the substantially circular rim to the proximal resected surface.

15. The method of claim 13, wherein the distal stabilizer includes a plurality of extensions extending along an axis substantially parallel to a longitudinal axis of the impaction member, and contacting the distal stabilizer to the proximal resected surface of the humerus includes contacting the plurality of extensions to the proximal resected surface.

16. The method of claim 15, wherein each of the plurality of extensions includes a frictional engagement member, and contacting the plurality of extensions to the proximal resected surface includes frictionally engaging the frictional engagement members to the proximal resected surface of the humerus.

17. The method of claim 13, further comprising contacting an impaction tip with both a distal portion of the impaction member and a proximal surface of the base of the shoulder implant.

18. The method of claim 17, further comprising inserting two fingers extending distally from a distal flange of the impaction member into corresponding ones of two apertures of the impaction tip.

19. The method of claim 17, further comprising threading a threaded distal tip of a handle of the impaction member into a corresponding threaded portion of the base of the shoulder implant, the threaded distal tip passing through the impaction tip.

20. The method of claim 17, further comprising positioning a plurality of extensions that extending radially outward from a longitudinal center of the impaction tip in contact with a cortical rim of the proximal resected surface of the humerus prior to impacting the proximal end of the impaction member.

* * * * *